US008608705B2

(12) United States Patent
Peters et al.

(10) Patent No.: US 8,608,705 B2
(45) Date of Patent: Dec. 17, 2013

(54) CATHETER SECUREMENT DEVICE

(75) Inventors: Gary Peters, Peachtree City, GA (US);
Larry White, Duluth, GA (US)

(73) Assignee: C.R. Bard, Inc., Covington, GA (US)

( * ) Notice: Subject to any disclaimer, the term of this patent is extended or adjusted under 35 U.S.C. 154(b) by 51 days.

(21) Appl. No.: 13/254,797

(22) PCT Filed: Mar. 4, 2010

(86) PCT No.: PCT/US2010/026278
§ 371 (c)(1),
(2), (4) Date: Sep. 2, 2011

(87) PCT Pub. No.: WO2010/102153
PCT Pub. Date: Sep. 10, 2010

(65) Prior Publication Data
US 2011/0319830 A1    Dec. 29, 2011

Related U.S. Application Data

(60) Provisional application No. 61/157,532, filed on Mar. 4, 2009.

(51) Int. Cl.
*A61M 5/32* (2006.01)
(52) U.S. Cl.
USPC ............ 604/174; 604/175; 604/177; 604/180
(58) Field of Classification Search
USPC .......................... 604/174, 177, 179, 180, 175
See application file for complete search history.

(56) References Cited

U.S. PATENT DOCUMENTS

| 2,402,306 | A | 6/1946 | Turkel |
| 2,525,398 | A | 10/1950 | Collins |
| 2,533,961 | A | 12/1950 | Rousseau et al. |
| 2,707,953 | A | 5/1955 | Ryan |
| 3,046,984 | A | 7/1962 | Eby |

(Continued)

FOREIGN PATENT DOCUMENTS

| DE | 2 341 297 A1 | 4/1975 |
| EP | 0 169 704 A1 | 1/1986 |

(Continued)

OTHER PUBLICATIONS

ARROW International, Inc. Multiple-Lumen Central Venous Catheterization Product with ARROWgard™ Antiseptic Surface, 6 pgs., K-24703-100B (Apr. 1994).

(Continued)

*Primary Examiner* — Bhisma Mehta
*Assistant Examiner* — Lauren M Peng
(74) *Attorney, Agent, or Firm* — Knobbe, Martens, Olson & Bear, LLP

(57) ABSTRACT

A securement system (100) includes a device which permits a portion of a catheter or similar medical article to be easily anchored to a patient, desirably without the use of tape or needles and suture. A securement system for an elongated medical article comprises an anchor pad (110) and a retainer (120) mounted upon the anchor pad. The retainer (120) includes a channel (130) that has at least one abutment surface (160) corresponding to a contact surface on the medical article and a groove (210) configured to receive a spline (40) of the medical article. The medical article is placed into the channel (130). The medical article is secured within the channel by retaining at least one spline (40) and contact surface on the medical article.

22 Claims, 50 Drawing Sheets

(56) References Cited

U.S. PATENT DOCUMENTS

| | | |
|---|---|---|
| 3,064,648 A | 11/1962 | Bujan |
| 3,167,072 A | 1/1965 | Stone et al. |
| 3,245,567 A | 4/1966 | Knight |
| 3,394,954 A | 7/1968 | Sarns |
| 3,529,597 A | 9/1970 | Fuzak |
| 3,589,361 A | 6/1971 | Loper et al. |
| 3,677,250 A | 7/1972 | Thomas |
| 3,686,896 A | 8/1972 | Rutter |
| 3,766,915 A | 10/1973 | Rychlik |
| 3,812,851 A | 5/1974 | Rodriguez |
| 3,834,380 A | 9/1974 | Boyd |
| 3,856,020 A | 12/1974 | Kovac |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| 4,170,993 A | 10/1979 | Alvarez |
| 4,182,455 A | 1/1980 | Zurawin |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,250,880 A | 2/1981 | Gordon |
| 4,275,721 A | 6/1981 | Olson |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,362,156 A | 12/1982 | Feller, Jr. et al. |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,516,968 A | 5/1985 | Marshall et al. |
| 4,561,857 A | 12/1985 | Sacks |
| 4,563,177 A | 1/1986 | Kamen |
| 4,585,435 A | 4/1986 | Vaillancourt |
| 4,585,444 A | 4/1986 | Harris |
| 4,631,056 A | 12/1986 | Dye |
| 4,633,863 A | 1/1987 | Filips et al. |
| 4,650,473 A | 3/1987 | Bartholomew et al. |
| 4,660,555 A | 4/1987 | Payton |
| 4,666,434 A | 5/1987 | Kaufman |
| 4,693,710 A | 9/1987 | McCool |
| 4,711,636 A | 12/1987 | Bierman |
| 4,723,948 A | 2/1988 | Clark et al. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,792,163 A | 12/1988 | Kulle |
| 4,795,429 A | 1/1989 | Feldstein |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,934,375 A | 6/1990 | Cole et al. |
| 4,941,882 A | 7/1990 | Ward et al. |
| 4,955,864 A | 9/1990 | Hajduch |
| 4,961,505 A | 10/1990 | Moeller |
| 4,966,582 A | 10/1990 | Sit et al. |
| 4,976,700 A | 12/1990 | Tollini |
| 4,981,469 A | 1/1991 | Whitehouse et al. |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| D323,390 S | 1/1992 | Paine et al. |
| 5,084,026 A | 1/1992 | Shapiro |
| 5,098,048 A | 3/1992 | Chen |
| 5,105,807 A | 4/1992 | Kahn et al. |
| 5,112,313 A | 5/1992 | Sallee |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,248,306 A | 9/1993 | Clark et al. |
| 5,263,943 A | 11/1993 | Vanderbrook |
| 5,267,967 A | 12/1993 | Schneider |
| 5,279,578 A | 1/1994 | Cooke |
| 5,290,248 A | 3/1994 | Bierman |
| 5,292,013 A | 3/1994 | Earl |
| 5,314,411 A | 5/1994 | Bierman et al. |
| 5,336,195 A | 8/1994 | Daneshvar |
| 5,344,414 A | 9/1994 | Lopez et al. |
| 5,354,282 A | 10/1994 | Bierman |
| 5,356,379 A | 10/1994 | Vaillancourt |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,395,344 A | 3/1995 | Beisang, III et al. |
| 5,413,562 A | 5/1995 | Swauger |
| 5,456,671 A | 10/1995 | Bierman |
| 5,470,321 A | 11/1995 | Forster et al. |
| 5,484,425 A | 1/1996 | Fischell et al. |
| 5,496,283 A | 3/1996 | Alexander |
| 5,498,241 A | 3/1996 | Fabozzi |
| 5,507,535 A | 4/1996 | McKamey et al. |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,578,013 A | 11/1996 | Bierman |
| 5,620,427 A | 4/1997 | Werschmidt et al. |
| 5,626,565 A | 5/1997 | Landis et al. |
| 5,643,217 A | 7/1997 | Dobkin |
| 5,681,290 A | 10/1997 | Alexander |
| 5,685,859 A | 11/1997 | Kornerup |
| 5,690,617 A | 11/1997 | Wright |

(56) References Cited

U.S. PATENT DOCUMENTS

| | | |
|---|---|---|
| 5,702,371 A | 12/1997 | Bierman |
| 5,755,225 A | 5/1998 | Hutson |
| 5,800,402 A | 9/1998 | Bierman |
| 5,810,781 A | 9/1998 | Bierman |
| 5,827,230 A | 10/1998 | Bierman |
| 5,833,667 A | 11/1998 | Bierman |
| 5,885,251 A | 3/1999 | Luther |
| 5,947,931 A | 9/1999 | Bierman |
| 6,113,577 A | 9/2000 | Hakky et al. |
| D433,503 S | 11/2000 | Powers et al. |
| 6,213,979 B1 | 4/2001 | Bierman |
| 6,213,996 B1 | 4/2001 | Jepson et al. |
| 6,216,885 B1 | 4/2001 | Guillaume |
| 6,228,064 B1 | 5/2001 | Abita et al. |
| 6,231,548 B1 | 5/2001 | Bassett |
| 6,290,676 B1 | 9/2001 | Bierman |
| 6,332,874 B1 | 12/2001 | Eliasen et al. |
| 6,428,515 B1 | 8/2002 | Bierman et al. |
| 6,673,046 B2 | 1/2004 | Bierman et al. |
| 6,786,892 B2 | 9/2004 | Bierman |
| 6,827,705 B2 | 12/2004 | Bierman |
| 6,837,875 B1 | 1/2005 | Bierman |
| 7,250,880 B2 | 7/2007 | Hurrell et al. |
| 7,491,190 B2 | 2/2009 | Bierman et al. |
| 7,744,572 B2 | 6/2010 | Bierman |
| 7,887,515 B2 | 2/2011 | Bierman |
| 7,967,792 B2 | 6/2011 | Bierman |
| 2001/0011164 A1 | 8/2001 | Bierman |
| 2002/0133121 A1 | 9/2002 | Bierman |
| 2002/0165494 A1 | 11/2002 | Bierman et al. |
| 2002/0188255 A1 | 12/2002 | Bierman et al. |
| 2005/0075610 A1 | 4/2005 | Bierman |
| 2006/0270995 A1 | 11/2006 | Bierman |
| 2007/0149930 A1 | 6/2007 | Bierman |
| 2007/0173768 A2 | 7/2007 | Bierman |
| 2007/0276333 A1 | 11/2007 | Bierman |
| 2009/0043260 A1 | 2/2009 | Bierman |
| 2011/0178467 A1 | 7/2011 | Bierman |
| 2012/0041378 A1 | 2/2012 | Bierman |

FOREIGN PATENT DOCUMENTS

| | | |
|---|---|---|
| EP | 0 247 590 A2 | 12/1987 |
| EP | 0 114 677 A3 | 5/1989 |
| EP | 0 169 704 B1 | 11/1989 |
| EP | 0 356 683 A1 | 3/1990 |
| EP | 0 367 549 A2 | 5/1990 |
| EP | 0 367 549 A3 | 1/1991 |
| EP | 0 247 590 B1 | 12/1993 |
| EP | 0 720 836 A2 | 7/1996 |
| FR | 2 598 625 A1 | 11/1987 |
| GB | 2 063 679 | 6/1981 |
| GB | 2 086 466 | 5/1982 |
| GB | 2 178 811 | 2/1987 |
| WO | WO 80/01458 | 7/1980 |
| WO | WO 90/05559 | 5/1990 |
| WO | WO 91/16939 | 11/1991 |
| WO | WO 92/03070 | 3/1992 |
| WO | WO 92/03923 | 3/1992 |
| WO | WO 92/19309 | 11/1992 |
| WO | WO 92/19314 | 11/1992 |
| WO | WO 94/21319 | 9/1994 |
| WO | WO 97/15337 | 5/1997 |
| WO | WO 97/15342 | 5/1997 |
| WO | WO 98/53872 | 12/1998 |
| WO | WO 99/55409 | 4/1999 |
| WO | WO 2004/016309 | 2/2004 |
| WO | WO 2008/051810 A2 | 5/2008 |
| WO | WO 2010/102153 | 9/2010 |

OTHER PUBLICATIONS

ARROW® "Snap-Lock" Catheter/Syringe Adapter, 1 page, K-05500-103A (Jan. 1990).

Cravens, et al., Urinary Catheter Management, American Family Physician, vol. 61, No. 2, pp. MDG 000273-MDG 000282, Jan. 15, 2000.

Dale® Foley Catheter Holder brochure, 1 page, MDG 000344-MDG 000346, (2002).

Expert Discusses Strategies to Prevent CAUTIs, Infection Control Today, pp. MDG 000603-MDG-000609, Jun. 2005.

Grip-Lok™ Universal Tubing Securement Brochure, 1 page. MDG 000364-MDG 000366, 2005-2006.

ZEFON International., Grip-Lok™ TM Universal Tubing Securement Brochure, 1 page. MDG 000348-MDG 000349, undated, Nov. 19, 2012.

M.C. Johnson Co., Cath-Secure® Brochure, 1 page, MDG 000357-MDG 000360, undated, Nov. 19, 2012.

National Patent Services, Search Report re Patent Validity Study of U.S. Patent 5827230, pp. MDG 001319-MDG 001320, May 23, 2006.

International Search Report and Written Opinion dated May 19, 2010 for PCT Application No. PCT/US2010/026278.

Canadian Office Action dated Apr. 16, 2008 for Patent Application No. 2,413,941.

European Search Report for Application No. 04077158.6 dated Feb. 14, 2005.

European Search Report for EP 06 11 4046 dated Feb. 12, 2007.

Venetec International, Inc.'s Complaint for Patent Infringement dated Jan. 13, 2006, *Venetec International Inc.* v. *Medical Device Group, Inc.*, U.S. District Court for the Southern District of California, Case No. 06CV0083IEG, 9 pgs.

Medical Device Group, Inc.'s Answer, Affirmative Defenses and Counterclaims dated Mar. 8, 2006, *Venetec International Inc.* v. *Medical Device Group, Inc.*, U.S. District Court for the Southern District of California, Case No. 06CV0083IEG, 9 pgs.

Court's order on Claim Construction dated Mar. 6, 2007, *Venetec International Inc.* v. *Medical Device Group, Inc.*, U.S. District Court for the Southern District of California, Case No. 06CV0083IEG, 6 pgs.

Medical Device Group, Inc.'s Final Invalidity Contentions dated Apr. 25, 2007, *Venetec International Inc.* v. *Medical Device Group, Inc.*, U.S. District Court for the Southern District of California, Case No. 06CV0083IEG, 23 pgs.

Medical Device Group, Inc.'s Memorandum of Points and Authorities in Support of Motion for Summary Judgment of Noninfringement dated Jun. 1, 2007, *Venetec International Inc.* v. *Medical Device Group, Inc.*, U.S. District Court for the Southern District of California, Case No. 06CV0083IEG, 25 pgs.

Venetec's Opposition to Medical Device Group, Inc.'s Motion for Summary Judgment of Noninfringement dated Jun. 25, 2007, *Venetec International Inc.* v. *Medical Device Group, Inc.*, U.S. District Court for the Southern District of California, Case No. 06CV0083IEG, 33 pgs.

Court's order granting Defendant's Motion for Summary Judgment of Non-infringement dated Aug. 3, 2007, *Venetec International Inc.* v. *Medical Device Group, Inc.*, U.S. District Court for the Southern District of California, Case No. 06CV0083IEG, 10 pgs.

CATHETER SECUREMENT DEVICE

CROSS-REFERENCE TO RELATED APPLICATIONS

This application claims priority under 35 U.S.C. §119(e) to U.S. Provisional Application No. 61/157,532, filed Mar. 4, 2009, entitled "CATHETER SECUREMENT DEVICE," which is hereby incorporated by reference in its entirety.

BACKGROUND

1. Field of the Invention

This invention relates to a securement system used to attach a medical line to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments" one will understand how the features of this invention provide several advantages over other implantable medical articles.

One aspect of the present invention is a securement system for securing a medical article to the skin of a patient. The system comprises an anchor pad that has a lower surface at least partially covered by an adhesive for contacting the patient's skin and a medical article that has a generally elongated tubular body, a ridge circumscribing at least a portion of the tubular body, and at least one spline extending generally perpendicular to the ridge and on either side of the ridge. The ridge defines a contact surface. The system further includes a retainer being supported by the anchor pad. The retainer has a pair of upstanding walls separated by a base region to define a channel therebetween, a longitudinal access opening disposed on an upperside of the retainer, and at least one groove disposed in the channel and generally parallel to the channel. The at least one groove being sized and shaped so as to receive at least a portion of the spline when the medical article is secured within the retainer. The retainer further including an abutment surface disposed in the channel and generally perpendicular to the at least one groove. The abutment surface cooperating with the contact surface on the medical article to inhibit longitudinal movement of the medical article relative to the retainer in at least one direction when the spline is disposed within the groove and the medical article is secured within the retainer.

Another aspect of the present invention is a retainer for securing a medical article. The medical article has a generally elongated tubular body, a ridge circumscribing at least a portion of the tubular body, and at least one spline extending generally perpendicular to the ridge and on either side of the ridge. The ridge defines a contact surface. The retainer includes a pair of upstanding walls separated by a base region to define a channel therebetween and at least one groove disposed in the channel. The at least one groove being sized and shaped so as to receive at least a portion of the at least one spline of the medical article. The retainer further including an abutment surface disposed in the channel and generally perpendicular to the at least one groove. The at least one abutment surface cooperating with the contact surface to inhibit longitudinal movement of the medical article relative to the retainer in at least one direction at least when the spline is disposed within the groove and the medical article is secured within the retainer.

Another aspect of the present invention is a method of securing a medical article to a patient. The medical article has a generally elongated tubular body, a ridge circumscribing at least a portion of the tubular body, and a pair of splines extending generally perpendicular to the ridge and on either side of the ridge. The ridge defines a contact surface. The method includes providing a retainer having a channel, a pair of longitudinal grooves disposed within the channel and separated by a base surface, and at least one abutment, locating the retainer with respect to the medical article so as to generally align the pair of splines with the pair of grooves, and pushing the medical article towards the channel so that at least a portion of the splines are received within the groves. The method further includes sliding the splines of the medical article in the grooves until the contact surface of the medical article abuts the at least one abutment surface.

DETAILED DESCRIPTION OF CERTAIN EMBODIMENTS

The following description and the accompanying figures, which describe and show the preferred embodiments, are made to demonstrate several possible configurations that a securement system can take to include various aspects and features of the invention. The illustrated embodiments are shown in use with an illustrative example of a catheter hub used for connection to a connector fitting via a spin nut. The illustration of the securement device in this context is not intended to limit the disclosed aspects and features of the invention to the specified embodiments or to usage only with the illustrated catheter hub. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
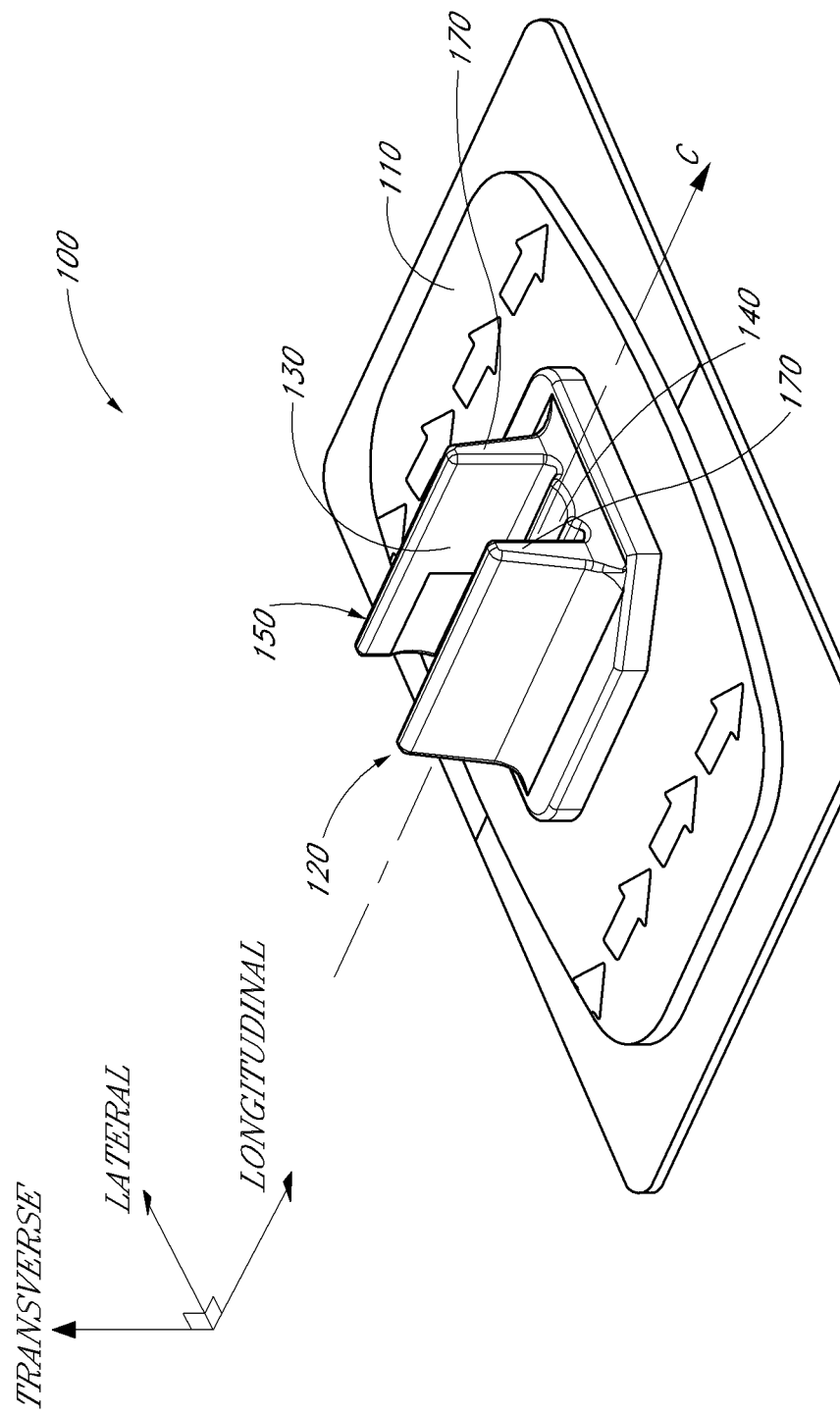
FIG. 1 is a perspective view of the securement device configured in accordance with a preferred embodiment of the present invention.

To assist in the description of these components of the securement system, the following coordinate terms are used (see FIG. 1). A "longitudinal axis" is generally parallel to a portion of the catheter hub or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or catheter hub, and therefore is substantially synonymous with the term "longitudinal" as used herein. Also, the terms "proximal" and "distal", which are used to describe the present securement system, are used consistently with the description of the exemplary applications. Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described.

The preferred embodiments of the present invention advantageously provide a medical line securement system for securing a medical article to a patient. The medical article preferably has an elongated body. The elongated body cooperates with a retainer to arrest movement of the medical article in longitudinal, lateral, and transverse directions when placed within the retainer.

In each of the embodiments described below, the retainer has a body that defines a central channel disposed above a base surface. The central channel receives a portion of the medical article. The retainer has a longitudinal access opening located on an upperside of the retainer. This access opening allows ingress or egress of the medical article. Alternatively, the medical article may be inserted in a proximal direction, or from the rear, into the channel of the retainer along the longitudinal axis. The medical article can be removed by sliding the medical in a distal direction or transverse direction. Such an arrangement allows the medical provider to align at least a portion of the medical article with the retainer before or after fixing the retainer to the patient's skin.

The retainer includes at least one abutment (preferably an abutment surface) that cooperates with at least one contact point or surface on the medical article. The one or more abutments of the retainer extend generally normal to the longitudinal axis and can be, for example, but without limitation a surface, a wall of a slot, a wall of a groove, a ridge, a protuberance, or like structures. For example, the groove can extend from a distal most end of the retainer along the longitudinal axis and partway towards the proximal end of the retainer. An abutment is formed at the location where the groove terminates. The abutment cooperates with the one or more contact points or surfaces of the medical article to inhibit longitudinal movement of the medical article through the retainer in at least a proximal direction.

At least one of the abutments is located between the ends of the retainer. The abutment will act against at least a portion of an outwardly extending member or step which defines the one or more contact points or surfaces of the medical article. In this way, the medical article will be limited in its proximal movement (i.e., movement toward the patient) once the step contacts or abuts against the abutment of the retainer. In some embodiments, an adhesive is used to further inhibit relative movement of the medical article with respect to the retainer. The retainer can have a unitary or non-unitary construction.

Ingress or egress of the medical article from the retainer may be facilitated by manipulation of the retainer. For example, a healthcare provider can bend or flex the walls apart from the medical article to ease ingress or egress of the medical article with the channel.

The retainer further inhibits distal movement of the retained medical article. For example, frictional contact between the medical article and the retainer can inhibit distal movement as can the actual shape of the medical article. An adhesive region of the channel surface can further inhibit distal movement. An adhesive wrap or cover may be employed to adhere the medical article relative to the anchor pad and retainer.

The retainer of each embodiment described below further includes an anchor pad. The lower surface of the anchor pad attaches to the patient's skin. The anchor pad may include an adhesive, such as a Hydrocolloid and Zinc Oxide adhesive. Such an adhesive may provide additional advantages in humid environments, such as typically found in a neonatal intensive care unit.

The anchor pad inhibits contact between the skin and the retainer, with the retainer and anchor pad inhibiting contact between the skin and the retained portion of the medical article.

To facilitate a complete understanding of the embodiment, the remainder of the detailed description describes the securement system with reference to the figures, wherein similar elements among the embodiments are referenced with like numerals throughout the following description.

FIG. 1 is a perspective view of a securement system 100 configured in accordance with an embodiment of the present invention. As shown in FIG. 1, the illustrated securement system 100 comprises two main components: an anchor pad 110 and a retainer 120. The flexible anchor pad 110 has an adhesive bottom side that attaches to the skin of a patient when used. The pad 110 can be attached at any number of locations on a patient's body. Thus, the securement system 100 can be used for catheterization at any location on the patient's body, e.g., on the back of the hand, medial side of the wrist in connection with catheterization of a radial artery, or on the anterior or posterior of the patient's torso in connection with epidural catheterization. The pad 110 supports the retainer 120. The retainer 120 in turn is configured to receive and secure in place the catheter hub 10.

As noted above, the securement system 100 can form a component of a securement system that also includes one or more medical articles, such as connector fittings, catheters, hubs, catheter adaptors, fluid supply lines, or other articles suitable for securement via the anchor pad and retainer. An opening in the retainer 120 is aligned with the medical article. The medical article is inserted through the opening and into the retainer 120. The anchor pad 110 is then secured to the skin of the patient, generally by an adhesive disposed upon the bottom surface of the pad. Alternatively, the anchor pad 110 may first be secured to the patient with the medical article being secured within the retainer 120. In this way, the retainer 120 secures the medical article to the patient. Thus, the retainer at least restricts, if not prevents, lateral and transverse movement of the retained section of the medical article. Additional features of the securement system 100 can restrict, if not prevent longitudinal movement of the retained section of the medical article in at least one direction. The embodiment illustrated is preferably for use with a catheter hub as described with reference to FIGS. 14 and 15. The embodiments of the anchor pad and the retainer are described in more detail below.

Catheter Hub

Figure 14:
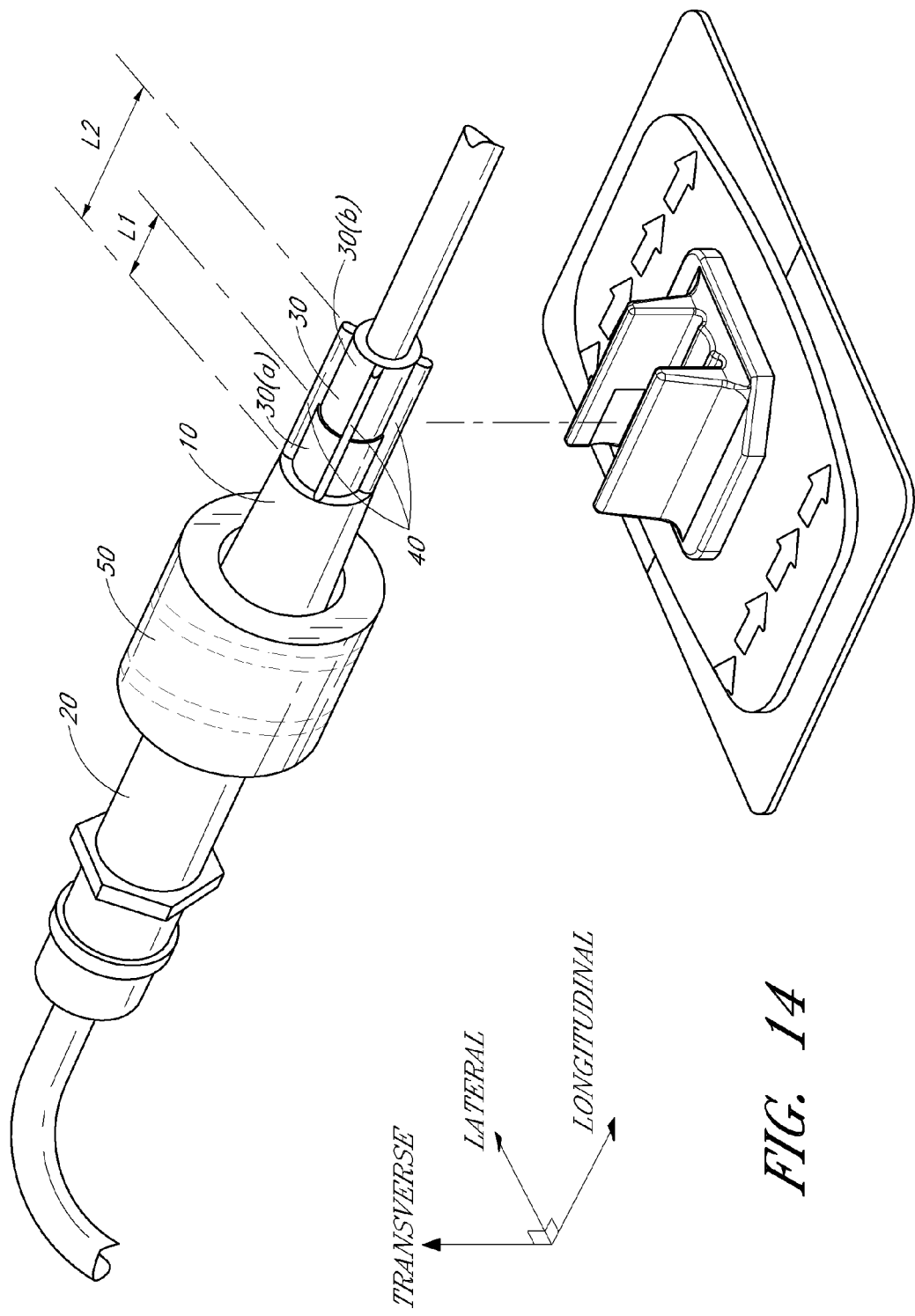
FIG. 14 is a perspective view of a catheter hub arranged above the retainer of the securement device from FIG. 1.

With reference to FIG. 14, a coupling is formed between a catheter hub 10 and a connector 20. Although the catheter hub 10 is illustrated as being a BD L-Cath Catheter for use with PICC and Midline catheters of the type disclosed in publication "The BD Family of PICC and Midline Catheters" published by BD Medical of Sandy, Utah, which is hereby incorporated by reference in its entirety and attached hereto, other types of catheters and adaptors can be used as well with the present securement system 100. Those skilled in the art can readily select the type of catheter to be used with the present securement system 100 and can modify the securement system according to the teachings of the present invention to suit the particular application (e.g., venous, arterial, epidural, peripheral, etc.).

Thus, the principles of the present invention are not limited to catheters or to the specific type of catheter disclosed in the publication "The BD Family of PICC and Midline Catheters." Instead, it will be understood by one of skill in this art, in view of the present disclosure, that the securement system disclosed herein also can be successfully utilized in connection with other types of catheters, including those with other arrangements of splines with different lengths or of staggered positions along the catheter hub tubular body. In addition, it will be understood by one of skill in this art that the securement system disclosed herein also can be successfully utilized in connection with other types of medical articles, including other types of catheters, fluid drainage and delivery tubes, and electrical wires. For example, but without limitation, the retainer disclosed herein can be configured to secure peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein. Thus, the illustration and description of the securement system in connection with a catheterization system, which includes a catheter hub similar to that disclosed in the publication "The BD Family of PICC and Midline Catheters," merely exemplifies one possible application of the present securement system.

Figure 15:
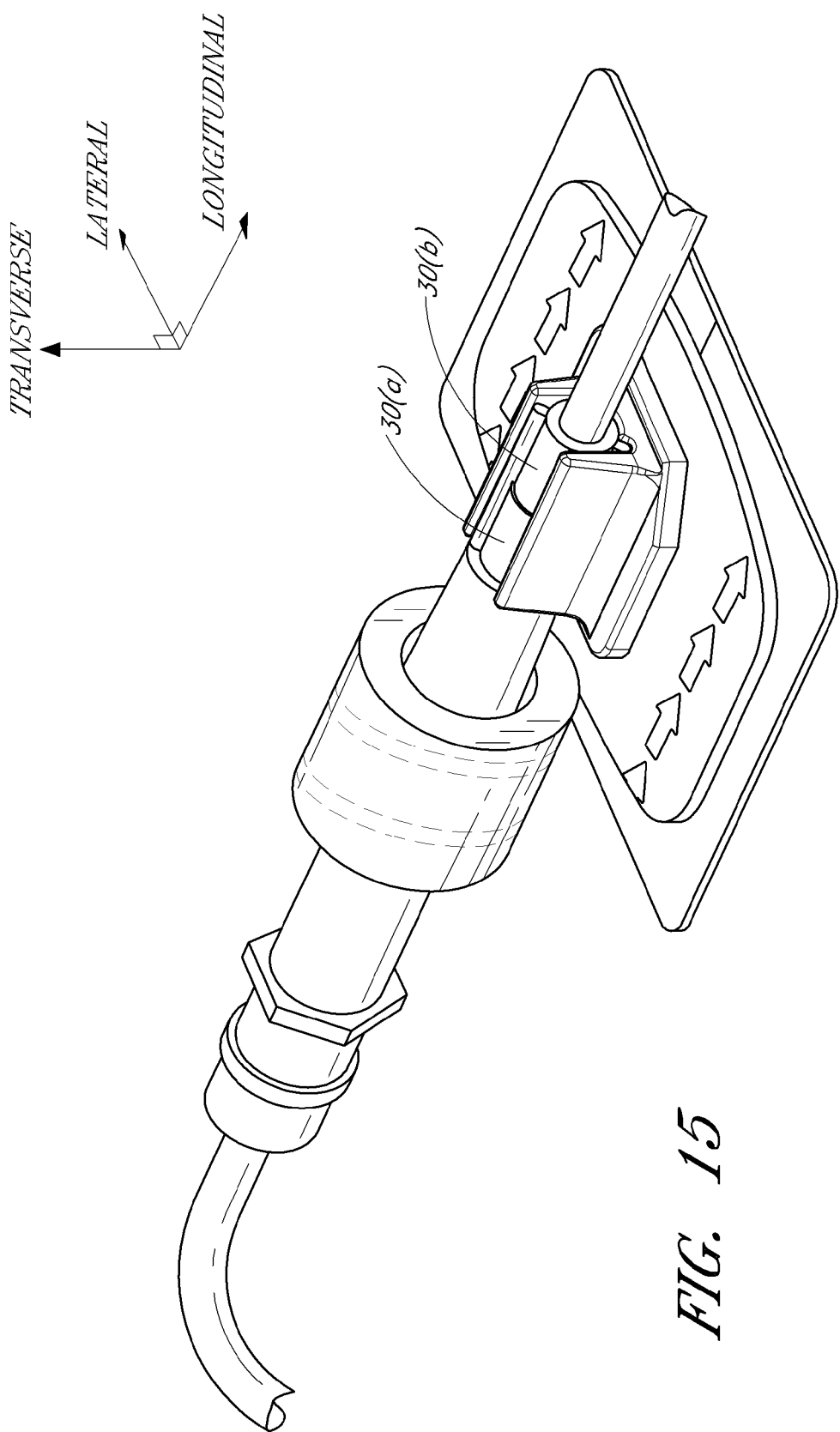
FIG. 15 is a perspective view of the catheter hub secured to the retainer of the securement device from FIG. 1.
Figure 16:
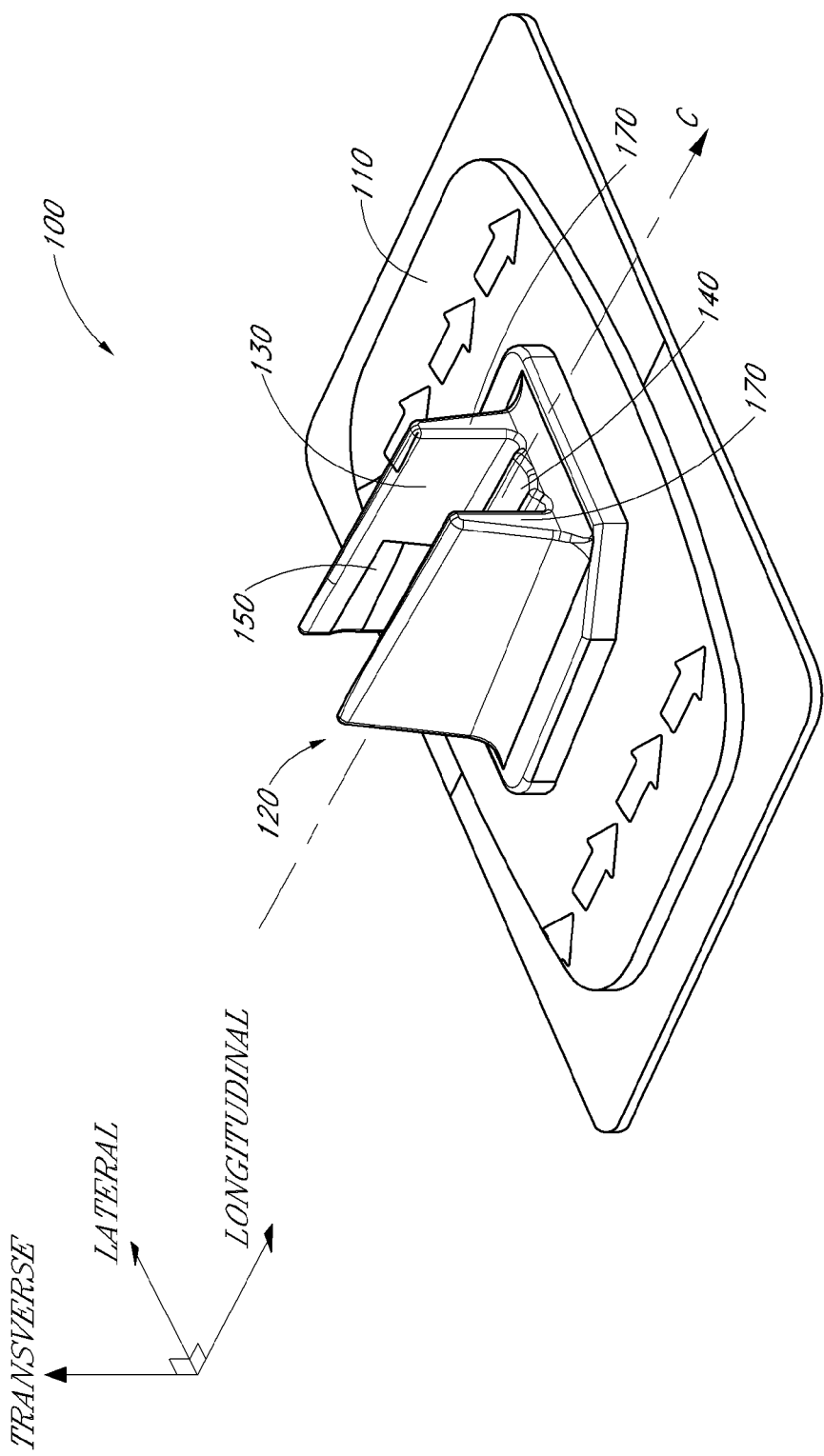
FIG. 16 is a perspective view of the securement device configured in accordance with another preferred embodiment of the present invention that includes an adhesive spot and an incident angle of seven degrees.
Figure 17:
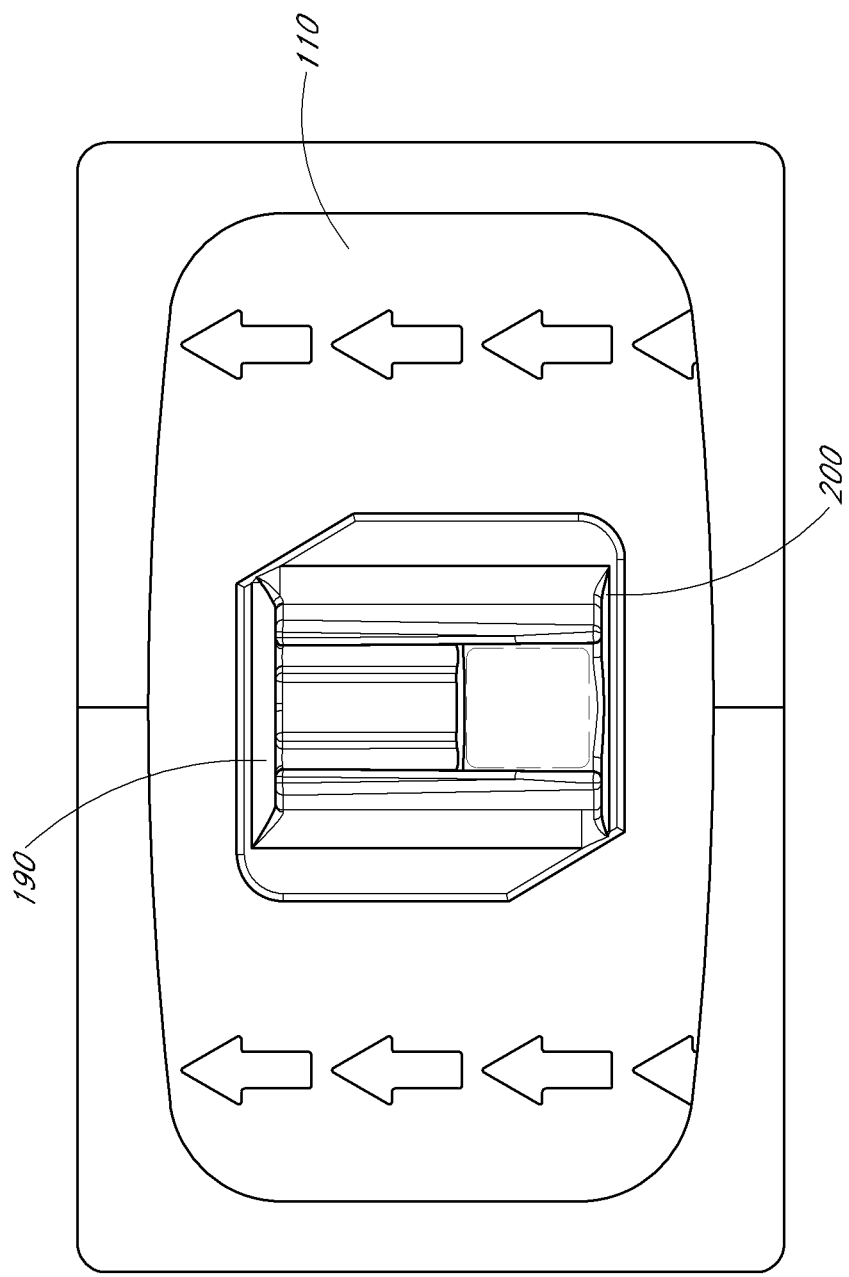
FIG. 17 is a top plan view of the retainer and anchor pad of FIG. 16.
Figure 18:
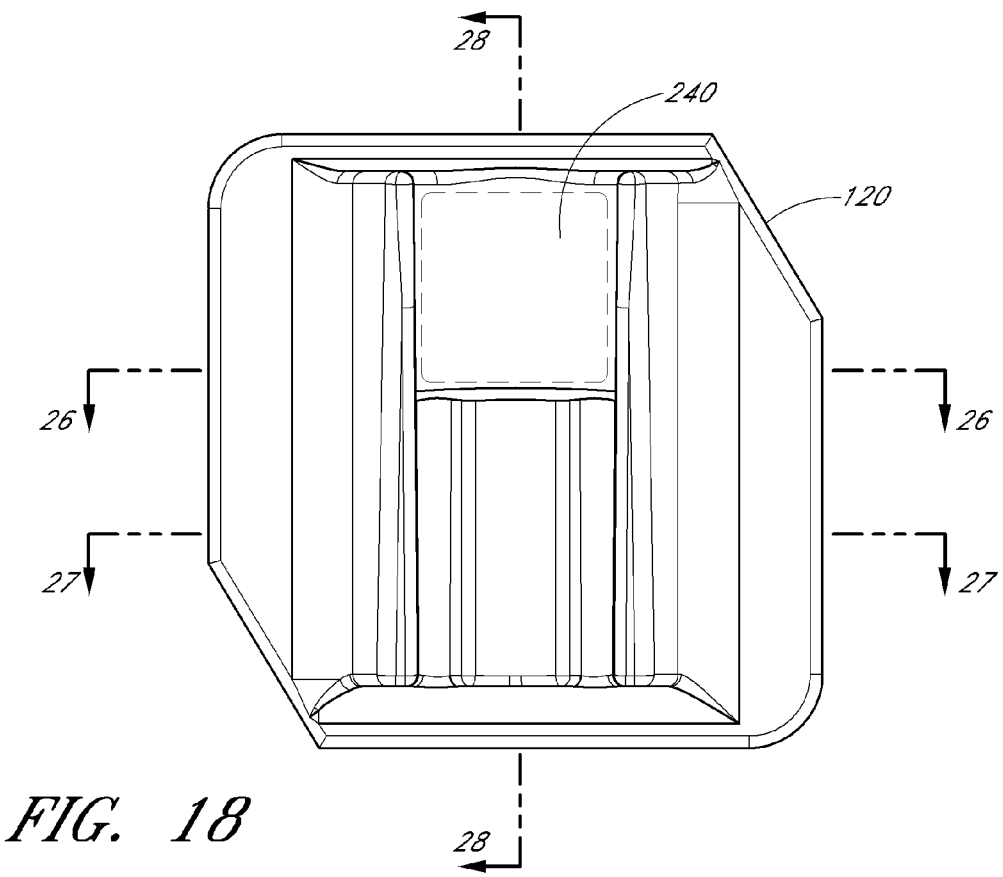
FIG. 18 is a top plan view of the retainer of FIG. 17 showing the adhesive spot in a channel of the retainer.
Figure 19:
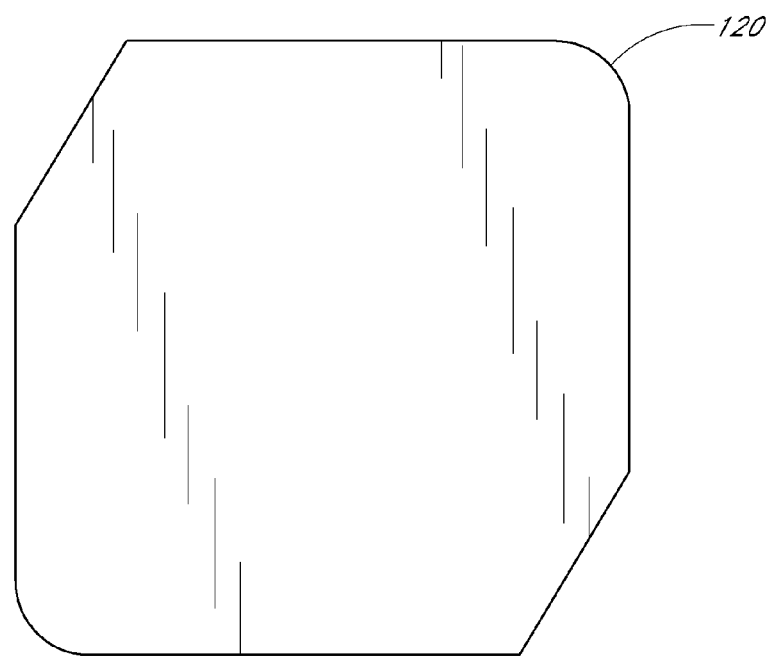
FIG. 19 is a bottom view of the retainer of FIG. 18.
Figure 20:
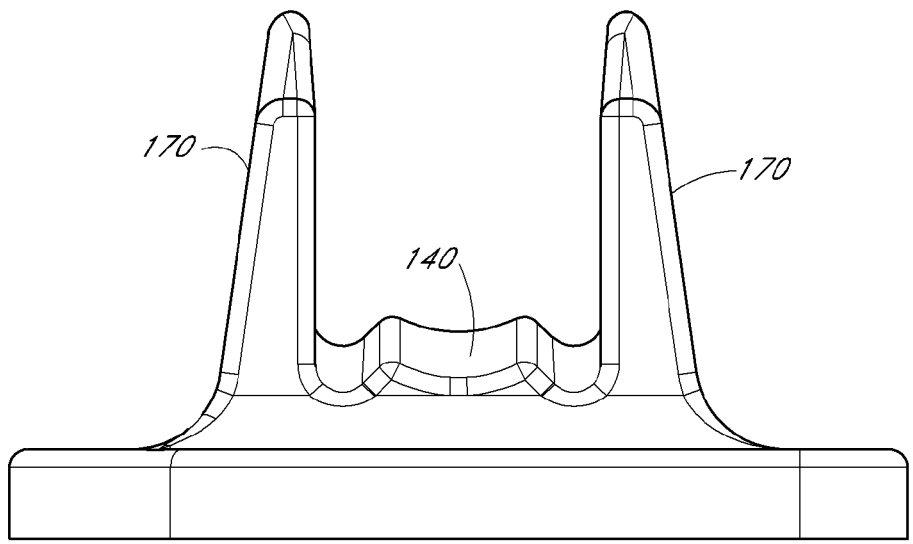
FIG. 20 is a front side view of the retainer of FIG. 18.
Figure 21:
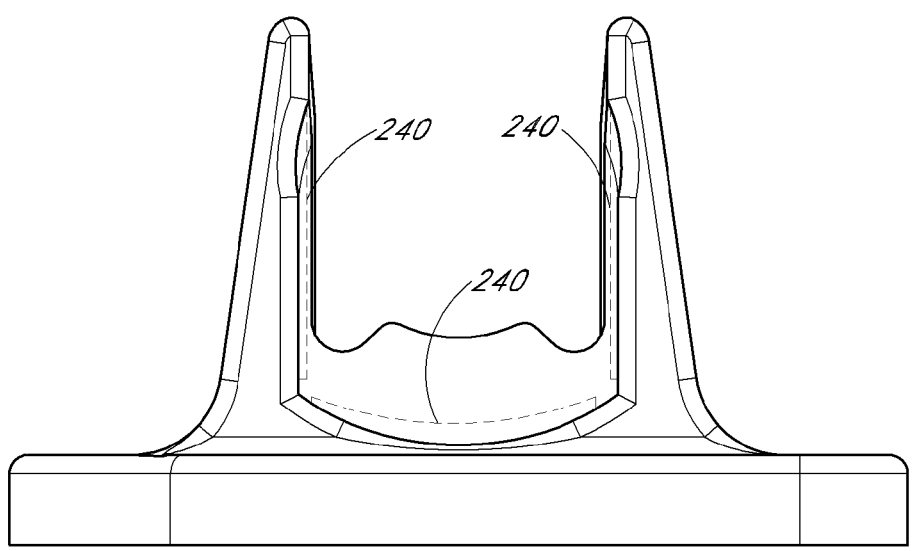
FIG. 21 is a rear side view of the retainer of FIG. 18.
Figure 22:
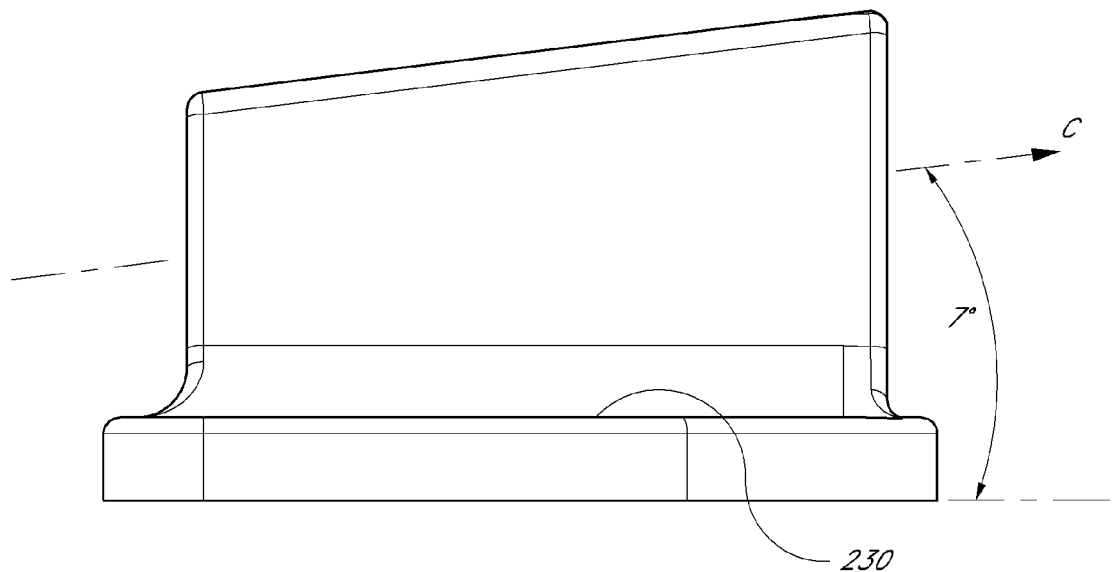
FIG. 22 is a side view of the retainer of FIG. 18.
Figure 23:
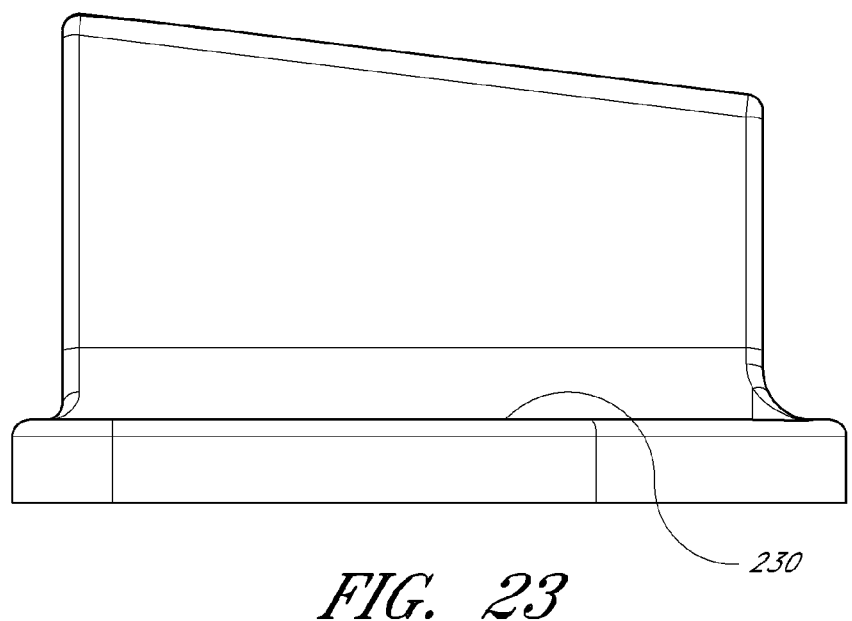
FIG. 23 is an opposite side view of the retainer of FIG. 18.
Figure 24:
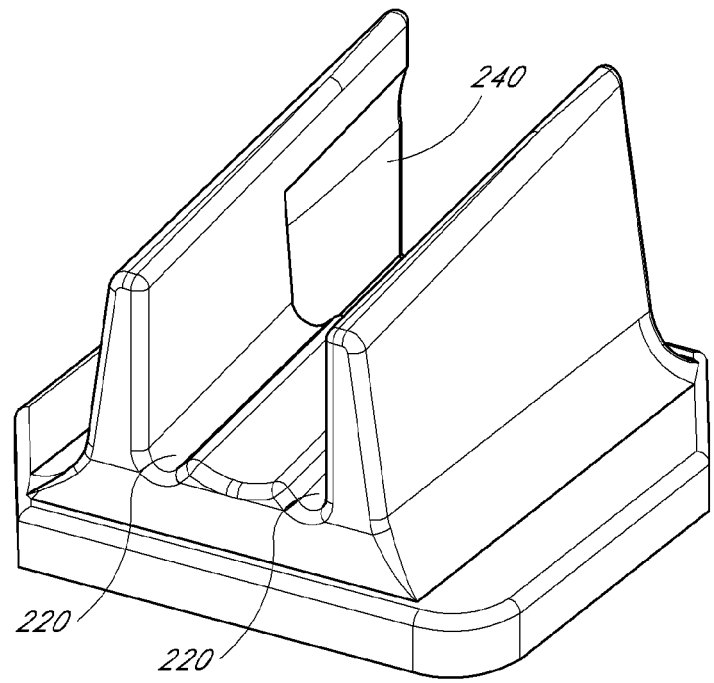
FIG. 24 is a front perspective view of the retainer of FIG. 18.

As best seen in FIGS. 14 and 15, the catheter hub 10 comprises a tubular body 30 having a plurality of diameters along the longitudinal length of the body 30 between the longitudinal ends of the splines 40. The illustrated body 30 includes a first diameter 30(a) and a second diameter 30(b) disposed on the proximal side of the first diameter 30(a). A ridge is formed at the intersection of the two diameters. Preferably the first diameter 30(a) is greater that the second diameter 30(b) so as to form a plurality of contact surfaces facing in the proximal direction at the interface between the first and second diameters. In the illustrated embodiment, four contact surfaces are formed on the tubular body 30 at this location. The longitudinal length of the tubular body 30 corresponding to the first diameter 30(a) is length $L_1$.

The proximal end of the tubular body 30 includes a series of axially extending splines 40 projecting outward from the tubular body 30. In particular, the tubular body 30 includes at least four axially elongated splines 40 that are equally spaced around the tubular body 30. The splines 40 lie at a position 90° apart from each other. The splines 40 have a generally rectangular shape that tapers to a rounded surface on the lateral edge of the rectangular body. The splines 40 have a longitudinal length $L_2$.

The catheter hub 10 includes a third diameter adjacent to the distal side of the first diameter 30(a). Four additional contact surfaces are formed at the interface between the first and third diameters. The distal end of the catheter hub 10 is configured to engage the proximal end of the connector 20. A central lumen extends through the tubular body 30. The connector 20 includes a spin nut 50 disposed on its distal end. The spin nut 50 comprises a generally tubular sleeve having a cylindrical exterior surface, a proximal annular flange, and a series of axially extending grip rails.

Retainer

Figure 2:
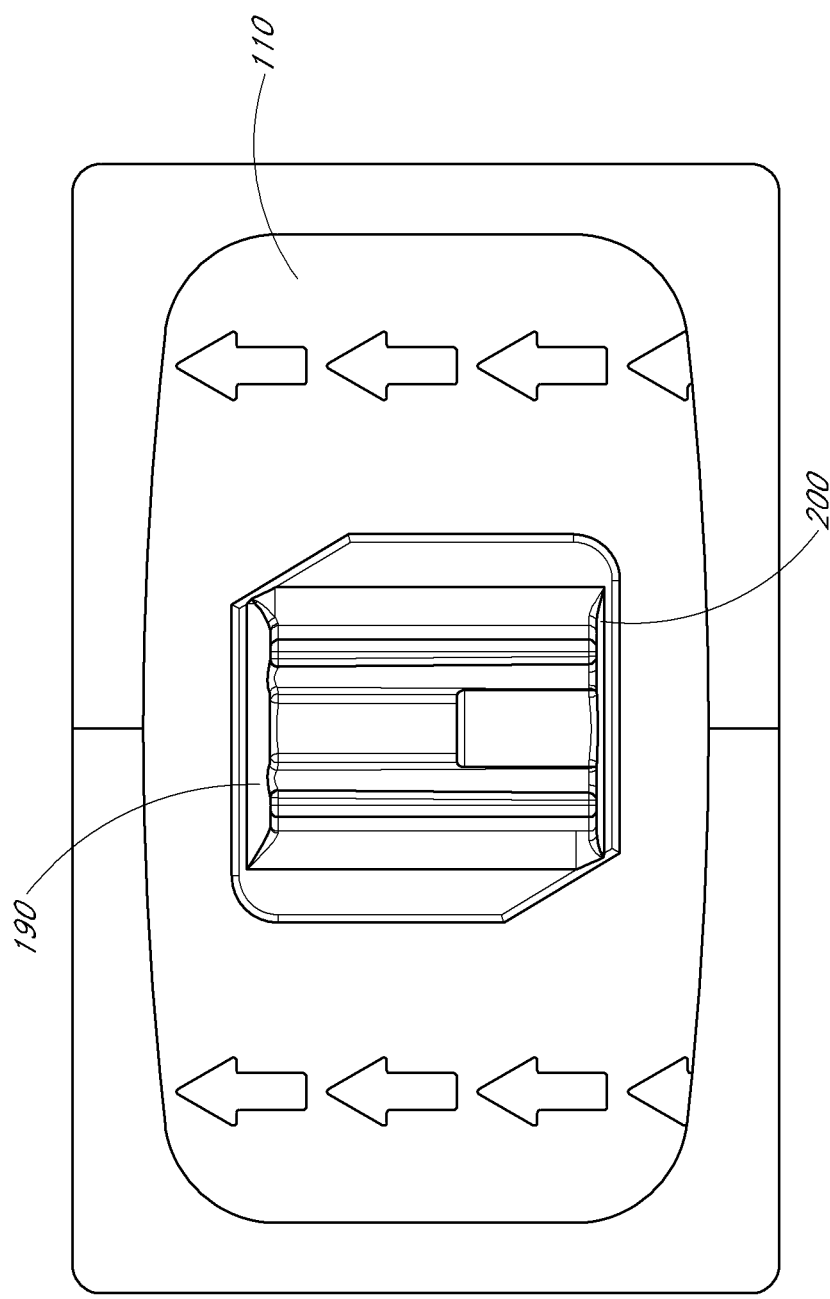
FIG. 2 is a top plan view of the retainer and anchor pad of FIG. 1.
Figure 3:
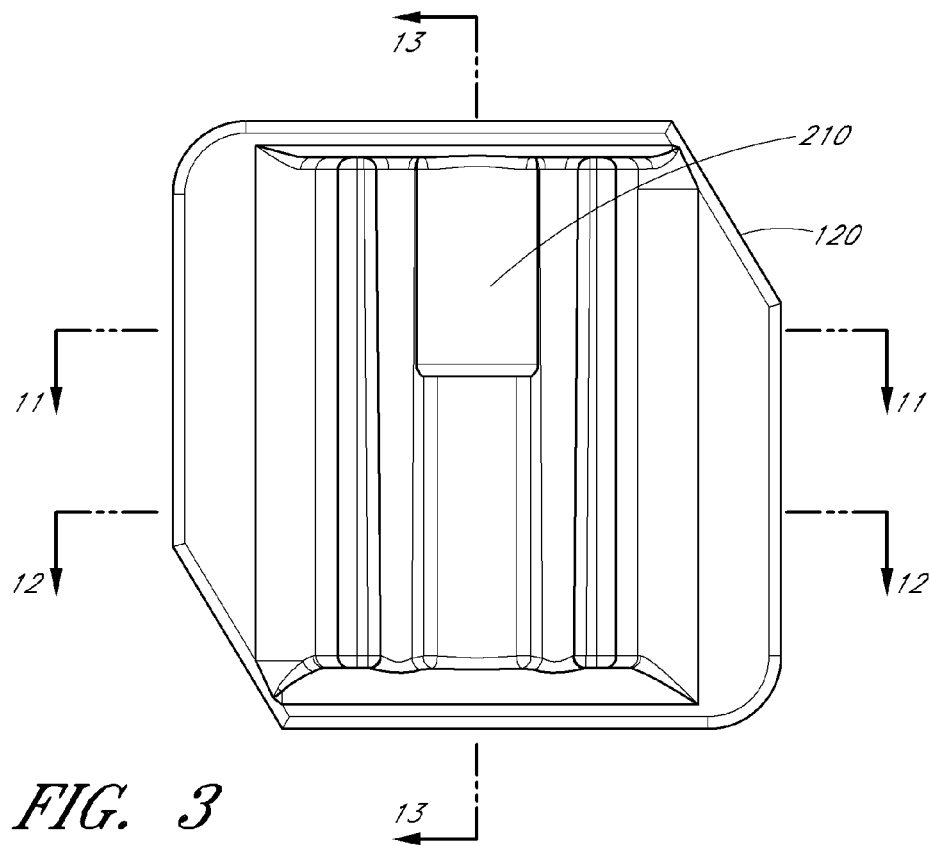
FIG. 3 is a top plan view of the retainer of FIG. 2.
Figure 4:
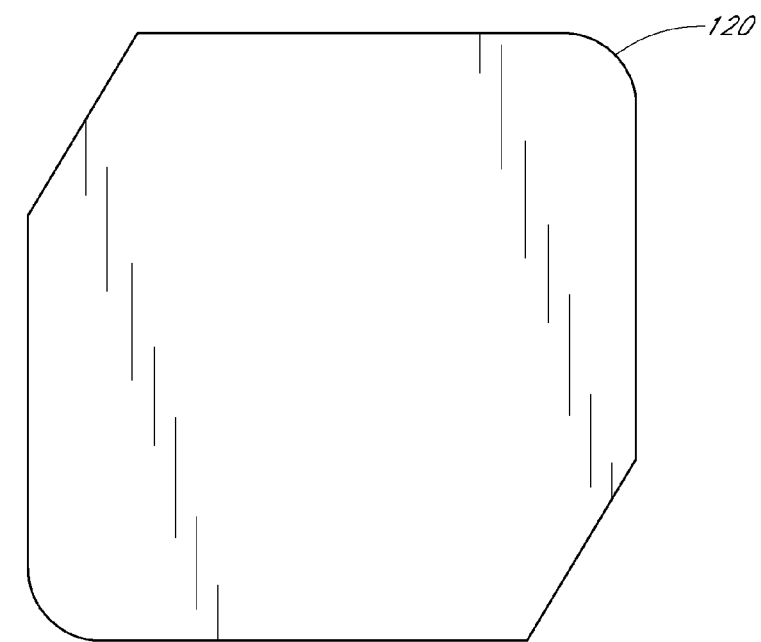
FIG. 4 is a bottom view of the retainer of FIG. 3.

FIGS. 3-13 illustrate the retainer 120, which is configured in accordance with a preferred embodiment of the present invention. The retainer 120 defines a central channel 130 disposed above a base region or base surface 140. As seen in FIG. 2, the retainer 120 includes proximal and distal end portions 190, 200. The channel 130 extends through these portions 190, 200 and is open at each of its ends through end walls of the retainer 120. The channel 130 extends about a central, longitudinally extending axis C and has an opening 150 that faces away from the base surface 140. At least a portion of the channel 130 has a lateral width that is smaller than a diameter of a portion of the catheter so as to define one or more abutment surfaces, as described below in greater detail.

Figure 6:
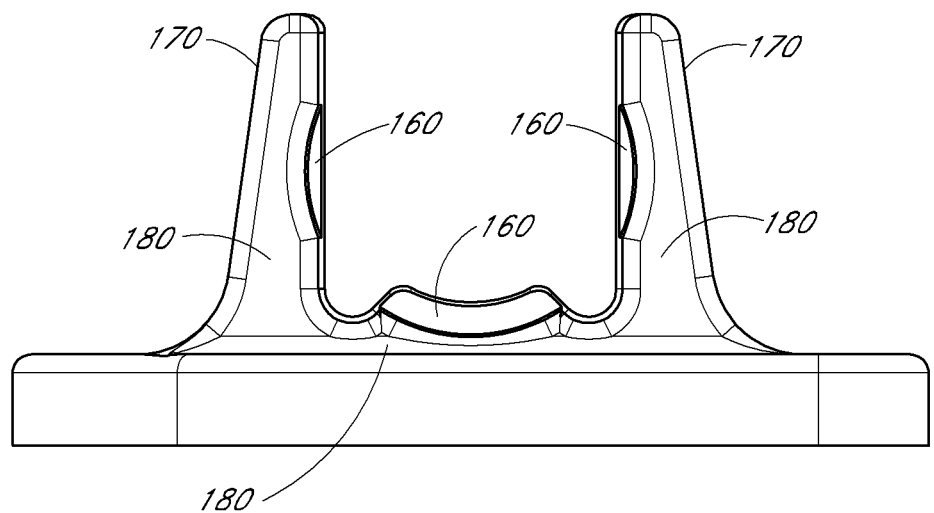
FIG. 6 is a rear side view of the retainer of FIG. 3.

As best seen in FIG. 6, the retainer 120 also includes a plurality of abutment surfaces 160, 180. The abutment surfaces extend outwardly from the channel 130 along the central axis C. The abutment surfaces can be disposed between the proximal and distal ends of the retainer 120 and/or on one or both ends of the retainer 120.

Figure 7:
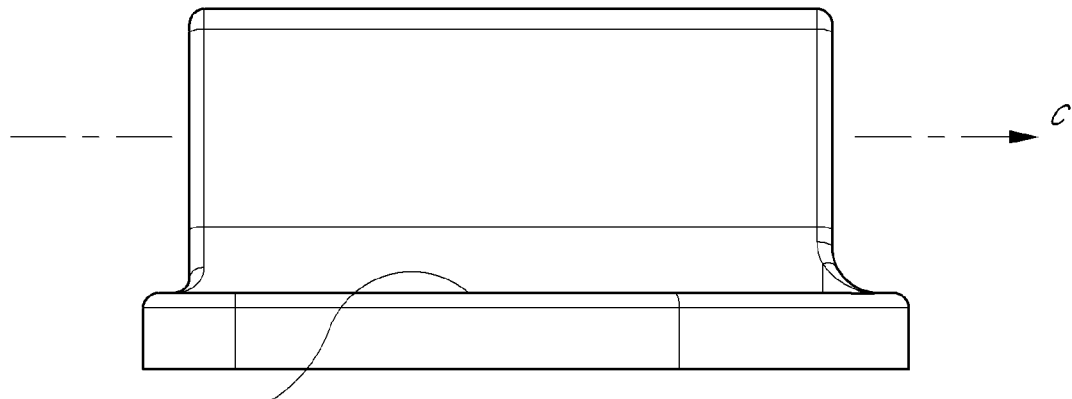
FIG. 7 is a side view of the retainer of FIG. 3.
Figure 8:
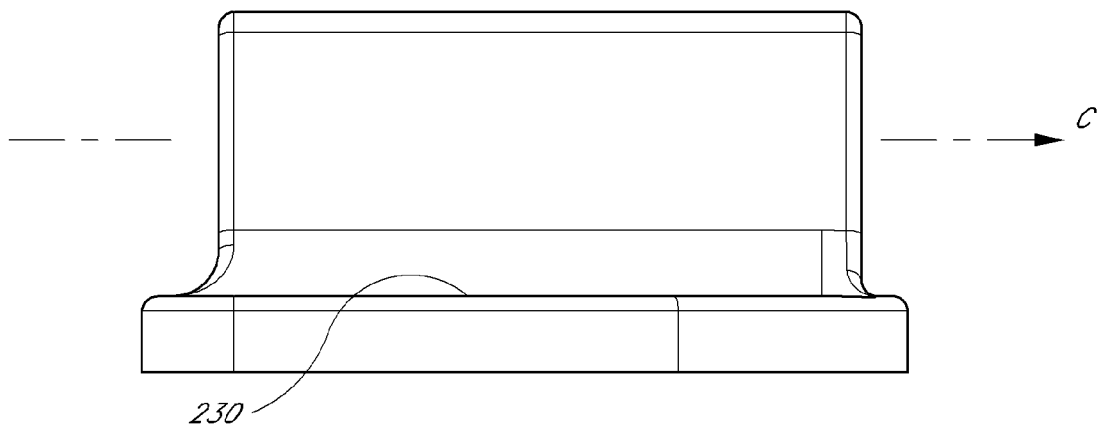
FIG. 8 is an opposite side view of the retainer of FIG. 3.

FIGS. 7 and 8 illustrate that the channel axis C is parallel to the base surface 140 of the retainer 120. An incident angle θ is defined between the base surface 140 and the channel axis C. Additional embodiments disclosed herein include various incidents angles to provide minimal stress and strain on the inserted catheter lumen.

Figure 9:
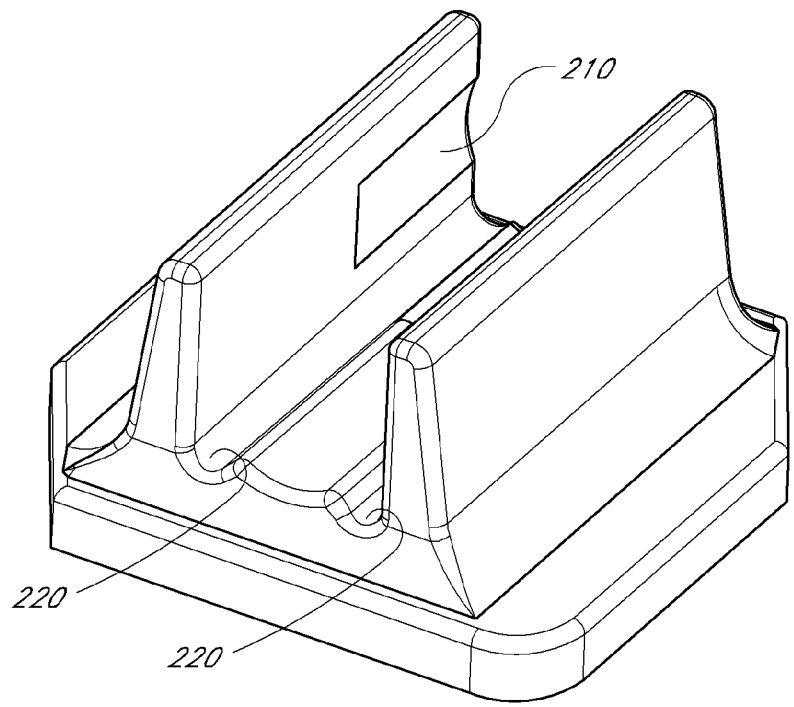
FIG. 9 is a front perspective view of the retainer of FIG. 3.
Figure 10:
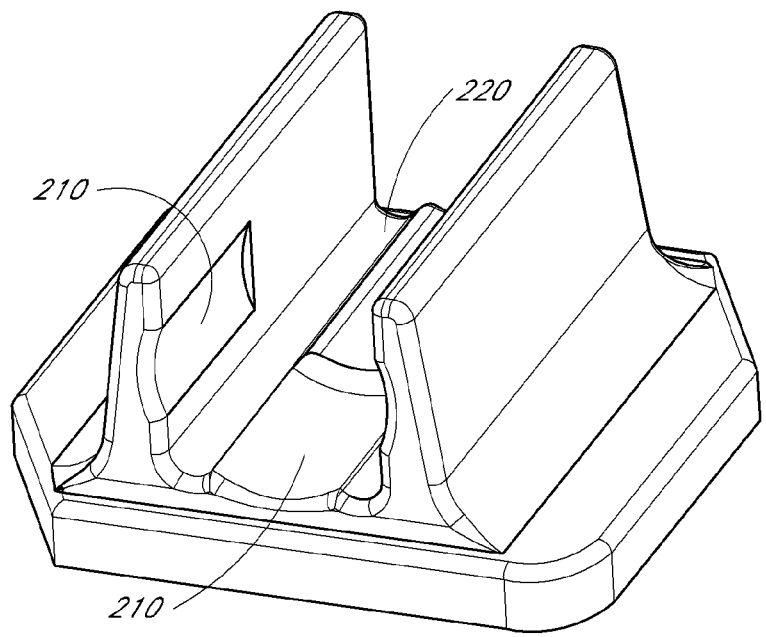
FIG. 10 is a rear perspective view of the retainer of FIG. 3.

FIGS. 9 and 10 illustrate the walls 170 of the retainer 120 between which the channel 130 passes. At least some of the abutment surfaces are defined by grooves in the retainer 120. For example, longitudinally extending grooves 210 formed in the walls 170 define intermediate abutment surfaces 160 at the proximal ends of the grooves 210. These abutment surfaces 160 are formed on an inner side of the wall 170 or base surface 140, and in the illustrated embodiment, are disposed near the middle of the retainer along the central or longitudinal axis C. In the illustrate embodiment, there are three intermediate surfaces 160, one in each of the base surface 140 and side walls 170. Each intermediate surface 160 lies generally normal to the central axis C of the channel 130 and is laterally aligned with the other two intermediate surfaces 160. The abutment surface can be discontinuous and/or circumscribe the channel for approximately 180 degrees.

The plurality of abutment surfaces further includes one or more distal-most abutment surfaces 180. The intermediate surfaces 160 lie between the proximal-end of the retainer 120 and the distal-most abutment surfaces 180 and are defined on the side walls 170 and base surface 140. The distal-most abutment surfaces 180 and the intermediate surfaces 160 preferably are separated by a distance that is generally equal to the longitudinal length between steps along the tubular body of the catheter hub. For example, the longitudinal length of the grooves 210 is preferably equal to or less than length L1 as illustrated in FIG. 14.

With the groove 210 having a length of no greater than L1, the intermediate surfaces 160 are disposed from the distal end portion 200 the same as or less than the distance corresponding to the longitudinal length of the first diameter 30(a) of the catheter hub 10. In this way, the proximal facing contact surfaces on the first diameter 30(a) will contact the intermediate surfaces 160 when the catheter hub is secured within the retainer 120.

Each wall 170 additionally has a generally flat, upstanding surface defined between the proximal end portion 190 and the distal end portion 200. The grooves 210 are defined in the upstanding surface and have a concave shape relative to the channel axis C. The radius of curvature preferably matches or at least approximates the radius of the first diameter 30(a) of the catheter hub 10. The grooves 210 of the channel inhibit unintentional transverse movement of catheter hub 10. For this purpose, the grooves 210 together have a generally truncated, circular cross-sectional shape that extends through an arc of greater than 180°. The grooves 210 have a diameter sized to receive the first diameter 30(a) of the tubular body 30. In an exemplifying embodiment, the grooves 210 together extend through an arc of about 200° about the channel axis C. As most clearly shown in FIG. 11, the channel section, in cross-section, thus extends through an arc of a little more than 180° about the channel axis c such that the lateral width of the opening 150 is slightly smaller to the overall diameter of the grooves 210. This allows for the tubular body 30 of the catheter hub 10 to be snapped into the central channel 130.

The edge of each wall 170 located above each groove 210 thus reduces the lateral width of the channel 130 as defined between the edges of each wall 170. In this manner, the walls 170 either grip onto or at least extend over the first diameter 30(a) portion of the catheter hub 10 to inhibit unintentional transverse movement of the catheter hub 10 once situated within the retainer 120.

Figure 11:
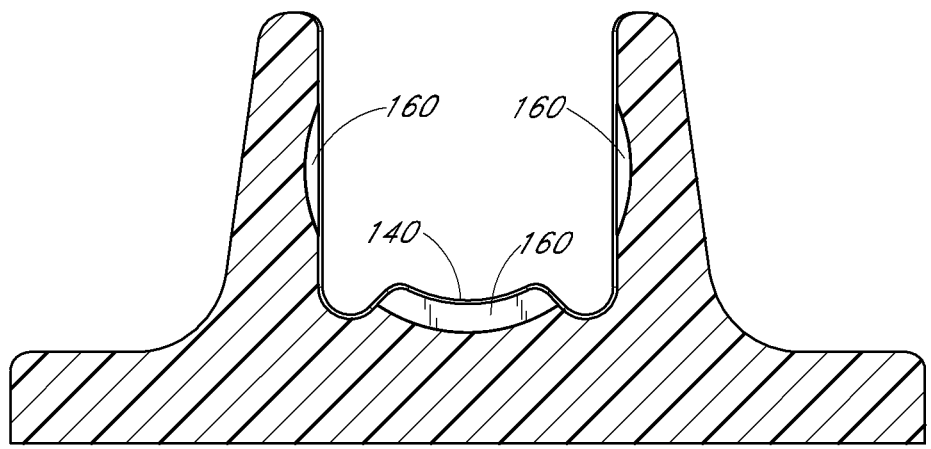
FIG. 11 is a cross-sectional view of the retainer of FIG. 3, taken along the 11-11 line.
Figure 12:
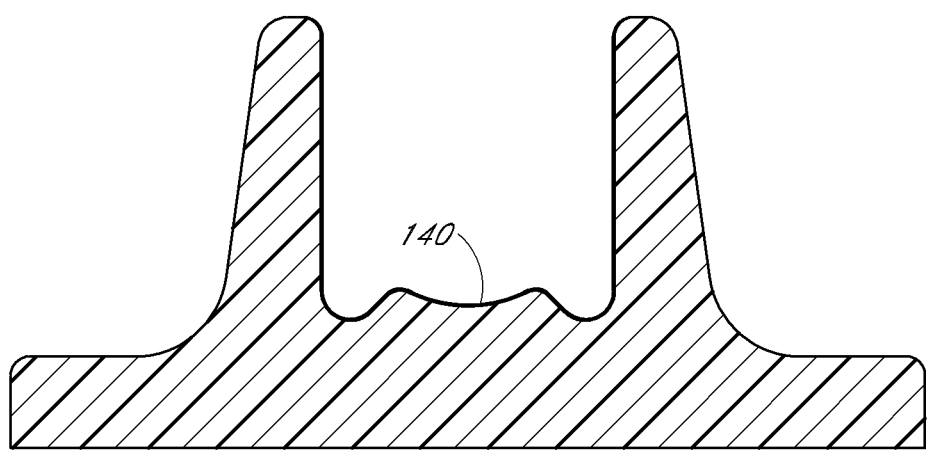
FIG. 12 is a cross-sectional view of the retainer of FIG. 3, taken along the 12-12 line.

As best seen in FIGS. 11 and 12, the upper side surfaces of the walls 170 preferably are rounded or chamfered and slope toward the channel opening 150 to guide the catheter hub 10 and the splines 40 into the channel 130. As a result, the catheter hub 10 slides more smoothly over the upper side surfaces and into the channel 130 as the walls 170 are deflected outwardly by the interference with the splines 40 of the catheter hub during the insertion process. Alternatively, the catheter hub 10 may be slid in a proximal direction along the longitudinal axis and into the channel 130. In this way, the walls 170 need not deflect outwardly as the catheter hub 10 is inserted into the retainer 120 since the first diameter 30(a) and splines 40 enter the grooves 210, 220, respectively, on the distal portion 200 of the retainer.

The walls 170 preferably wrap around a sufficient amount of the catheter hub 10 to inhibit unintentional transverse movement of the catheter hub 10 relative to the retainer 120. As understood from the above description, the upper ends of the walls 170 are disposed inward from the concave surfaces of the grooves 210 to narrow the lateral width of the channel opening 150 above the grooves 210. The extent to which the upper ends can be disposed inward is limited, however, in order to permit insertion of the splines 40 into the channel 130 through the opening 150. Accordingly, the grooves 210 preferably have a length sufficient to produce the desired retention strength to hold the catheter hub 10 in the retainer 120 against an upwardly directed force (or force component). Of course, where the retainer 120 includes one or more additional mechanisms to resist transverse movement of the catheter hub 10 relative to the retainer 120—for example, covering at least a portion of the inner channel surface with an adhesive or overlying the secured catheter hub 10 and retainer 120 with an adhesive cover—the length of the grooves 210 can be reduced.

In a preferred mode, the walls 170 also have a sufficient length to prevent the catheter hub 10 from yawing (i.e., movement side to side in a longitudinal-lateral plane). That is, the length of the walls 170, which interacts with the tubular body 30, is sufficient so that the first diameter 30(a) portion does not act as a fulcrum. However, while such wall length is preferred, the wall length can be significantly shorter (e.g., interact with the catheter hub at a single longitudinal point) where the catheter hub is also held near its proximal end by the walls 170.

As best seen in FIG. 12, each wall 170 adjacent to the groove 210 has a lateral thickness that decreases from the base surface 140 of the retainer 120 to the top of the retainer 120. The decreased lateral thickness of the walls 170 provides increased flexibility to permit the walls 170 to deflect elastically outwardly when pressing the catheter hub 10 into the channel 130.

The distal ends of the side walls 170 define at least a portion of the distal-most abutment surfaces 180. In the illustrated embodiment, the distal-most abutment surfaces 180 are generally upright.

Figure 13:
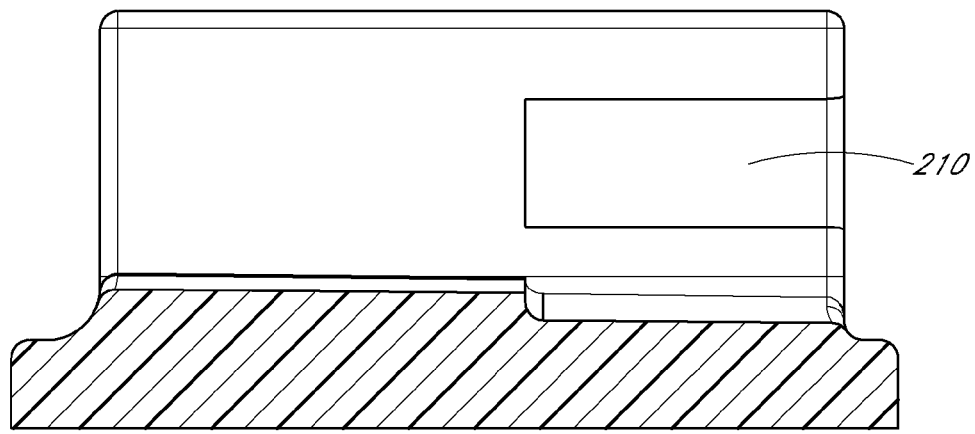
FIG. 13 is a cross-sectional view of the retainer of FIG. 3, taken along the 13-13 line.

As seen in FIGS. 2, 10, and 13, the lower groove 210 is defined in the retainer 120 from the distal end portion 200 towards the proximal end portion 190 and between the walls 170, and extends into the base surface 140. The longitudinal length of the groove 210 in the base surface 140 preferably matches the longitudinal lengths of the grooves 210 in the walls 170. In the illustrated embodiment, the groove 210 in the base surface 140 is deep enough to receive a portion of the first diameter 30(a) of the tubular body 30.

As seen in FIGS. 2, 9, 12, and 13, at the intersections of the walls 170 and the base surface 140 are a pair of grooves 220 defined in the retainer 120 which extend from the distal end portion 200 to the proximal end portion 190. The longitudinal length of the grooves 220 in the base surface 140 preferably extends for the entire length of the channel 130. In the illustrated embodiment, the grooves 220 in the base surface 140 are deep enough to receive one or more of the splines 40 that may extend downward when the catheter hub 10 is inserted into the retainer 120. Portions of the grooves 220 open into the groove 210 at their lateral inward sides.

As is illustrated in FIG. 12, the cross-section of the channel 130 near the proximal end portion 190 generally has a U-shaped cross-section with a radius of curvature at least as large as the radius of the second diameter 30(b) portion of the tubular body 30. The radius of curvature can be larger than the radius of the second diameter 30(b) to facilitate securement.

Figure 5:
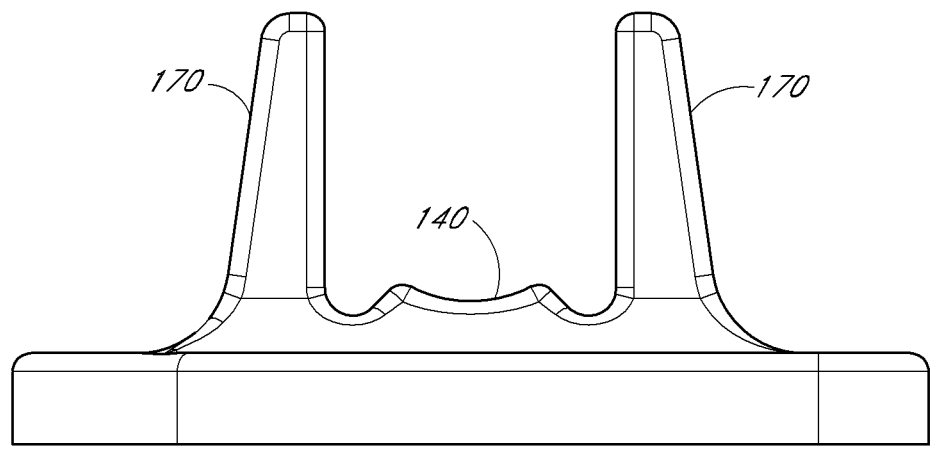
FIG. 5 is a front side view of the retainer of FIG. 3.

Both the proximal opening as illustrated in FIG. 5 and the proximal portion 190 of the channel 130 have generally U-shapes; however, one or both of these channel sections can have a truncated, generally circular shape. In this variation, the opening or the proximal channel section can receive the second diameter 30(b) portion of the catheter hub 10 in a snap fit manner, similar to the distal end portion 200 of the retainer 120, to inhibit further transverse movement of the catheter hub 10 relative to the retainer 120.

As illustrated in FIGS. 7 and 8, the retainer 120 includes finger platforms 230 on both sides of the central channel 130. Each finger platform 230 extends laterally from one side of the retainer 120. Each finger platform 230 may have a ribbed upper surface to improve frictional contact between a healthcare provider's fingers and the platform 230. The finger platforms 230 are sized and configured to allow a healthcare provider to press the retainer 120 against the skin of the patient while pulling up on the catheter hub 10 when disengaging the catheter hub 10 from the retainer 120. Alternatively, the healthcare provider may use the platforms 230 to resist movement of the retainer 120 when disengaging the catheter hub 10 from the retainer 120 by sliding the catheter hub 10 in a distal direction.

The retainer 120 is made of relatively stiff plastic material (e.g., polycarbonate), but is somewhat flexible such that the catheter hub 10 will force the walls 170 outwardly when a healthcare provider presses the catheter hub 10 into the central channel 130 of the retainer 120. When the tubular body 30 sits in the central channel 130, the upper edges of the walls 170 snap inwardly to their original position to securely hold the catheter hub 10 within the retainer 120.

The retainer 120 may be constructed in any of a variety of ways which will be well known to one of skill in the art. For instance, retainer 120 may be integrally molded such as by injection molding or by thermoplasty. The retainer 120 preferably comprises a durably, flexible material, and more preferably comprise a generally inert, non-toxic material. Suitable materials include plastics, polymers, or composites such as polypropylene, polyethylene, polycarbonate, polyvinyl-chloride, polyurethane, tetrafluoroethylene (e.g., TEFLON®), polytetrafluoroethylene (a.k.a., PTEF), acetal resin (e.g., DELRIN®), chlorotrifluoroethylene (e.g., KEL-F®), acrylonitrile butadiene styrene, styrene butadiene, nylon, olefin, acrylic, polyester, moldable silicon, thermoplastic urethane, thermoplastic elastomers, thermoset plastics and the like. The retainer 120 can be formed by injection molding using a polycarbonate, available commercially from GE Plastics (See www.geplastics.com). However, other materials can be used.

Anchor Pad

As is seen in FIG. 1, the anchor pad 110 is a substantially flat piece of material with transversely opposing sides. The lower side of the pad 110 faces toward the skin of the patient, and is preferably covered with an adhesive surface suitable for attaching the anchor pad 110 to the skin of the patient. The entire surface, however, need not be covered. An upper side of the anchor pad 110 faces away from the skin of the patient and supports the retainer 120.

The anchor pad 110 may comprise a laminate structure with an upper foam layer (e.g., closed-cell polyethylene foam) and a lower adhesive layer. Such foam with an adhesive layer is available commercially from Tyco Adhesives of Norwood, Mass. The lower adhesive layer constitutes the lower surface of the anchor pad 110, i.e., it is coextensive with the upper foam layer. The lower surface desirably is a medical-grade adhesive and can be either diaphoretic or nondiaphoretic, depending upon the particular application. The adhesive may be a Hydrocolloid and Zinc Oxide adhesive. Such an adhesive may provide additional advantages in humid environments, such as typically found in neonatal intensive care unit.

A surface of the upper foam layer constitutes the upper surface of the anchor pad 110. The upper surface can be roughened by chemical priming or by corona-treating the foam with a low electric charge. The roughened or porous upper surface can improve the quality of the adhesive joint (which is described below) between the retainer 120 and the anchor pad 110. In the alternative, the flexible anchor pad 110 can comprise a medical-grade adhesive lower layer, an inner foam layer and an upper paper or other woven or non-woven cloth layer.

Figure 31:
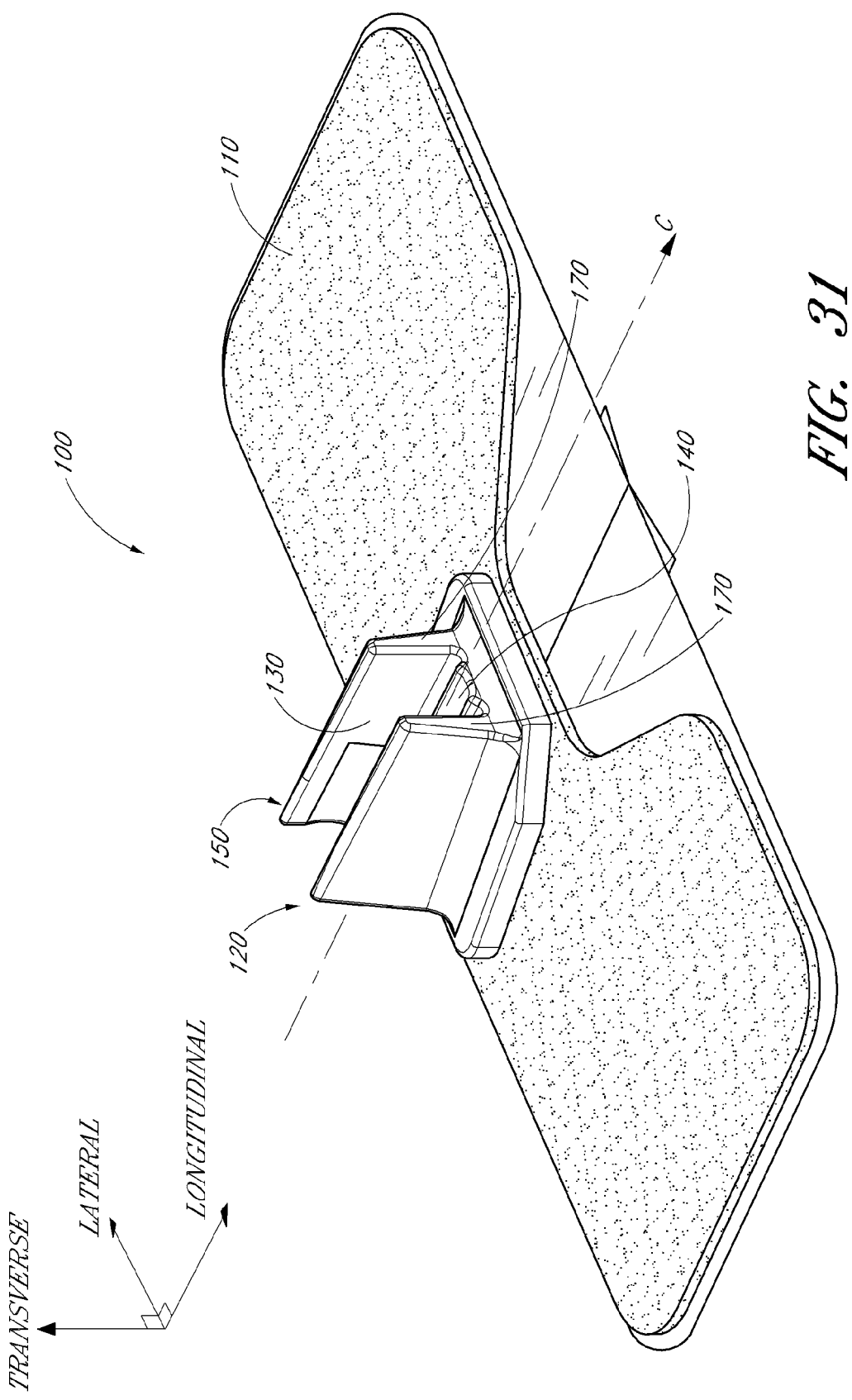
FIG. 31 is a perspective view of the securement device configured in accordance with another preferred embodiment of the present invention that includes an incident angle of approximately seven degrees.
Figure 32:
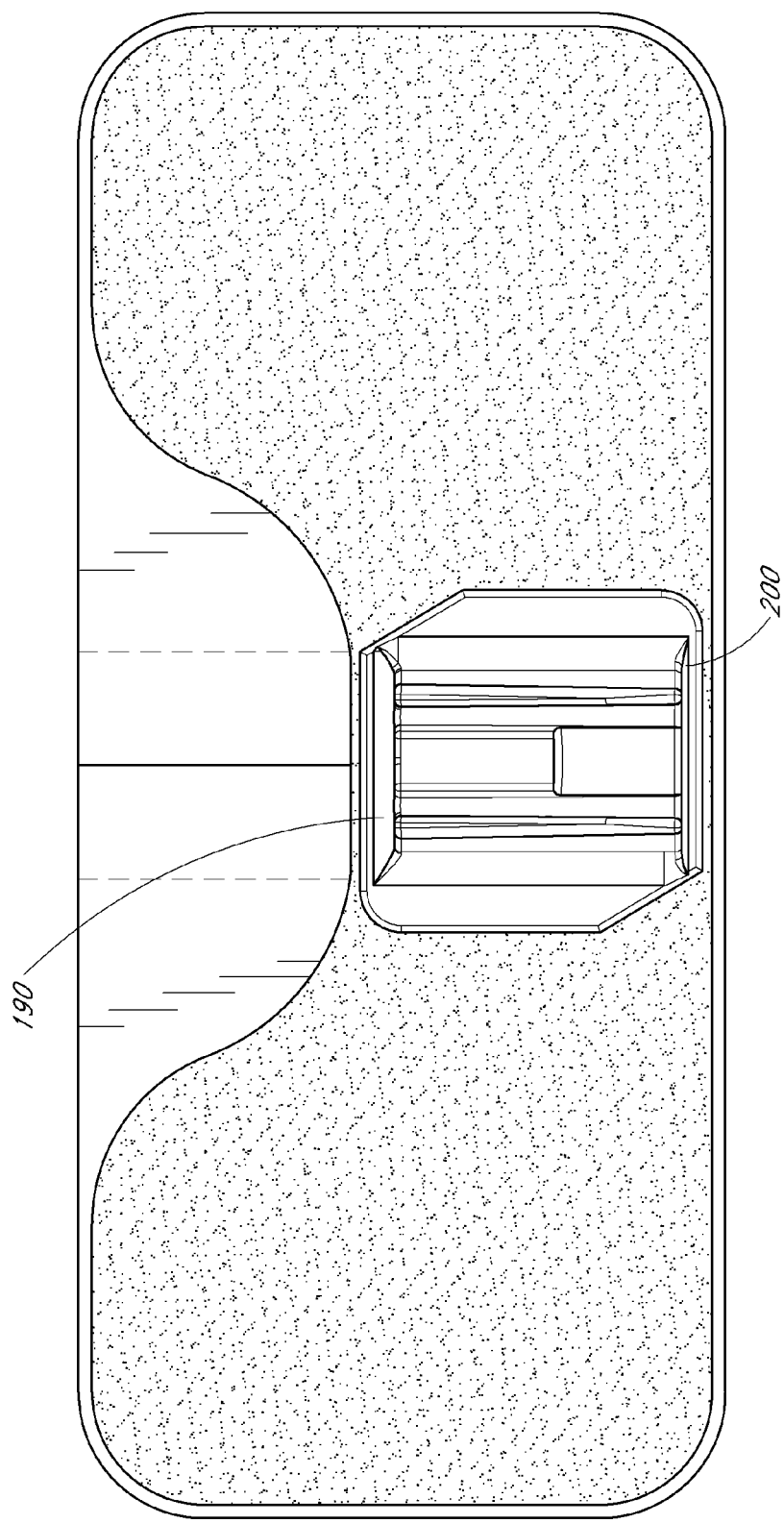
FIG. 32 is a top plan view of the retainer and anchor pad of FIG. 31.
Figure 33:
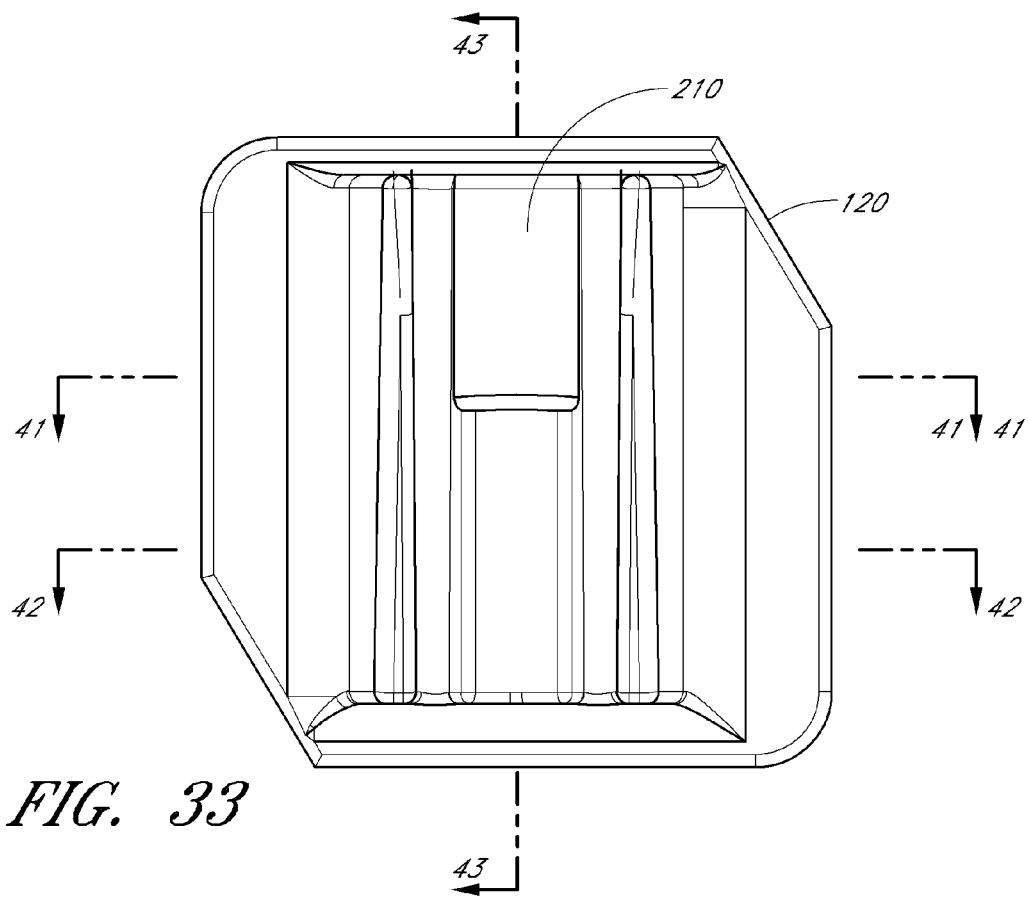
FIG. 33 is a top plan view of the retainer of FIG. 32.
Figure 34:
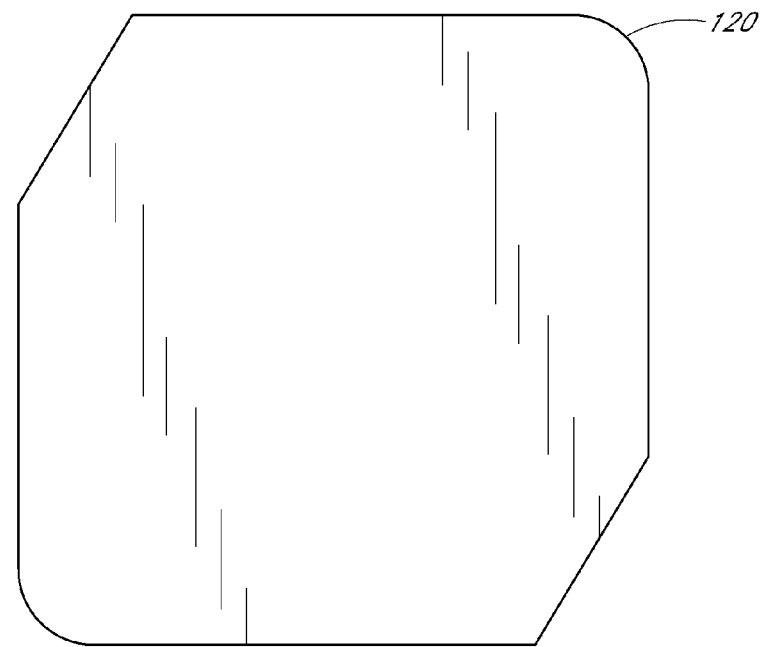
FIG. 34 is a bottom view of the retainer of FIG. 33.
Figure 35:
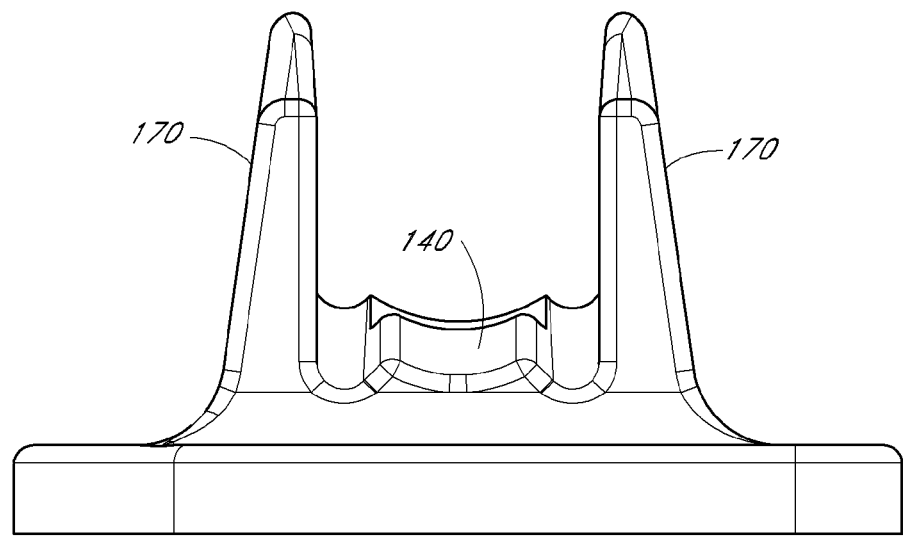
FIG. 35 is a front side view of the retainer of FIG. 33.
Figure 36:
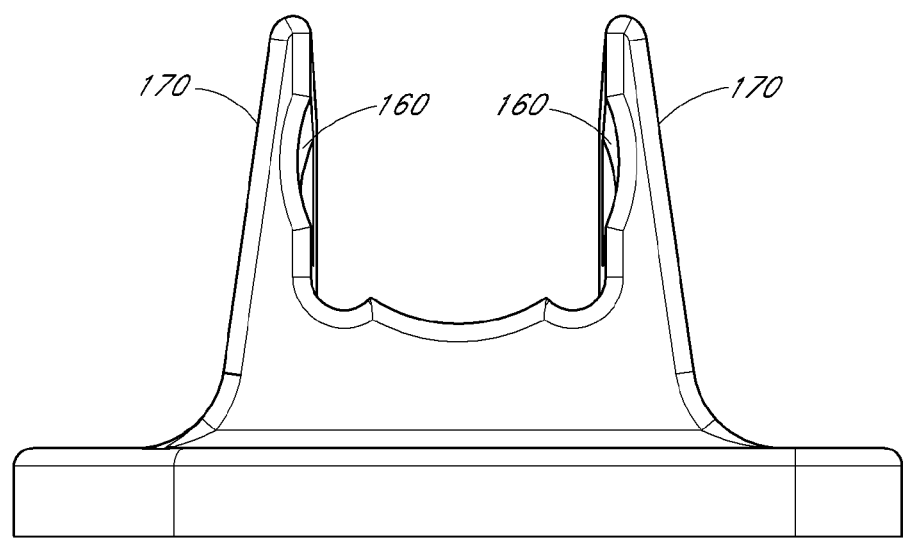
FIG. 36 is a rear side view of the retainer of FIG. 33.
Figure 37:
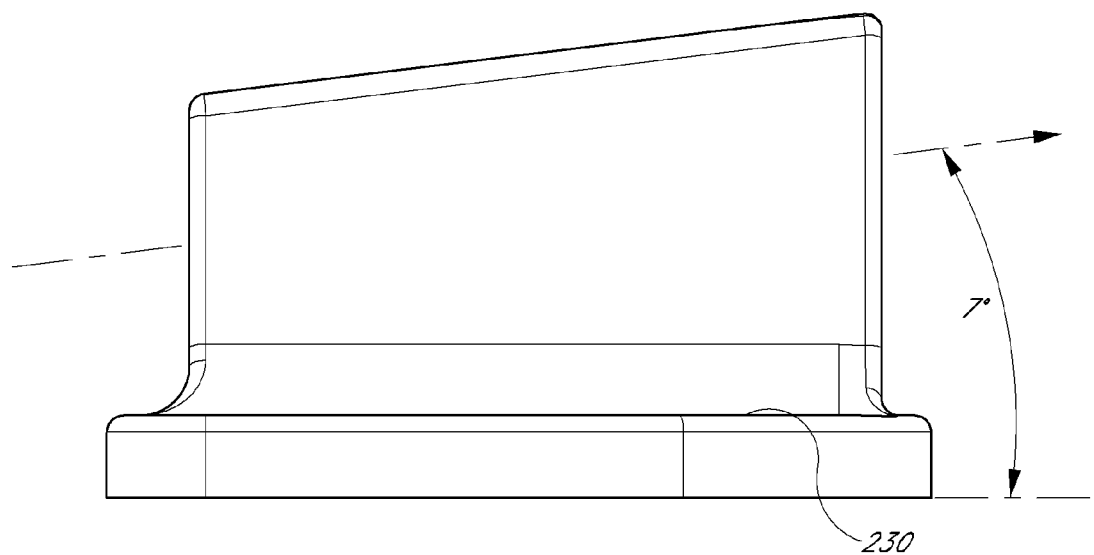
FIG. 37 is a side view of the retainer of FIG. 33.
Figure 38:
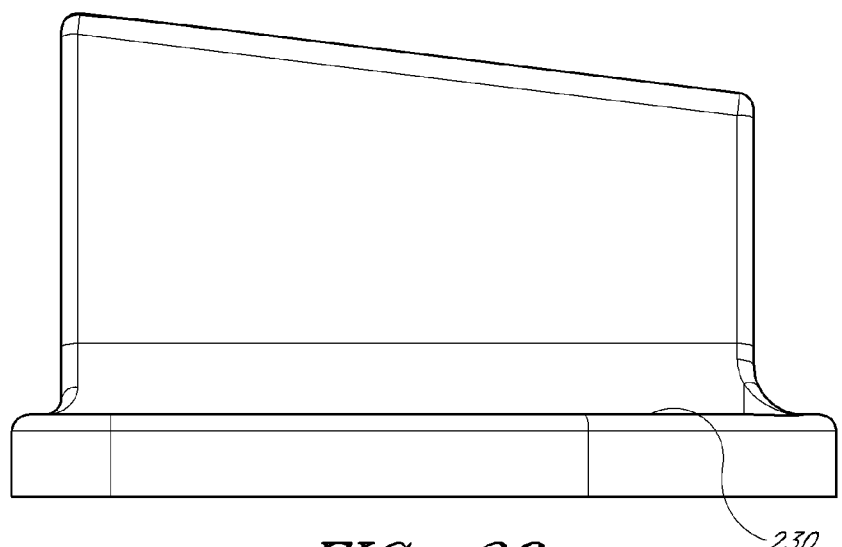
FIG. 38 is an opposite side view of the retainer of FIG. 33.
Figure 39:
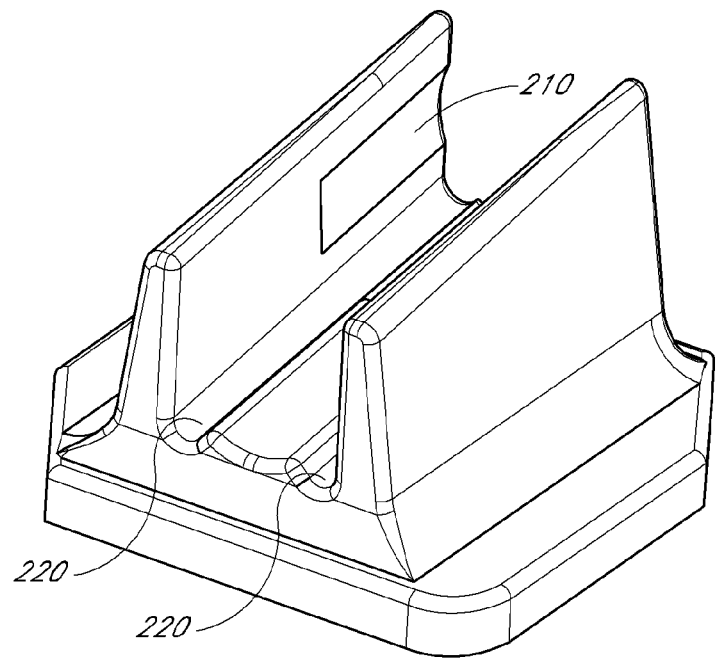
FIG. 39 is a front perspective view of the retainer of FIG. 33.
Figure 40:
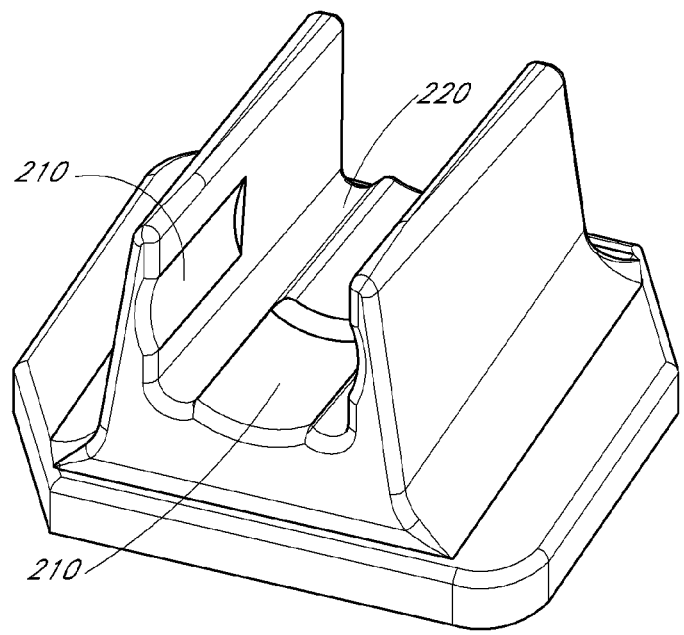
FIG. 40 is a rear perspective view of the retainer of FIG. 33.
Figure 41:
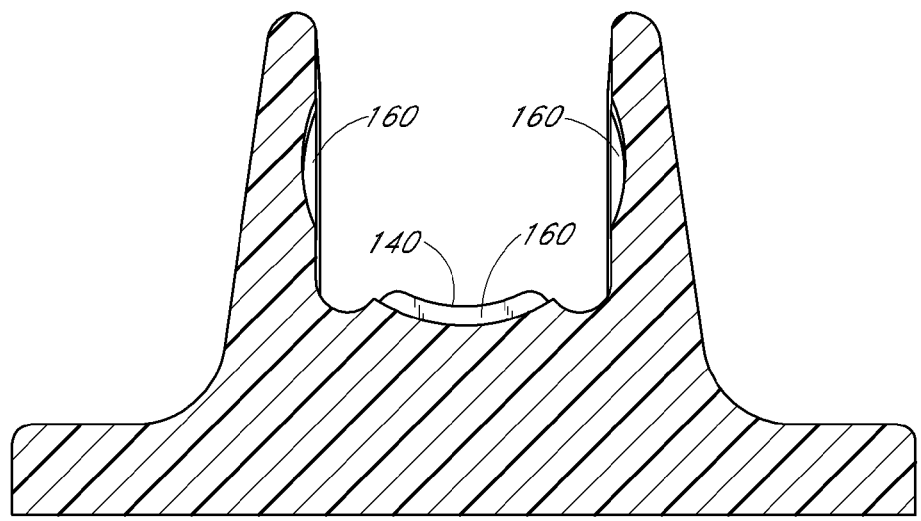
FIG. 41 is a cross-sectional view of the retainer of FIG. 33, taken along the 41-41 line.
Figure 42:
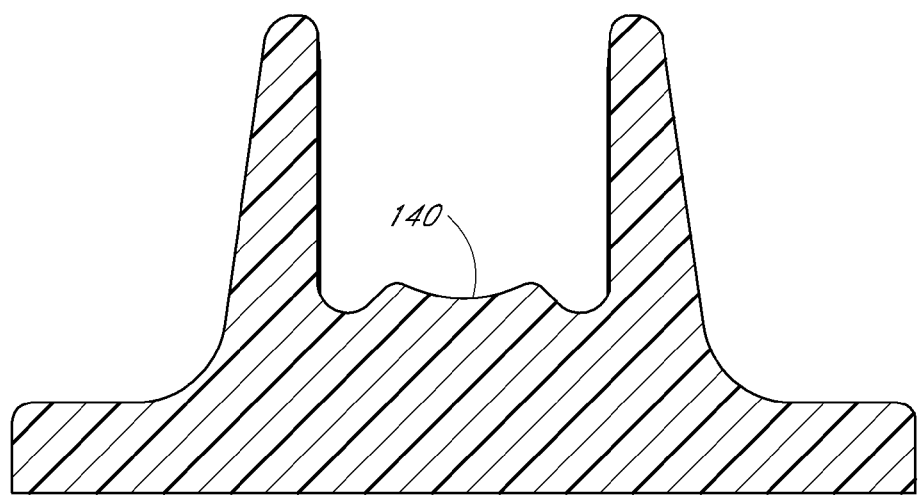
FIG. 42 is a cross-sectional view of the retainer of FIG. 33, taken along the 42-42 line.
Figure 43:
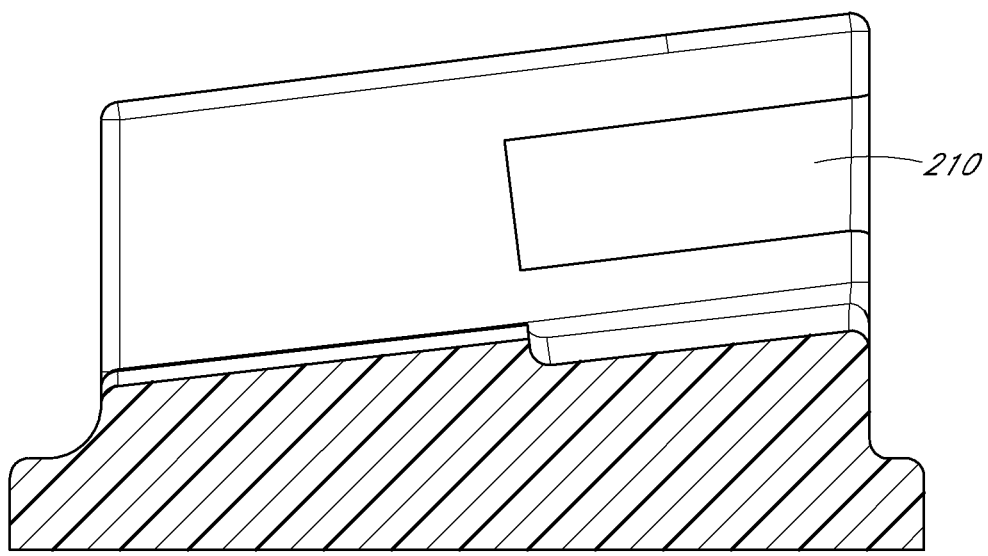
FIG. 43 is a cross-sectional view of the retainer of FIG. 33, taken along the 28-28 line.
Figure 44:
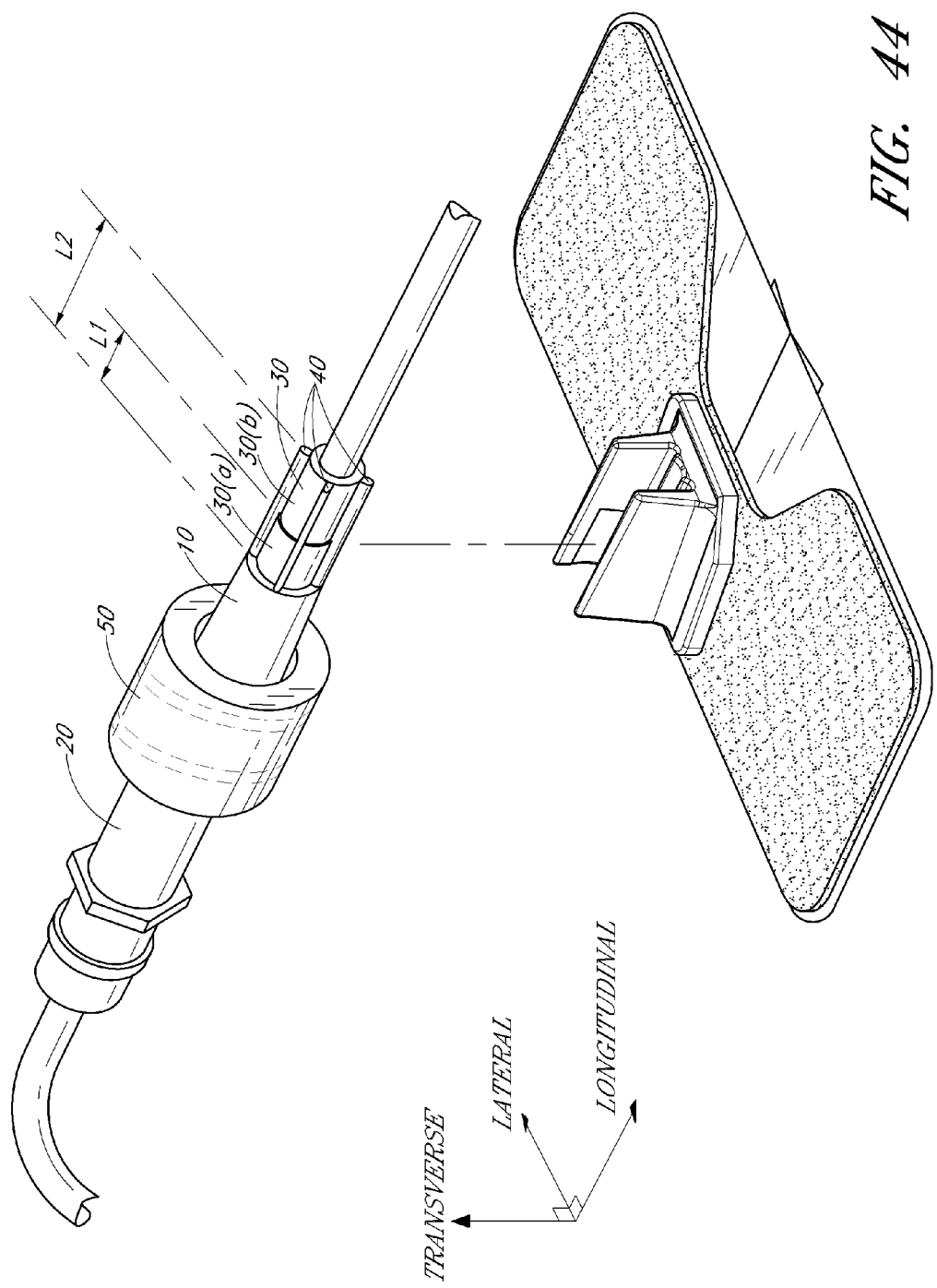
FIG. 44 is a perspective view of a catheter hub arranged above the retainer of the securement device from FIG. 31.
Figure 45:
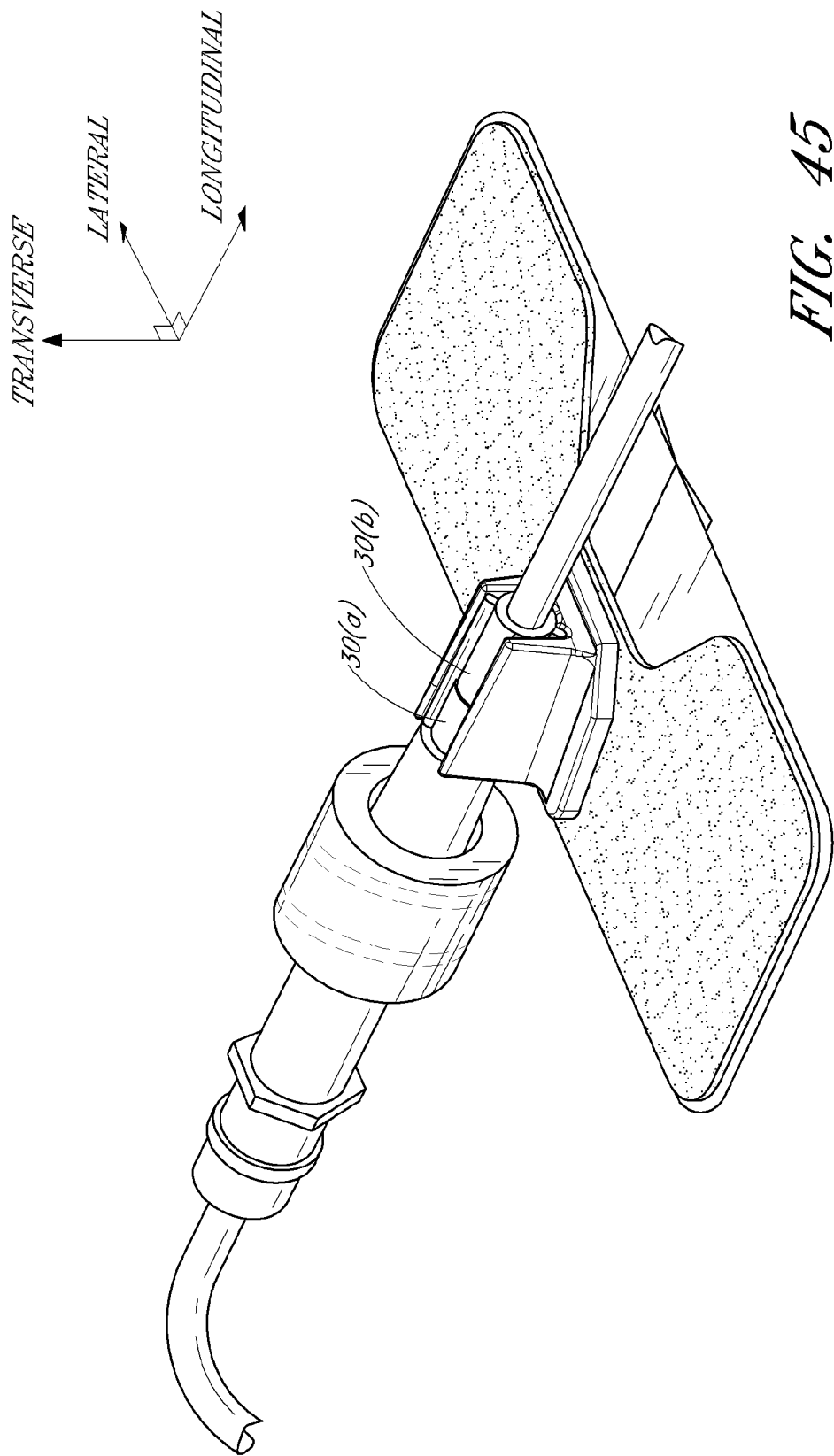
FIG. 45 is a perspective view of the catheter hub secured to the retainer of the securement device from FIG. 31.
Figure 46:
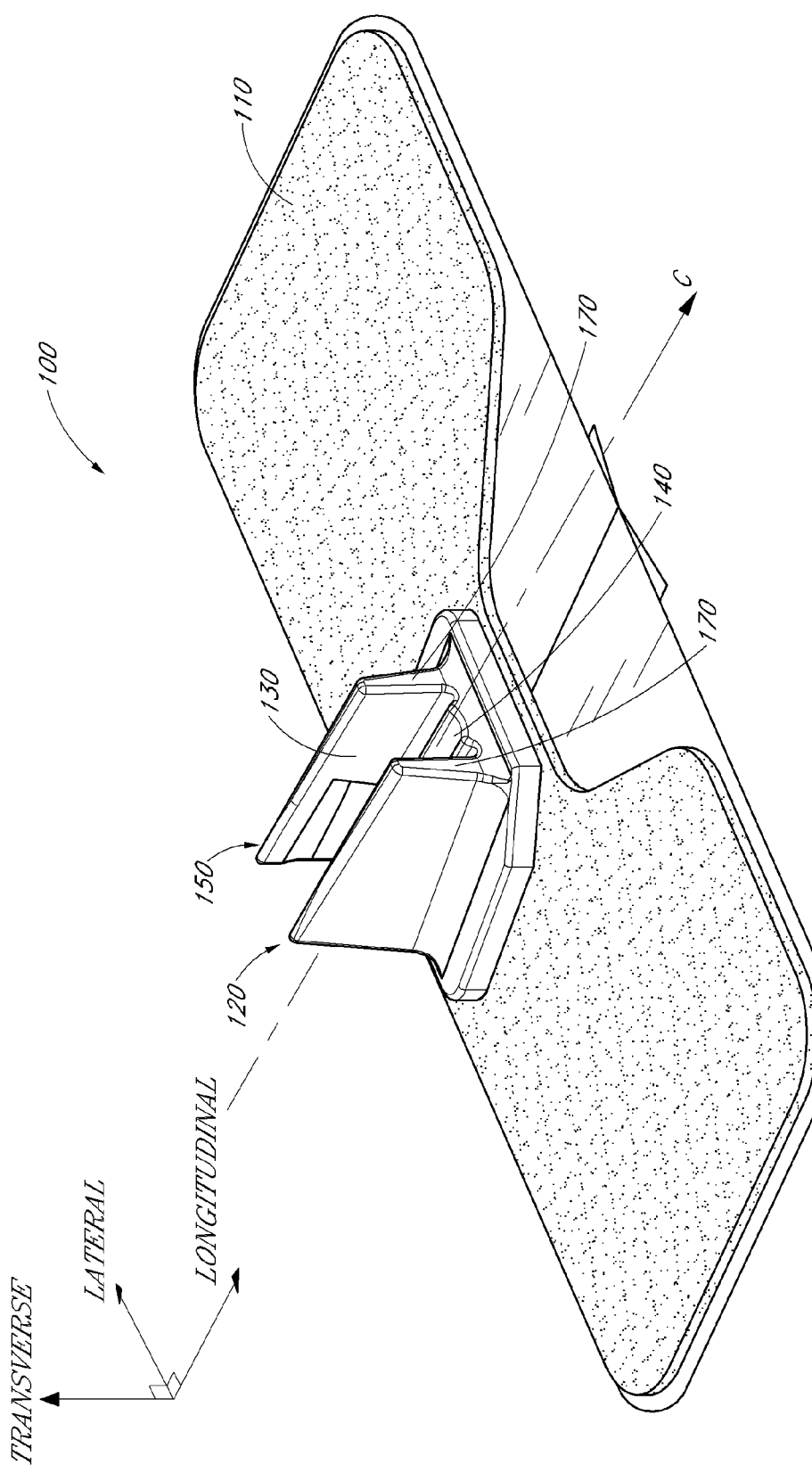
FIG. 46 is a perspective view of the securement device configured in accordance with another preferred embodiment of the present invention that includes an adhesive spot and an incident angle of approximately seven degrees.
Figure 47:
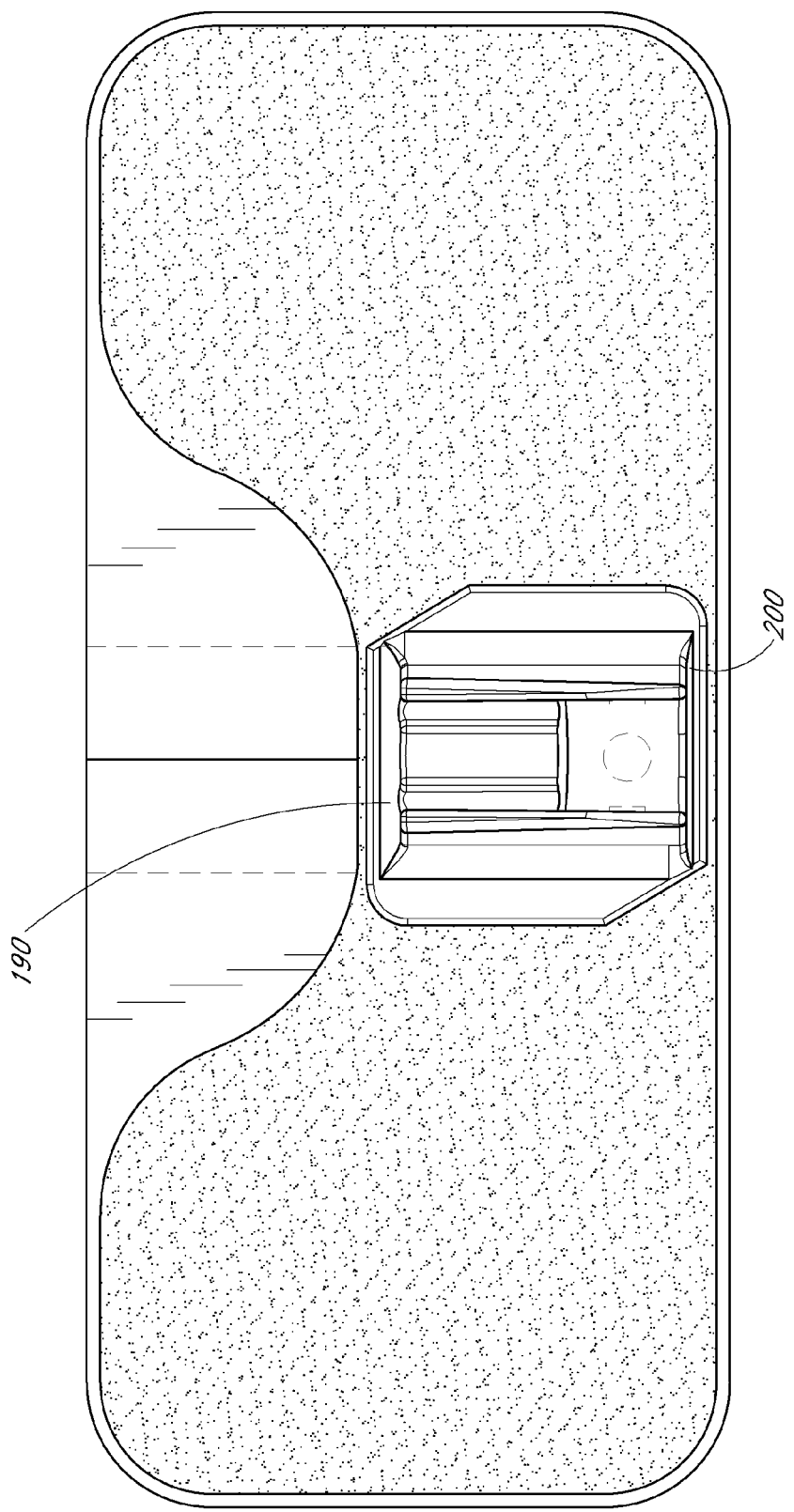
FIG. 47 is a top plan view of the retainer and anchor pad of FIG. 46.
Figure 48:
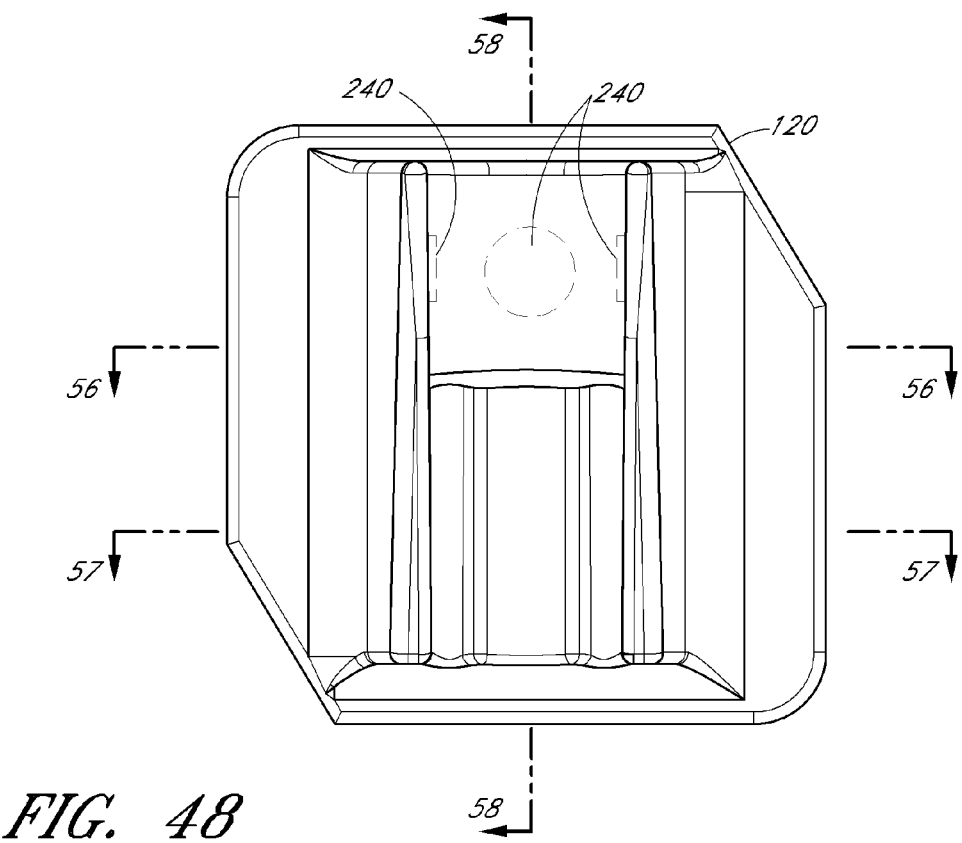
FIG. 48 is a top plan view of the retainer of FIG. 47.
Figure 49:
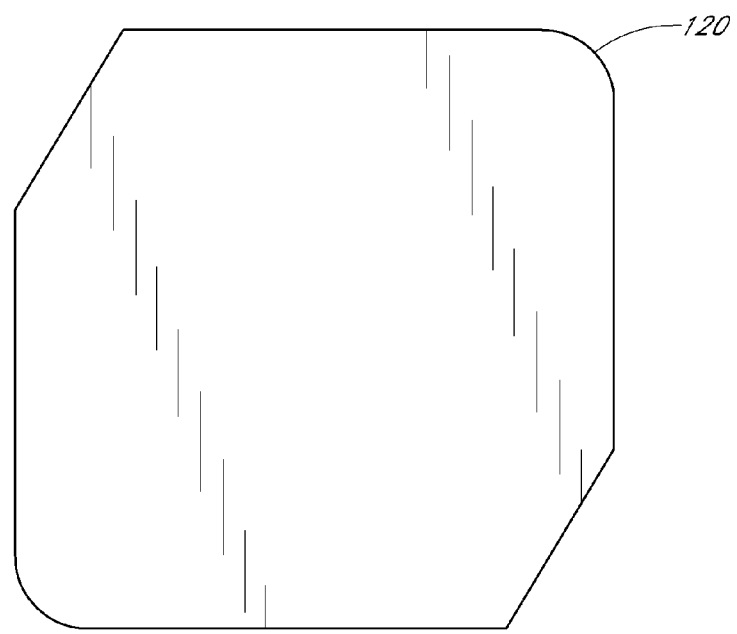
FIG. 49 is a bottom view of the retainer of FIG. 48.
Figure 50:
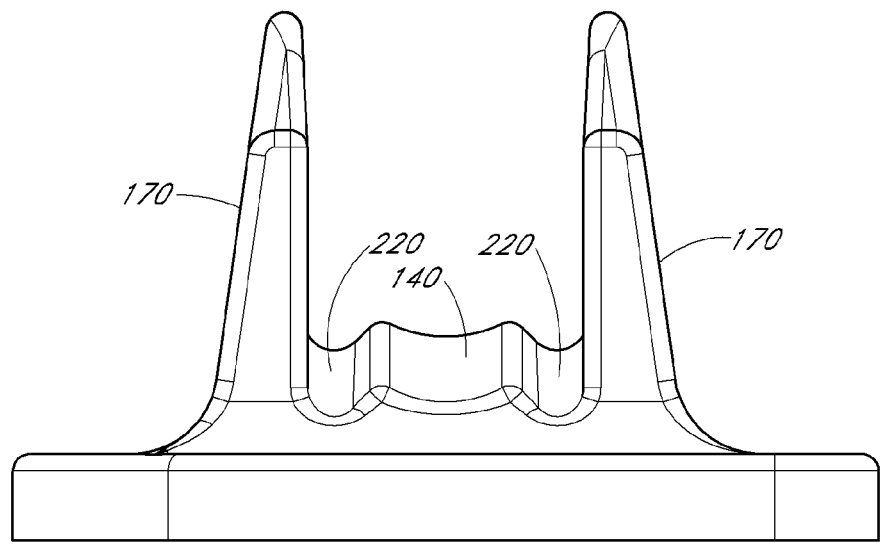
FIG. 50 is a front side view of the retainer of FIG. 48.
Figure 51:
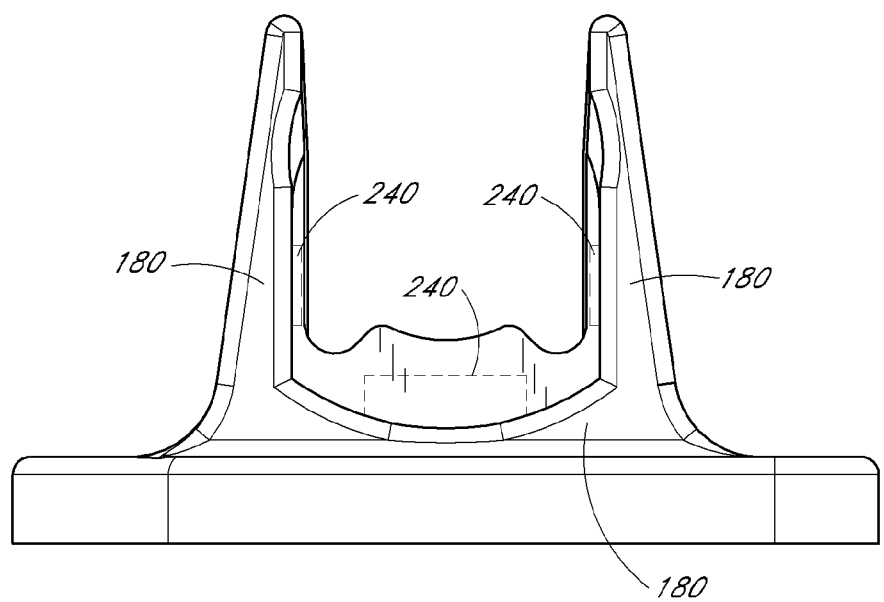
FIG. 51 is a rear side view of the retainer of FIG. 48.
Figure 52:
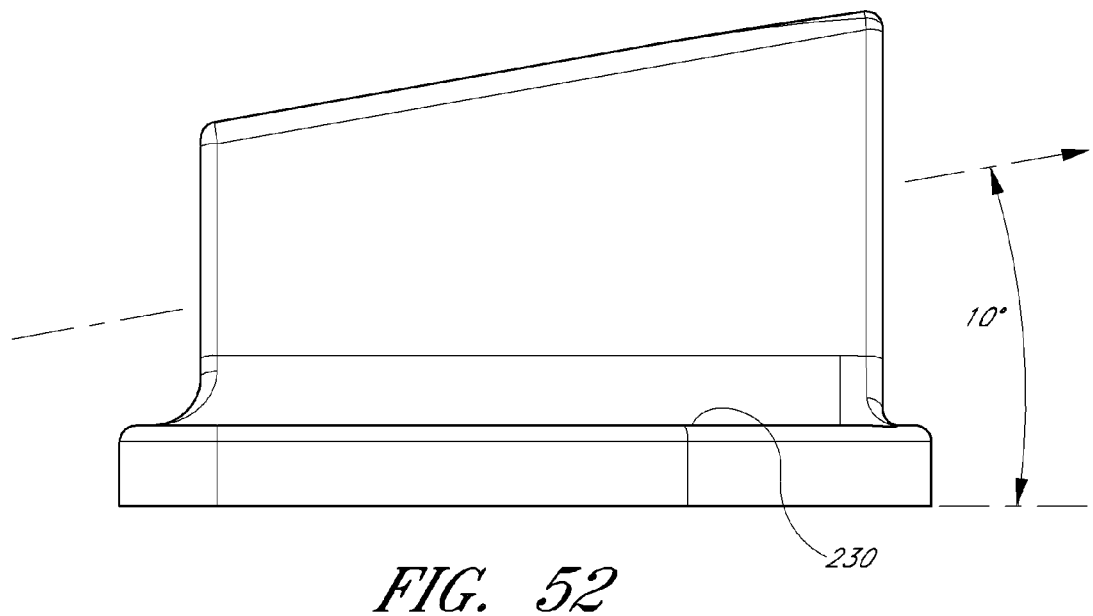
FIG. 52 is a side view of the retainer of FIG. 48.
Figure 53:
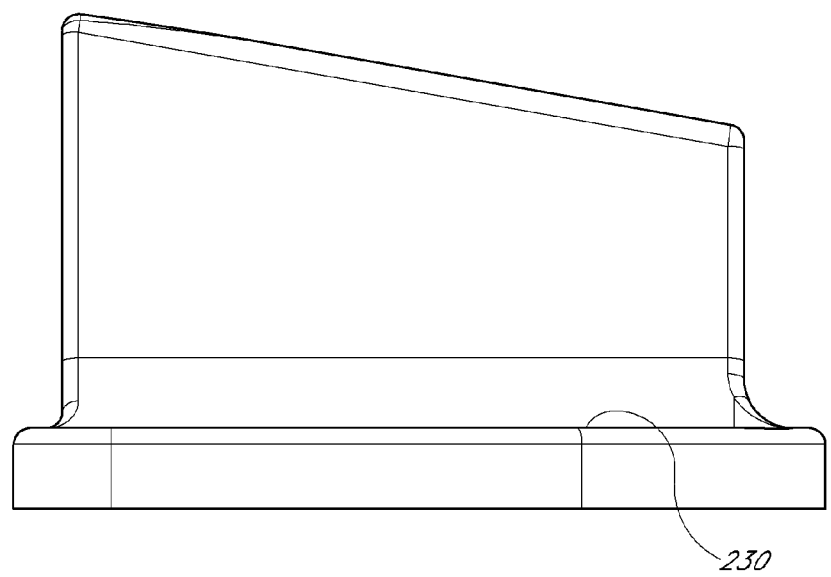
FIG. 53 is an opposite side view of the retainer of FIG. 48.
Figure 54:
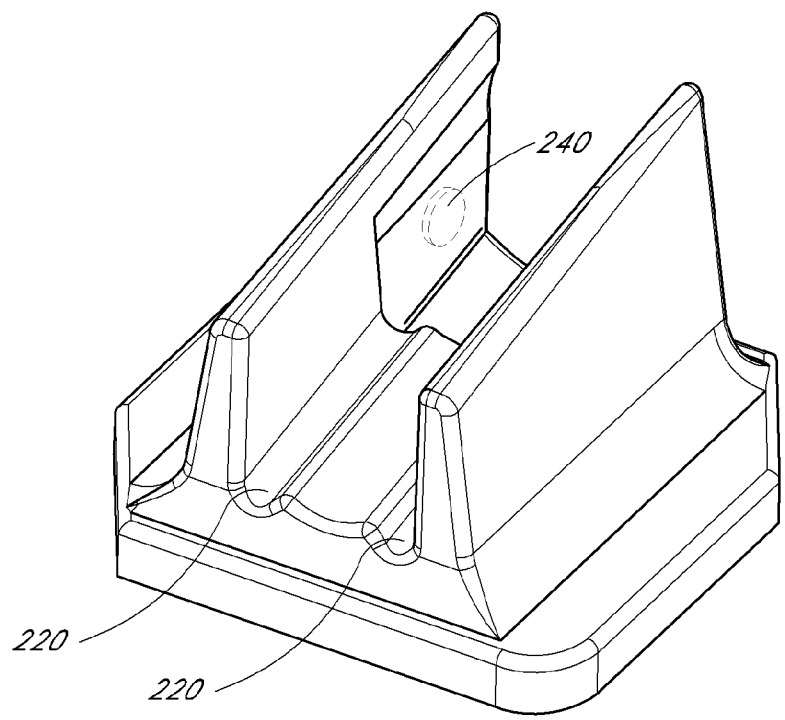
FIG. 54 is a front perspective view of the retainer of FIG. 48.

The anchor pad 110 generally has a rectangular shape with rounded corners. In the embodiment illustrated in FIG. 31, the anchor pad further includes elongated extensions that project from the generally rectangular shape in a proximal direction. The elongated sections form a concave section or notch, as shown in FIG. 31, that narrows the center of the anchor pad 110 proximate to the retainer 120 and on a proximal side of the pad 110. The notch facilitates viewing the indwelling catheter, cleansing the insertion site, and placing the anchor pad 110 about the insertion site. This shape also permits the anchor pad 110 to be placed on the patient such that the anchor pad extends beyond the insertion site in the proximal direction, and away from the insertion site in the lateral direction. By aligning the anchor pad 110 and the insertion site of the catheter in this manner, enhanced stability is provided to the catheter. This also minimizes the free length of the catheter between the insertion site and the channel 130 of the retainer 120, helping prevent inadvertently catching or pulling on and dislodging of the catheter as the patient moves or as healthcare providers tend to the patient. A smaller anchor pad 110, such as is illustrated in FIG. 1, may be preferred where the receiving surface on the patient is small such as on a child or baby.

The retainer 120 is preferably centered upon the anchor pad 110. Consequently the lateral sides of the anchor pad 110 have more contact area with the skin, both distally and proximally of the retainer 120 in the longitudinal direction, which provides greater stability and adhesion to the skin while still permitting the retainer 120 to be located near the insertion site. Although not illustrated, the anchor pad 110 also can include suture and/or breather holes which are positioned to the sides of the retainer 120.

The retainer base is attached to the upper surface of the anchor pad 110. The bottom surface preferably is secured to the upper surface by a solvent bond adhesive, such as cyanoacrylate or other bonding material. One such adhesive is available commercially from 3M.

A removable paper or plastic release liner desirably covers the adhesive lower surface before use. The release liner preferably resists tearing and desirably is divided into a plurality of pieces to ease attachment of the anchor pad 110 to a patient's skin. In the illustrated embodiment, the release liner is split along a centerline of the anchor pad 110 in order to expose only half of the adhesive lower surface at one time.

Figure 71:
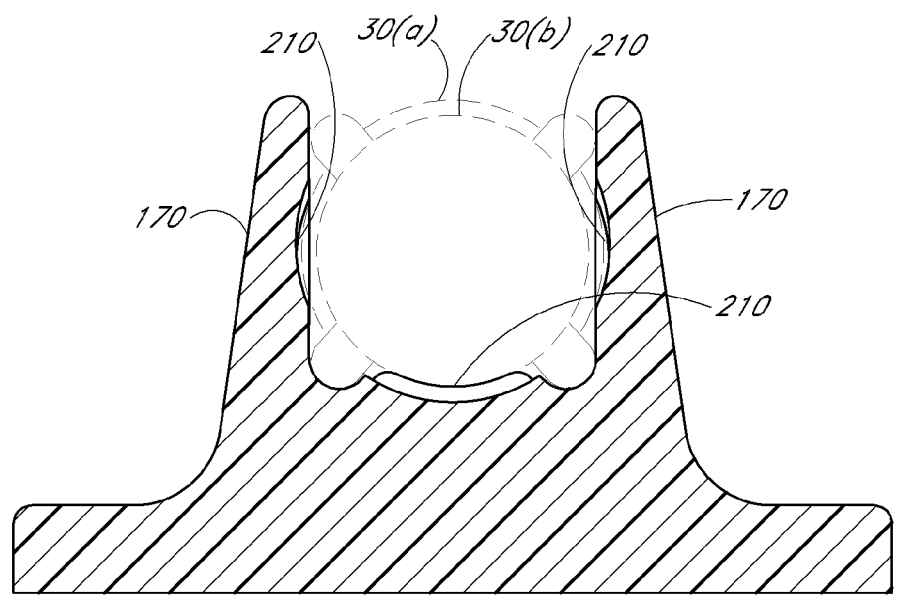
FIG. 71 is a cross-sectional view of the catheter hub from FIG. 74 secured within the retainer of FIG. 63, taken along the 71-71 line.
Figure 72:
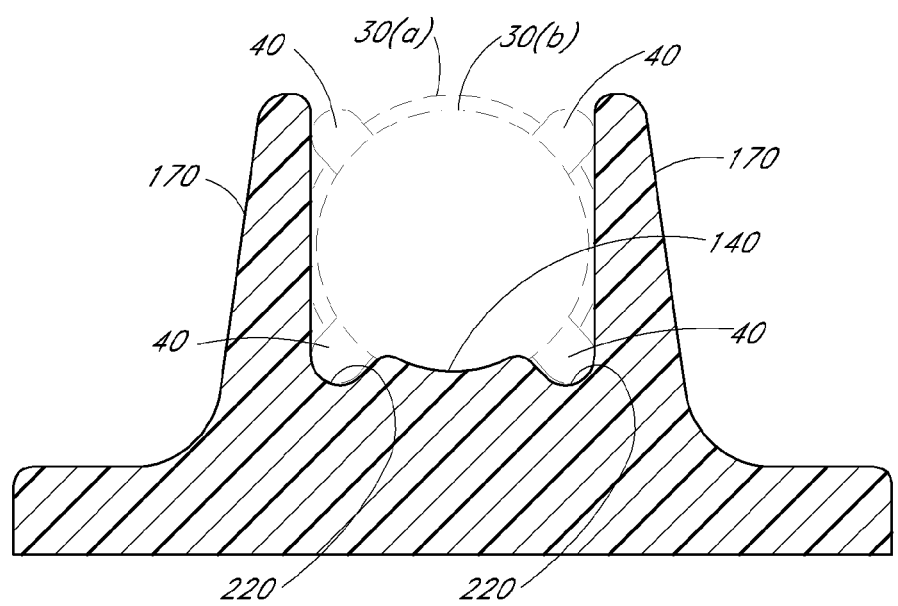
FIG. 72 is a cross-sectional view of the catheter hub from FIG. 74 secured within the retainer of FIG. 63, taken along the 72-72 line.
Figure 73:
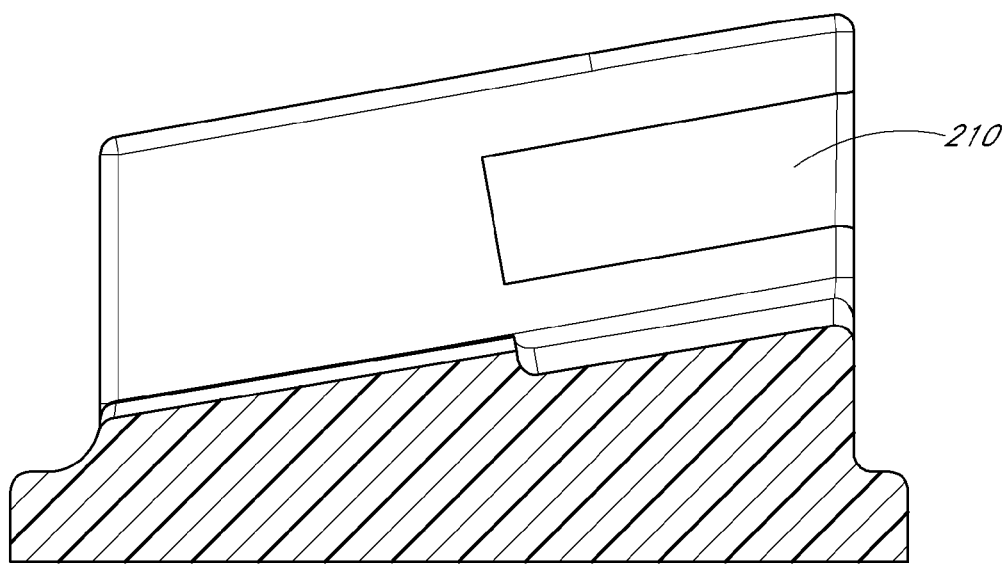
FIG. 73 is a cross-sectional view of the retainer of FIG. 63, taken along the 73-73 line.
Figure 74:
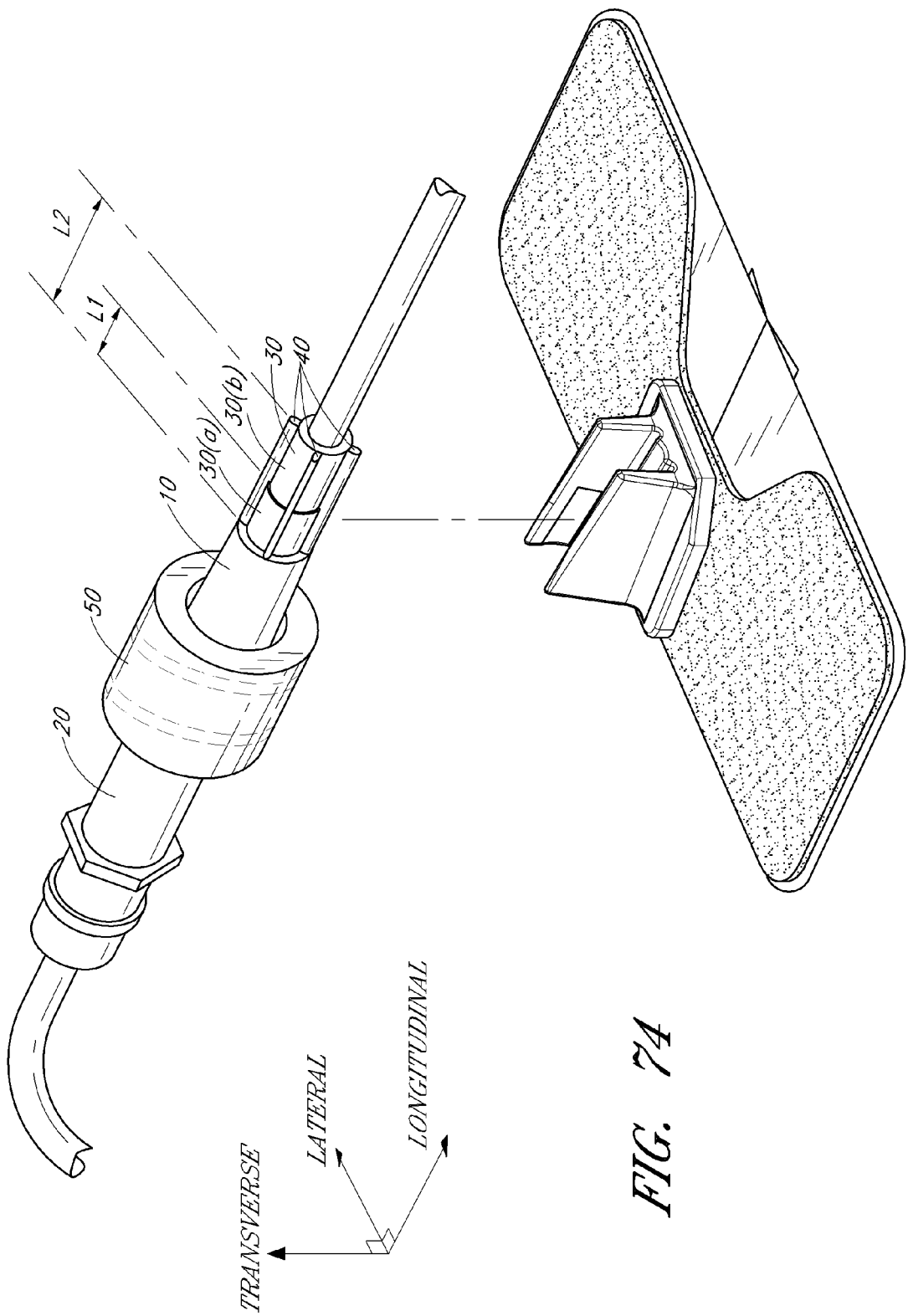
FIG. 74 is a perspective view of a catheter hub arranged above the retainer of the securement device from FIG. 61.
Figure 75:
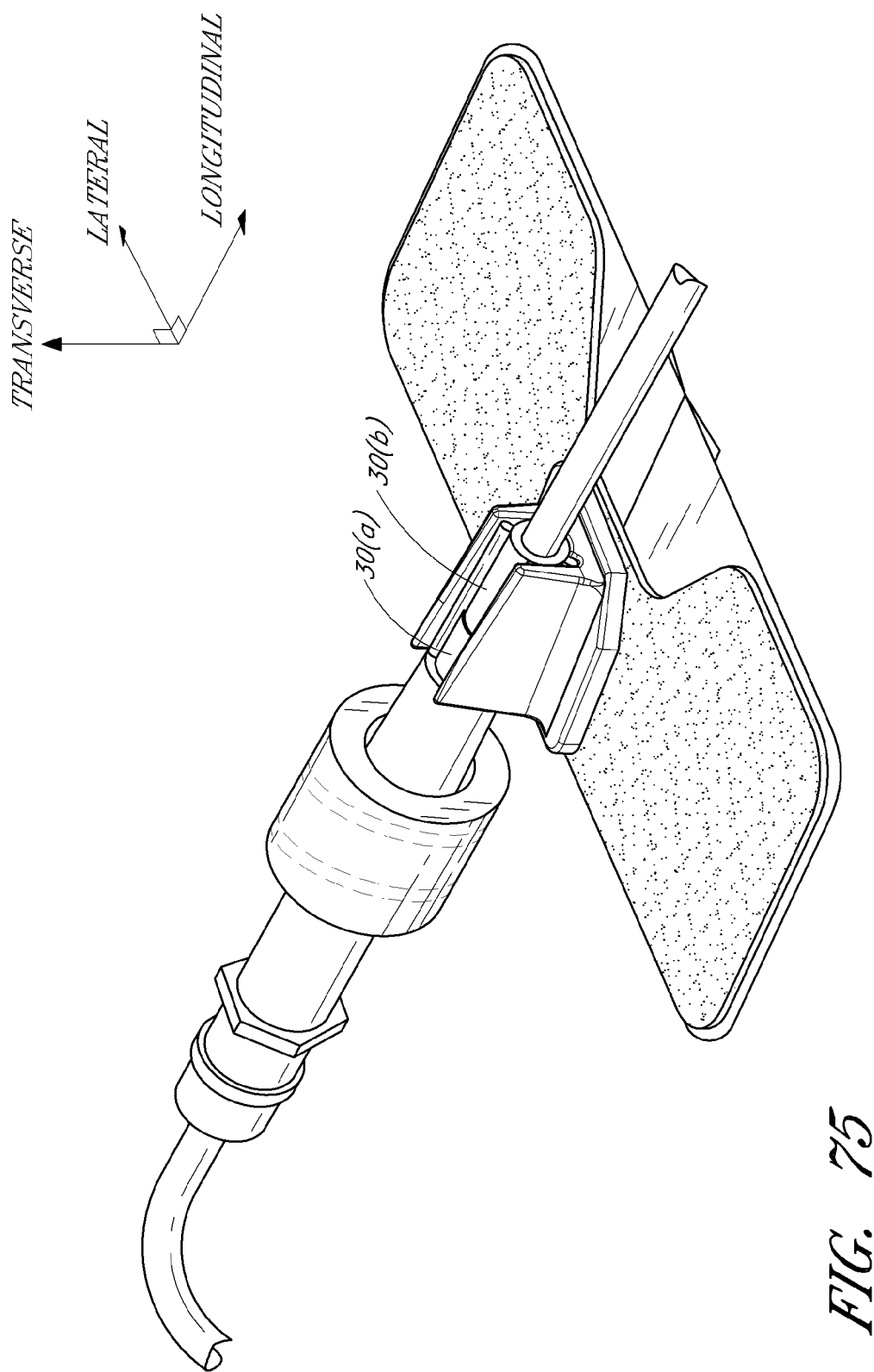
FIG. 75 is a perspective view of the catheter hub secured to the retainer of the securement device from FIG. 61.

As understood from the above description of the securement system 100 shown in FIG. 1, the retainer 120 cooperates with a catheter hub 10 that securely connect a connector fitting having a fluid tube (e.g., a fluid supply line) to an indwelling catheter. The cooperation between abutment surfaces on the retainer 120 and the contact surfaces on the catheter hub maintains the catheter in the desired indwelling position. As is illustrated, for example in FIGS. 71 and 72, these abutment surfaces can include, for example, distal-most abutment surfaces 180 and intermediate surfaces 160. The intermediate surfaces 160 lie between the proximal and distal ends and are defined on the walls 170 and the base surface 140. The distal and intermediate abutment surfaces 180, 160 preferably are separated by a distance that is generally equal to the longitudinal length $L_1$ of the first diameter $30(a)$ portion of the tubular body 30 of the catheter hub 10.

Additional Embodiments

Variations of the securement system 100 is described below in connection with FIGS. 31-45 and FIGS. 61-75 that have different incident angles and anchor pad outer profiles. In both of these embodiments, the channel axis C is desirably skewed relative to the base surface 140 of the retainer 120. An incident angle θ defined between the base surface 140 and the channel axis C preferably is less than 45°. More preferably, the incident angle θ ranges between 5° and 30°. The base surface 140 of the retainer 120 illustrated in FIGS. 31-45 has an incident angle of approximately 7°. The base surface 140 of the retainer 120 illustrated in FIGS. 61-75 has an incident angle of approximately 10°. Such incident angles may be preferred when the retainer is used for intravenous use. In another exemplifying embodiment for arterial use, the incident angle θ may equal about 22°.

In the embodiments illustrated in FIGS. 31-45 and FIGS. 61-75, the anchor pad 110 further includes elongated extensions that project from the generally rectangular shape in a proximal direction. The elongated sections form a concave section or notch that narrows the center of the anchor pad 110 proximate to the retainer 120 and on a proximal side of the pad 110. Only the shape of the anchor pad 110 and incident angle of the base surface 140 of these embodiments differ from the above-described securement system 100. Accordingly, the above description of the securement system 100 applies equally to the embodiments of FIGS. 31-45 and FIGS. 61-75, unless otherwise indicated.

Further variations of the retainer design are described below in connection with FIGS. 16-30 and FIGS. 46-61 that have different incident angles and include an adhesive covering at least a portion of the channel 130. The incident angle of the base surface 140 for the embodiment illustrated in FIGS. 16-30 is approximately 7° while the incident angle of the base surface 140 for the embodiment illustrated in FIGS. 46-61 is approximately 10°.

As described above, inhibiting movement of the catheter hub 10 in the longitudinal direction when the catheter is secured within the channel 130 is desirably accomplished by the one or more abutment surfaces 160, 180. In addition, the interaction between the contact area on the inner surface of the channel 130 and the tubular body 30 of the catheter hub 10 creates friction to inhibit longitudinal movement through the channel 130. Beyond just having contact between the catheter hub 10 and inner surface of the channel 130, the actual shape of the channel 130 itself may further inhibit movement. For example, the interaction between the shape of the channel 130 and a corresponding shape of the catheter hub 10 inhibits longitudinal movement. Further, an adhesive cover placed over the top of the retainer and medical article can further inhibit relative movement.

Figure 25:
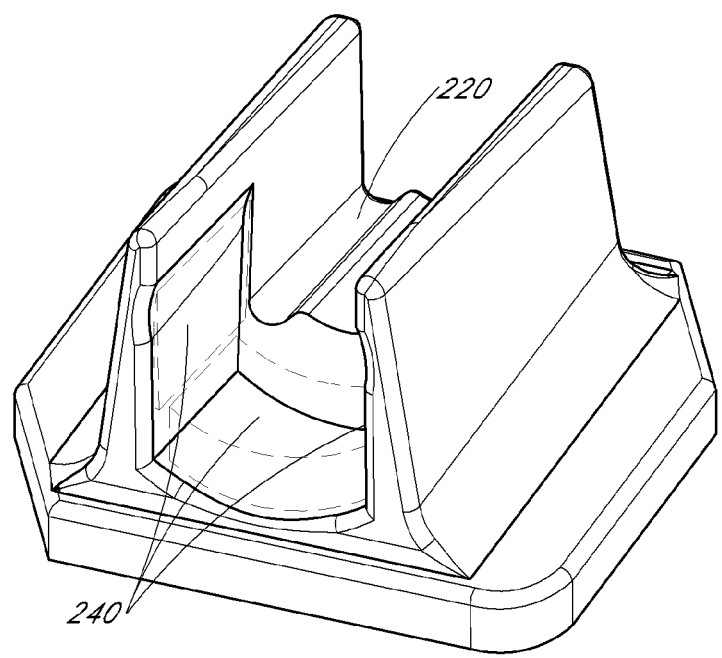
FIG. 25 is a rear perspective view of the retainer of FIG. 18.
Figure 26:
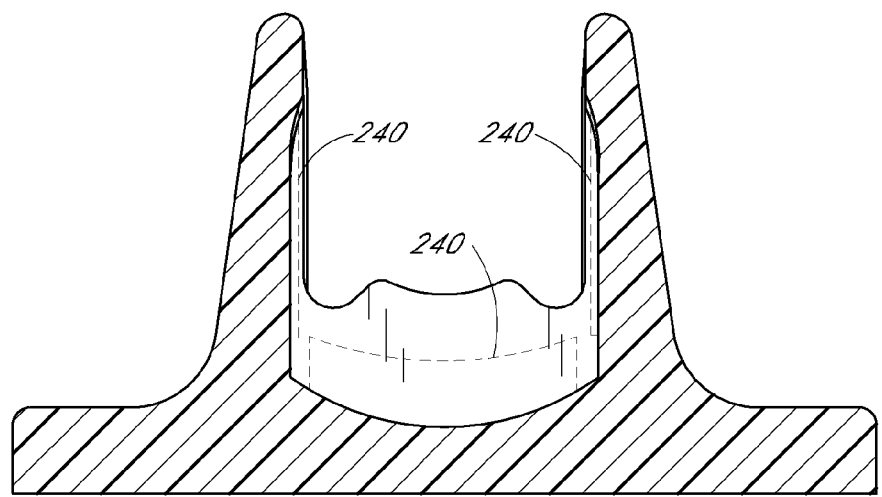
FIG. 26 is a cross-sectional view of the retainer of FIG. 18, taken along the 26-26 line.
Figure 27:
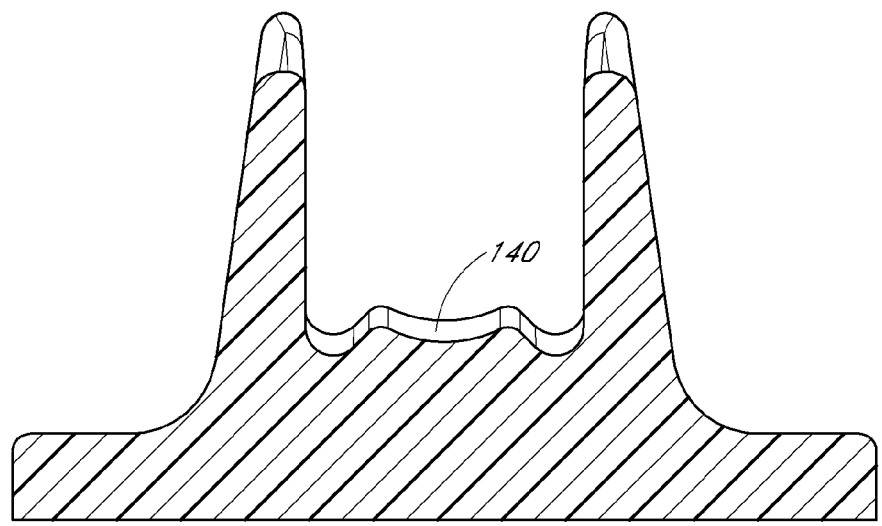
FIG. 27 is a cross-sectional view of the retainer of FIG. 18, taken along the 27-27 line.
Figure 28:
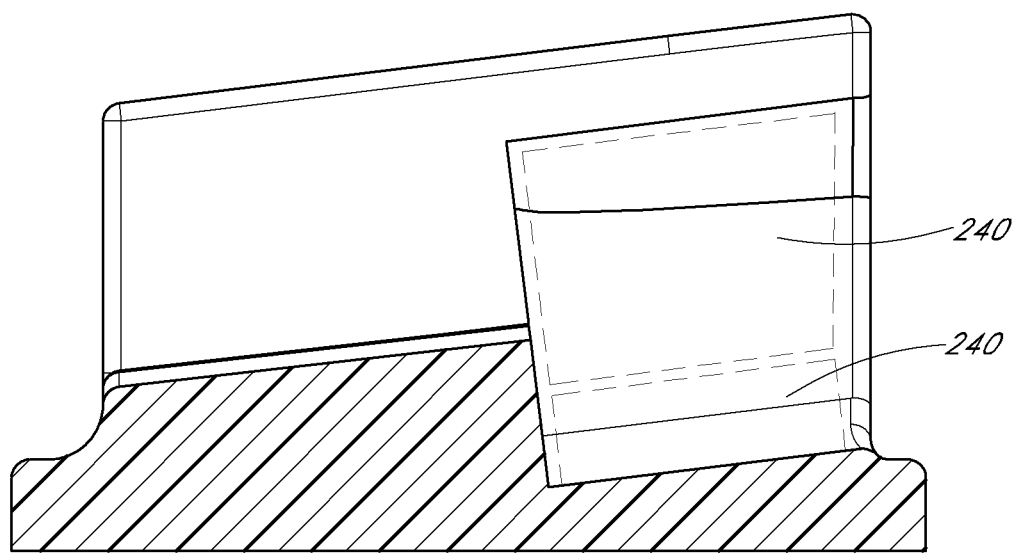
FIG. 28 is a cross-sectional view of the retainer of FIG. 18, taken along the 28-28 line.
Figure 29:
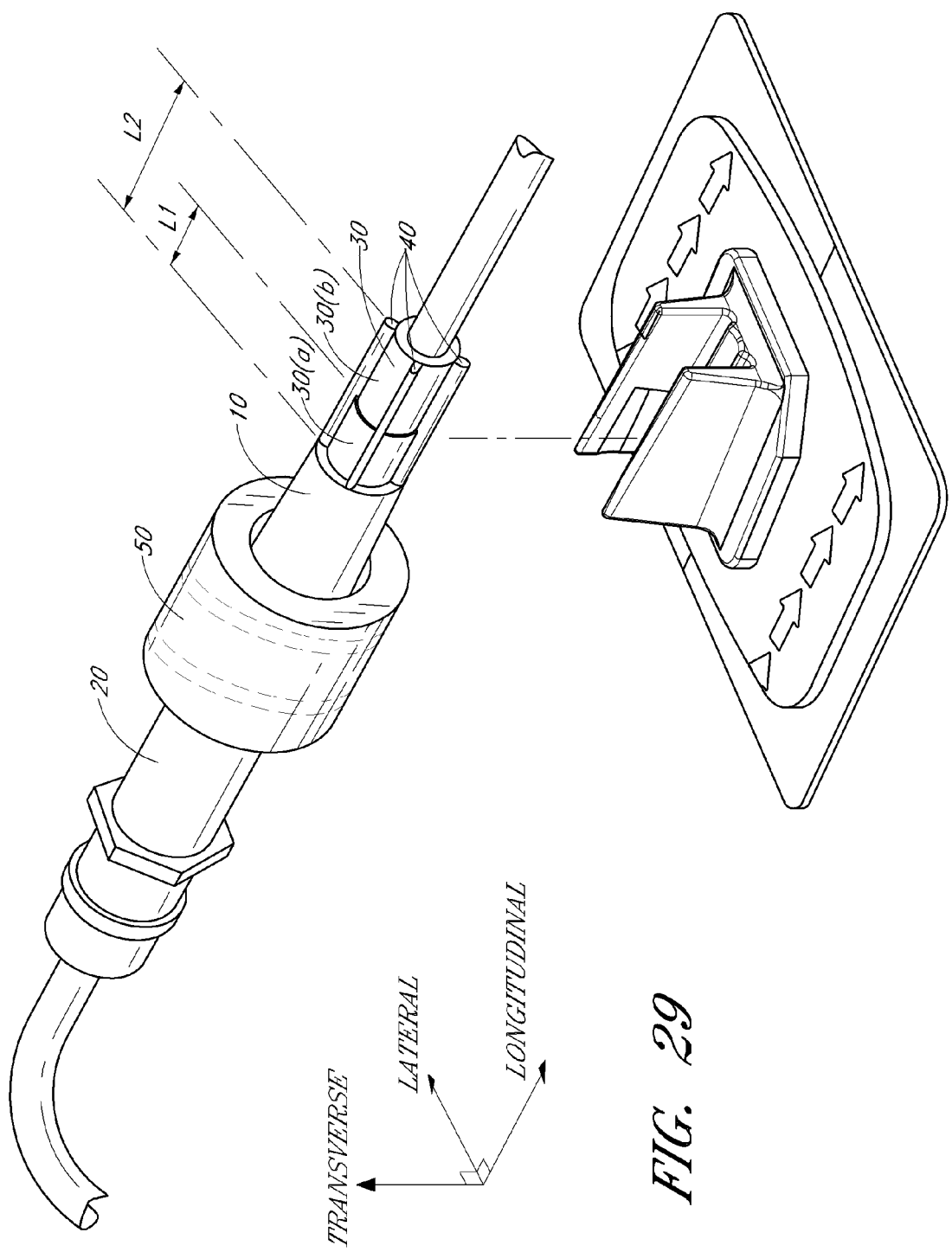
FIG. 29 is a perspective view of a catheter hub arranged above the retainer of the securement device from FIG. 16.
Figure 30:
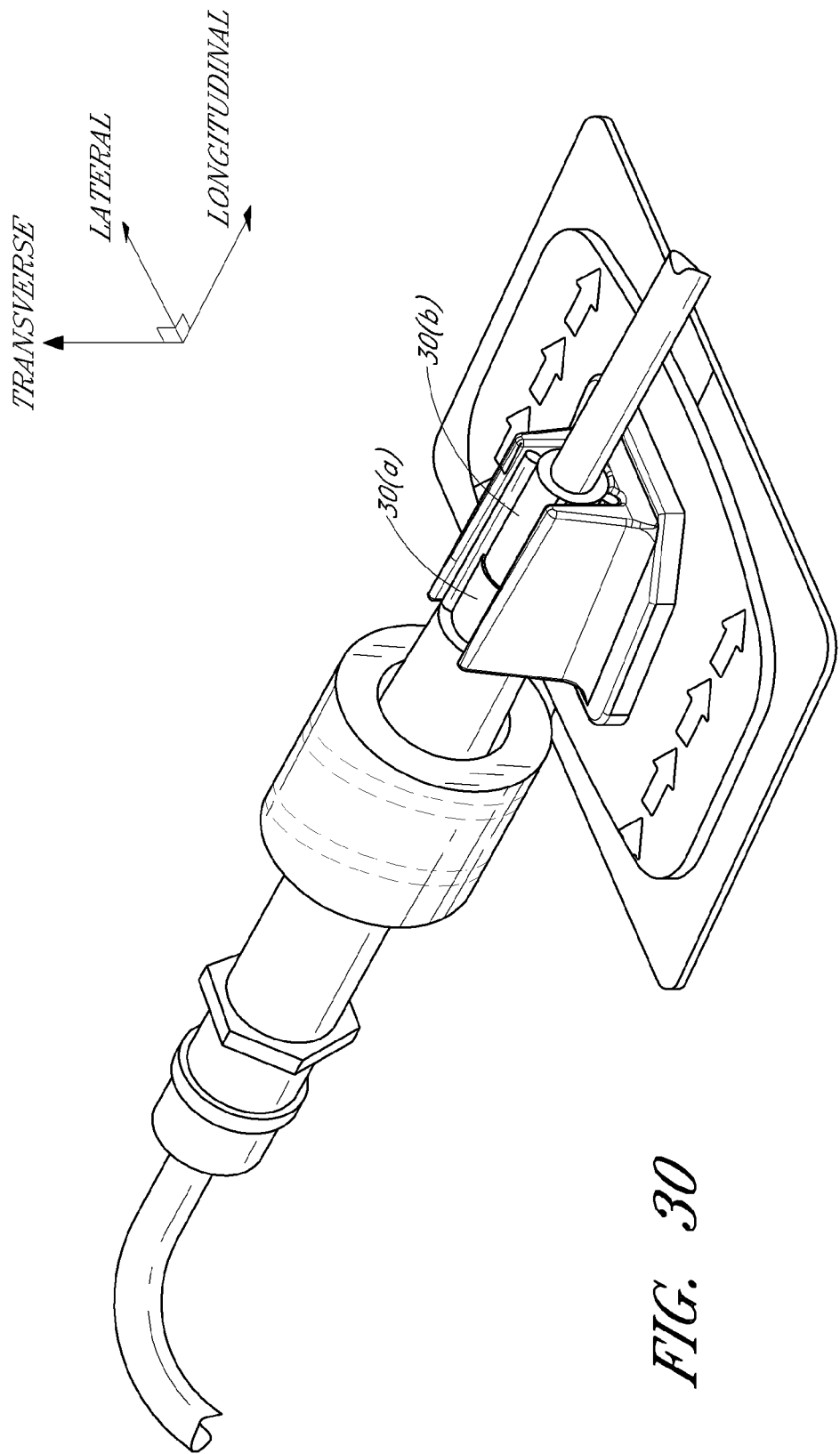
FIG. 30 is a perspective view of the catheter hub secured to the retainer of the securement device from FIG. 16.
Figure 55:
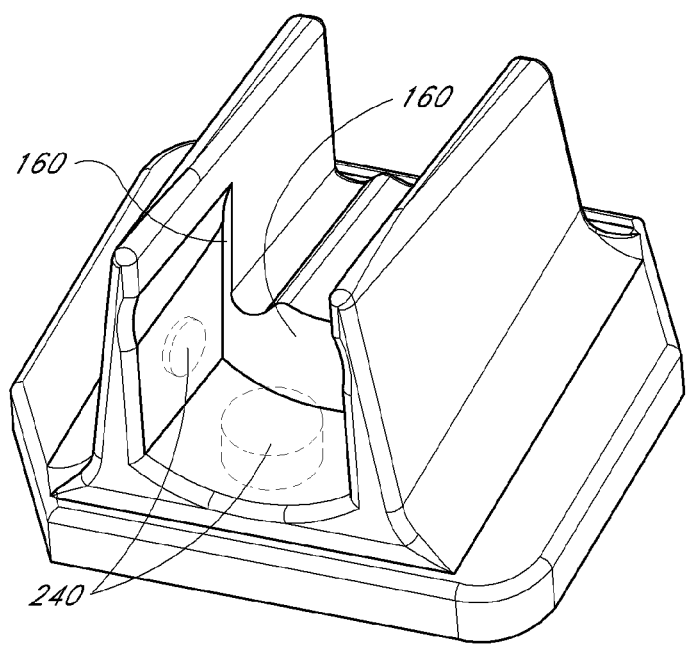
FIG. 55 is a rear perspective view of the retainer of FIG. 48.
Figure 56:
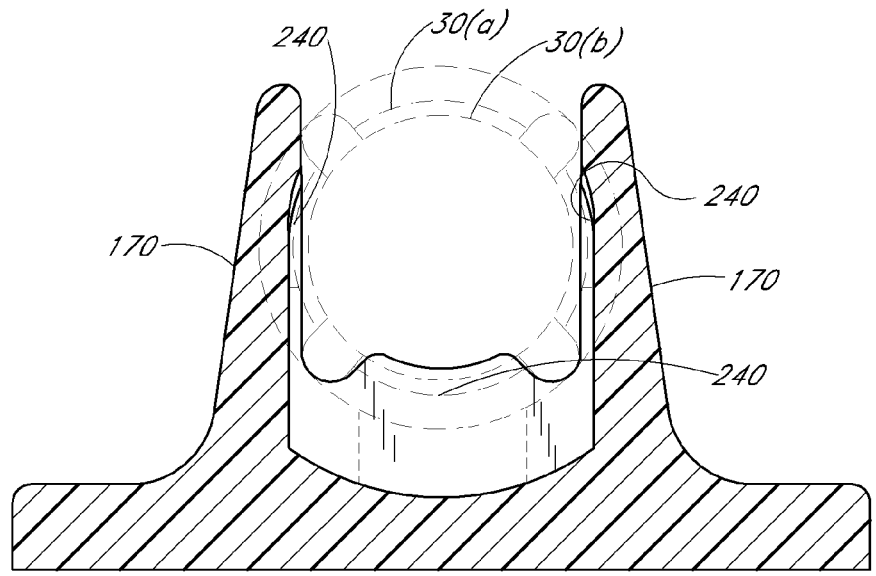
FIG. 56 is a cross-sectional view of the catheter hub from FIG. 60 secured within the retainer of FIG. 48, taken along the 56-56 line.
Figure 57:
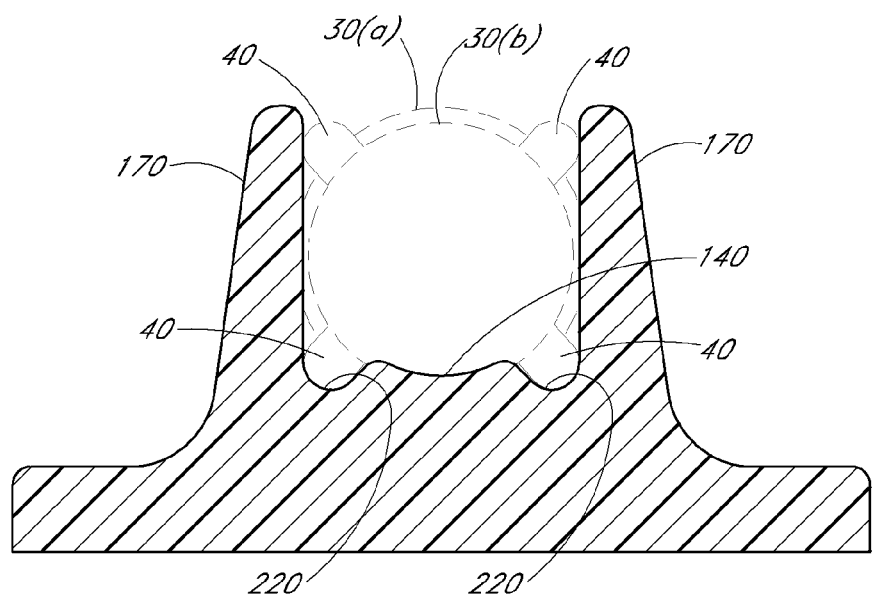
FIG. 57 is a cross-sectional view of the catheter hub from FIG. 60 secured within the retainer of FIG. 48, taken along the 57-57 line.
Figure 58:
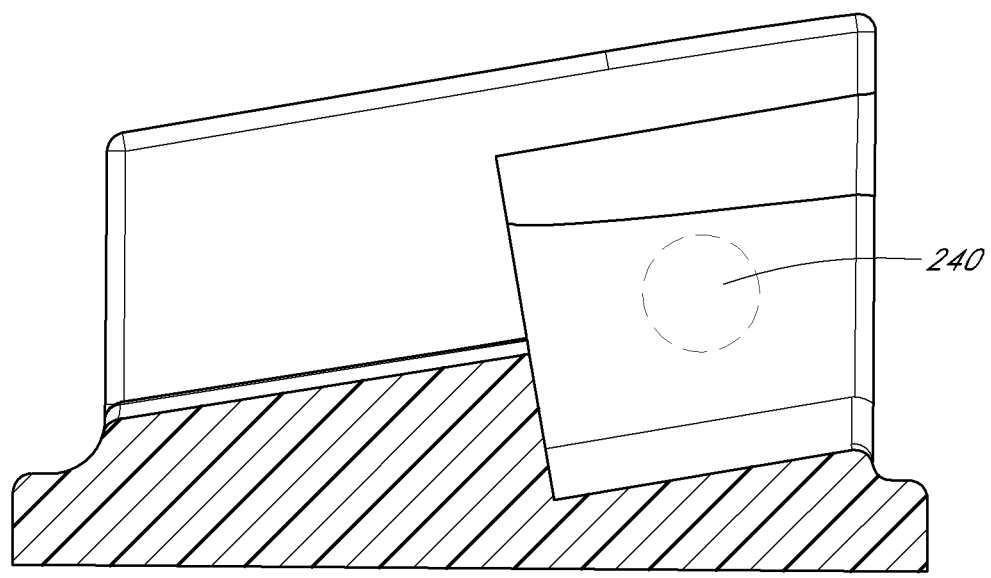
FIG. 58 is a cross-sectional view of the retainer of FIG. 48, taken along the 58-58 line.
Figure 59:
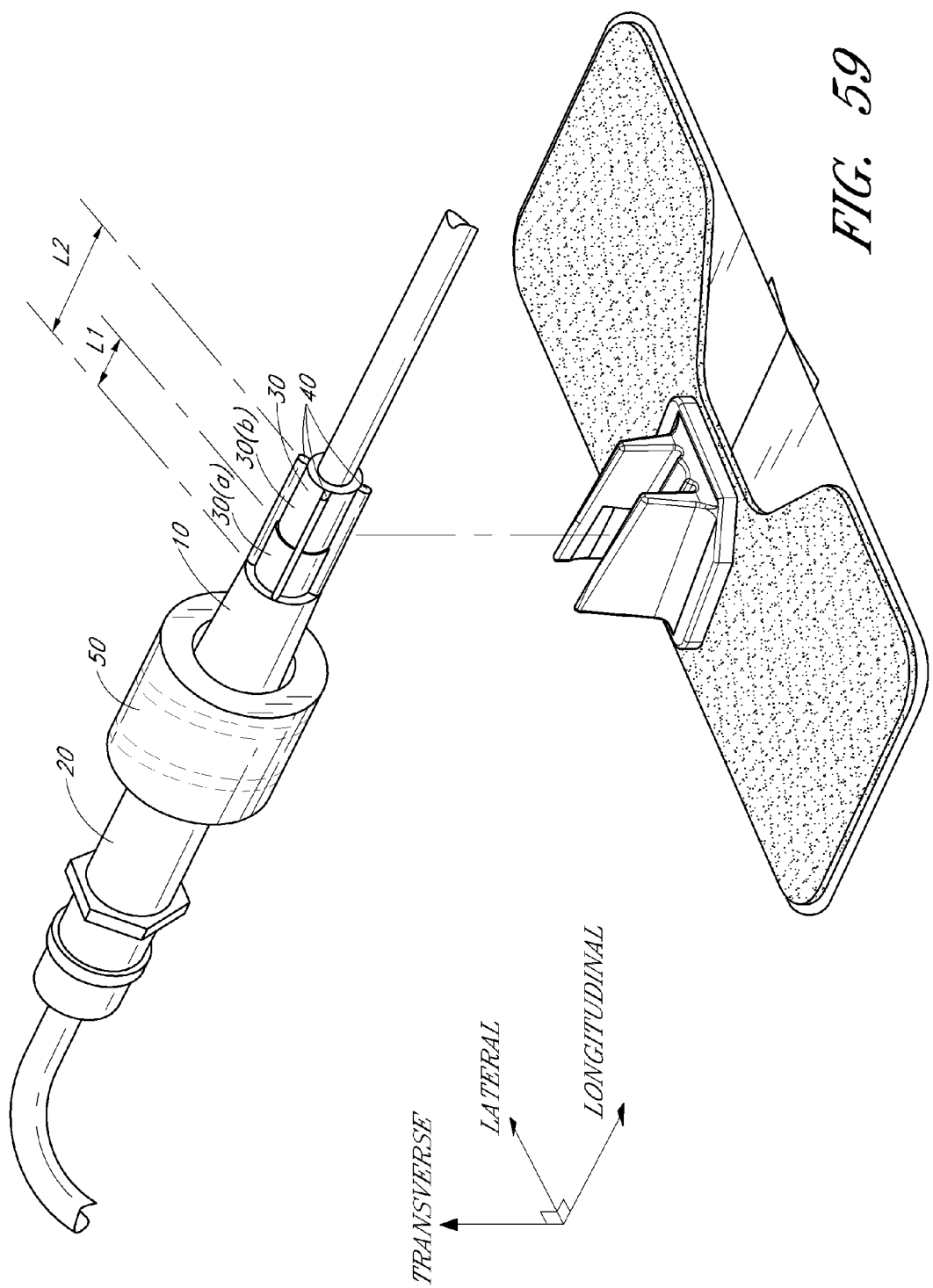
FIG. 59 is a perspective view of a catheter hub arranged above the retainer of the securement device from FIG. 46.
Figure 60:
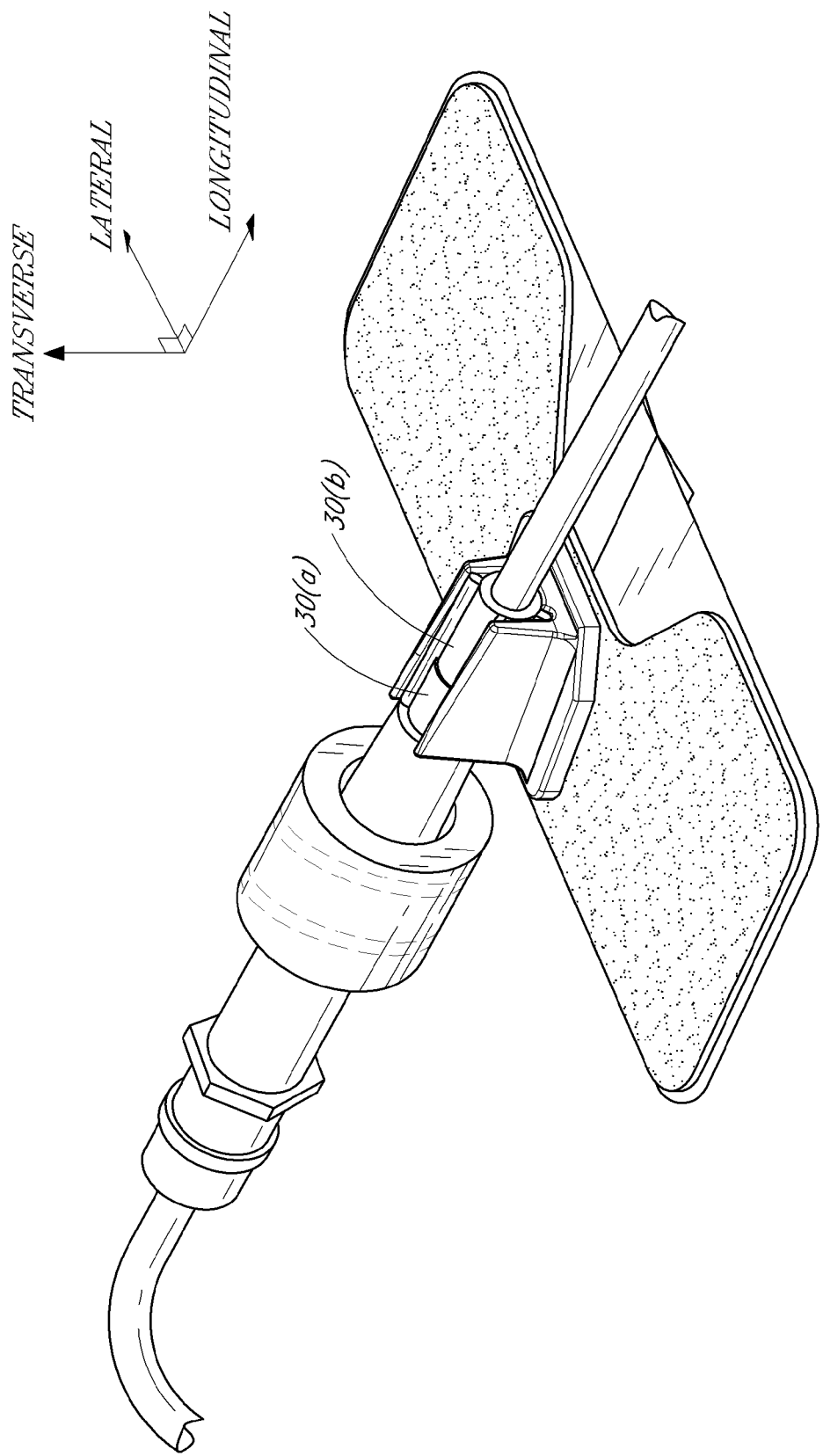
FIG. 60 is a perspective view of the catheter hub secured to the retainer of the securement device from FIG. 46.
Figure 61:
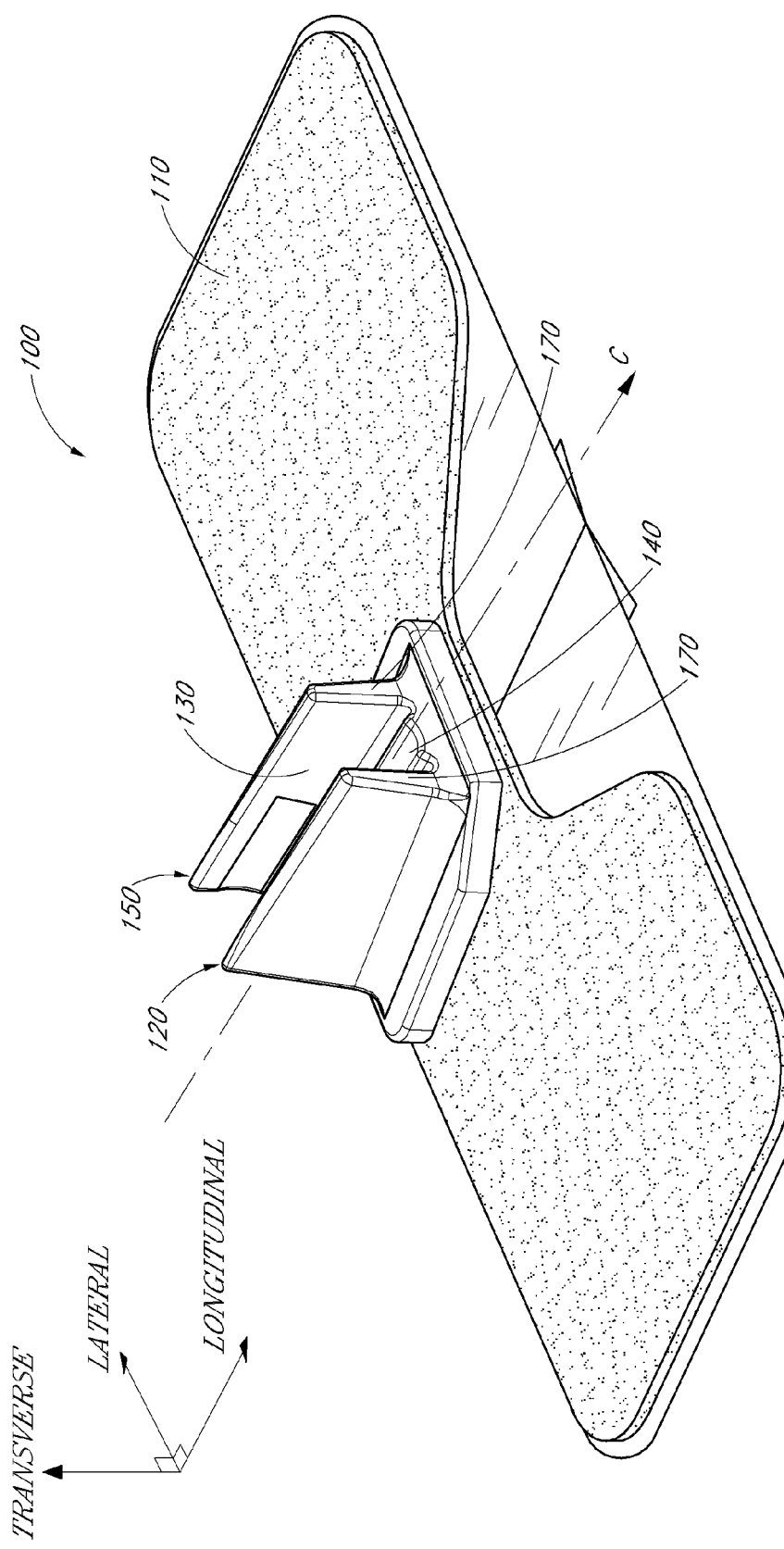
FIG. 61 is a perspective view of the securement device configured in accordance with another preferred embodiment of the present invention that includes an incident angle of approximately ten degrees.
Figure 62:
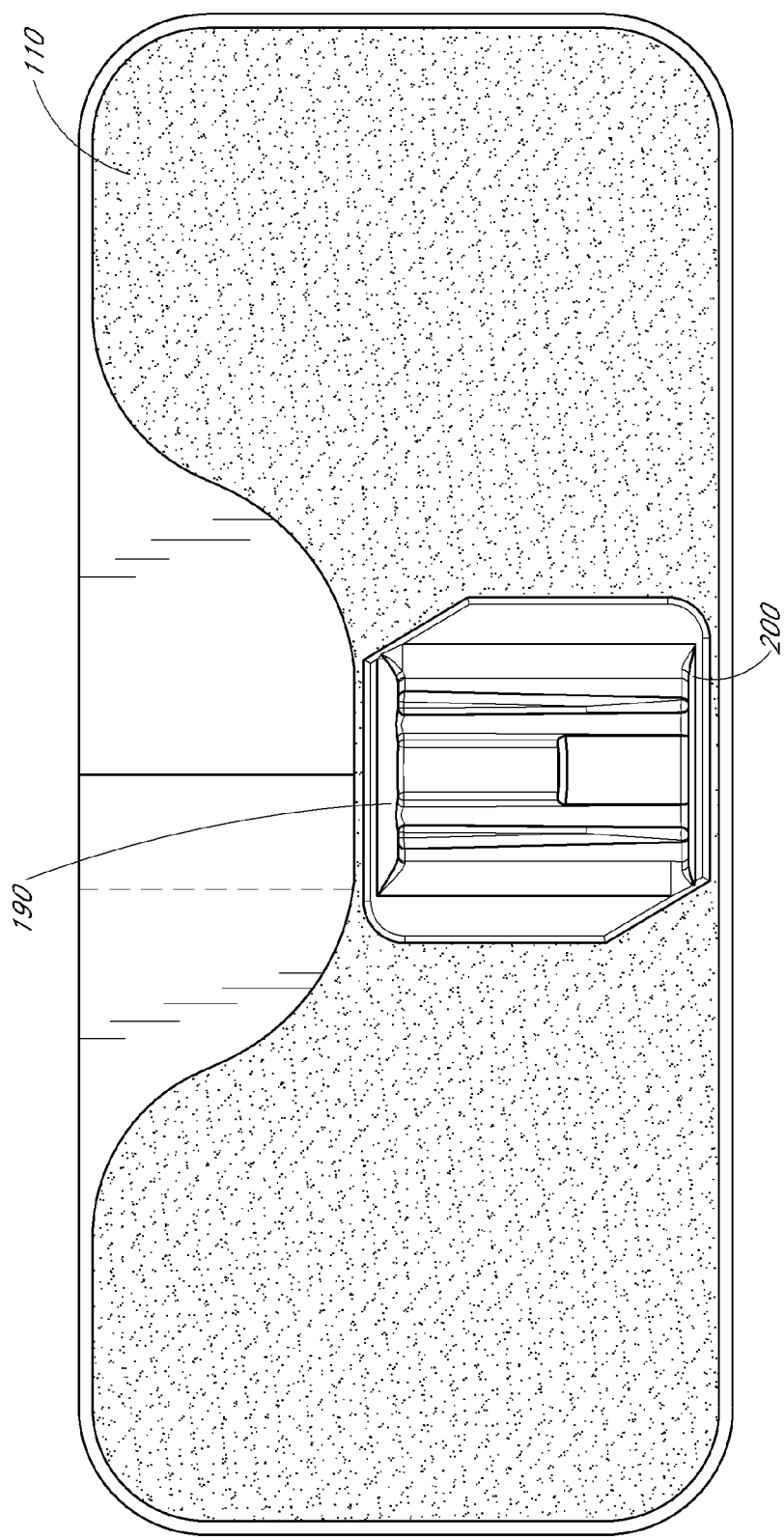
FIG. 62 is a top plan view of the retainer and anchor pad of FIG. 61.
Figure 63:
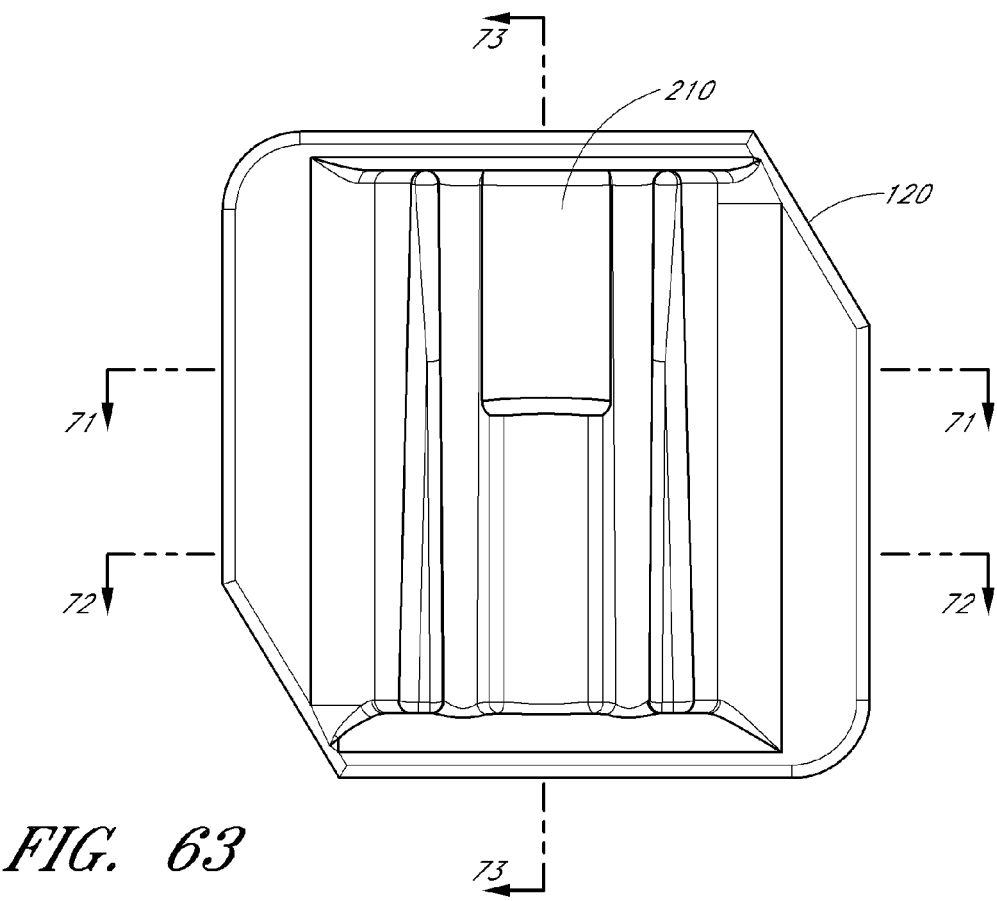
FIG. 63 is a top plan view of the retainer of FIG. 62.
Figure 64:
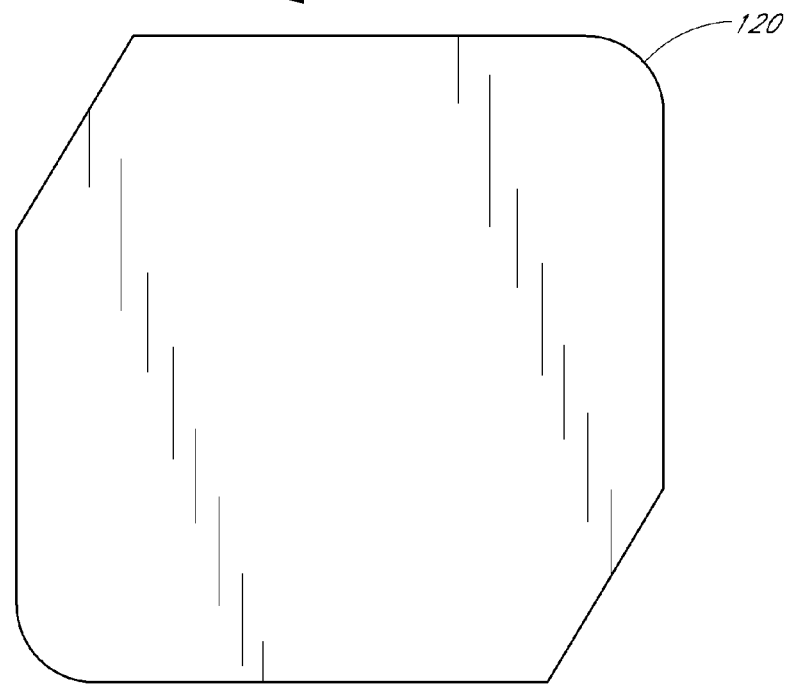
FIG. 64 is a bottom view of the retainer of FIG. 63.
Figure 65:
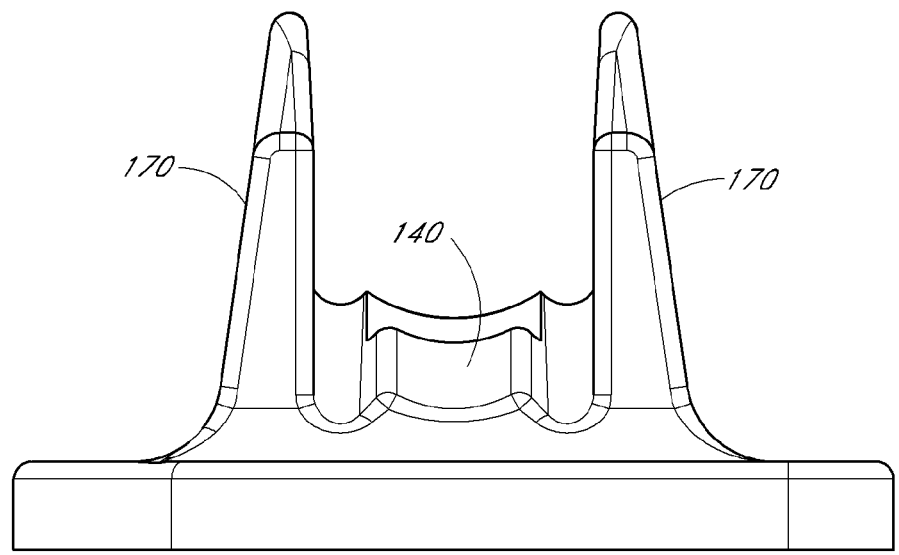
FIG. 65 is a front side view of the retainer of FIG. 63.
Figure 66:
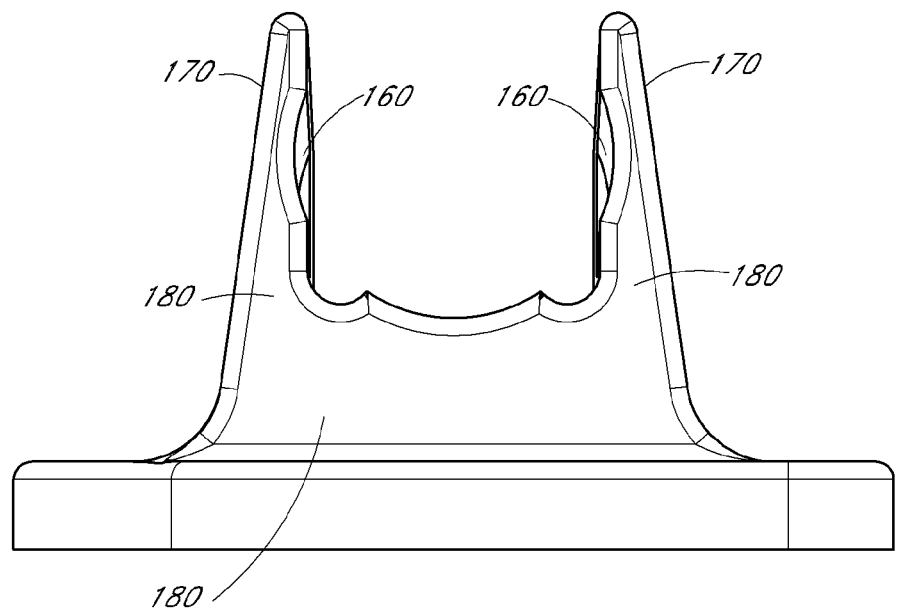
FIG. 66 is a rear side view of the retainer of FIG. 63.
Figure 67:
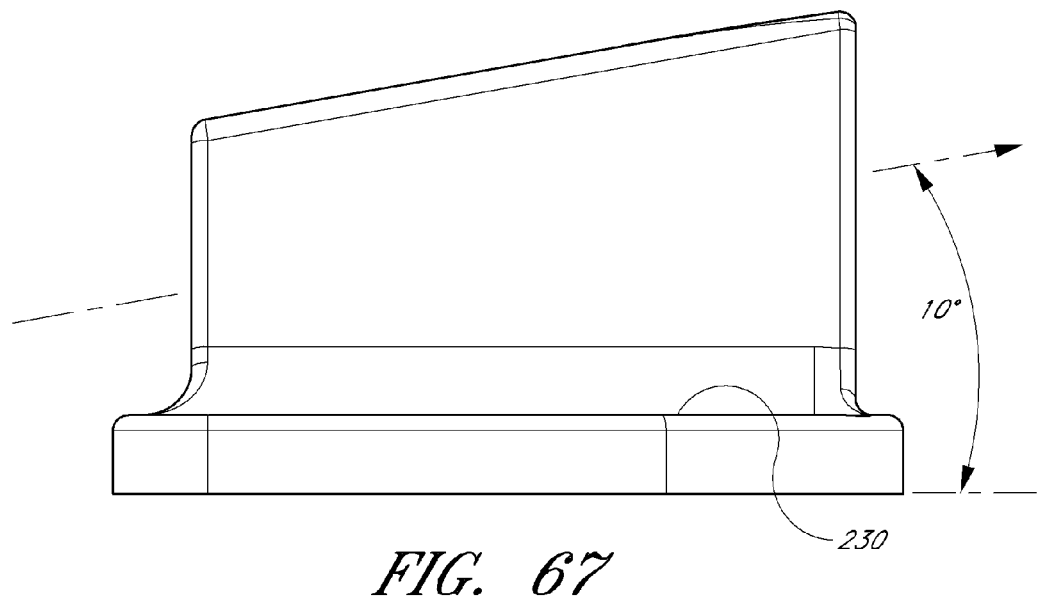
FIG. 67 is a side view of the retainer of FIG. 63.
Figure 68:
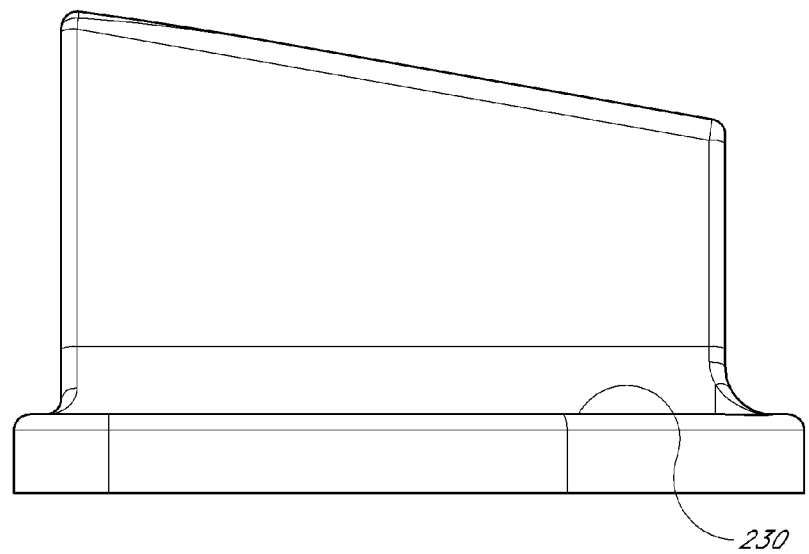
FIG. 68 is an opposite side view of the retainer of FIG. 63.
Figure 69:
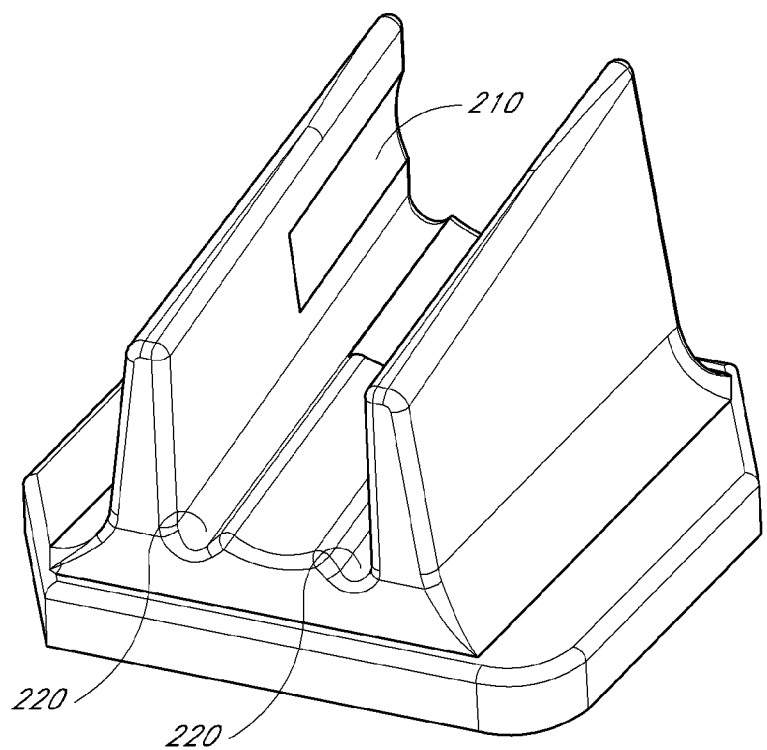
FIG. 69 is a front perspective view of the retainer of FIG. 63.
Figure 70:
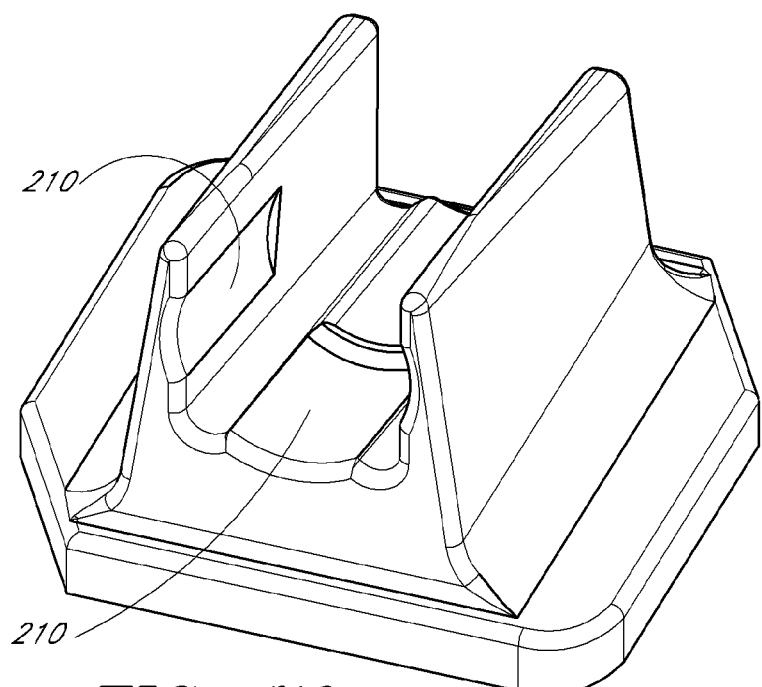
FIG. 70 is a rear perspective view of the retainer of FIG. 63.

Another possible retention mechanism to inhibit axial movement of the catheter hub 10 relative to the retainer 120 involves an adhesive spot 240 as is most clearly illustrated in FIGS. 25 and 55. An adhesive spot 240 may be advantageously disposed upon at least a portion of the inside of the channel 130. As is illustrated in FIG. 25, the adhesive spot 240 may take a form which generally fills one or more recesses or receptacles in the channel 130 while defining an outer surface that is disposed with respect to the adjacent inner surface of the channel 130 so as to contact the catheter hub 10 when the catheter hub 10 is placed within the channel 130. The adhesive spot 240 may extend into the channel 130 so as to interfere and conform to the outer surface of the catheter hub 10. The one or more recesses may be disposed in the walls 170 and/or base surface 140. In the illustrated embodiment, recesses are disposed in both walls 170 and the base surface 140. FIGS. 56 and 57 illustrate the interfaces between the retainer 120 and the catheter hub 10, including at the longitudinal location of the adhesive spot 240.

The adhesive spot may take the form of a glue dot. Such glue dots are desirably formed of a material which exhibits high resistance to shear and which can be peeled off of the catheter without leaving a residue. Such an adhesive is sold by All-Pak Inc. of New Berlin, Wis. as part number GD-06 "Super High Tack Glue Dot." Multiple glue dots may be used, or a single glue dot may be disposed on only one side of the channel of the retainer 120. It is not necessary for multiple glue dots to be used; a single glue dot disposed upon either the walls 170 or base surface 140 may advantageously be used to provide greater frictional and/or transverse forces between the retainer 120 and the catheter hub 10.

Furthermore, the adhesive spot 240 need not be a single point of adhesive. In certain embodiments such as illustrated in FIG. 25, the adhesive spot 240 is a region composed of an elastic and compressively deformable material such Kraton polymer compounds. Such a compound includes Dynaflex G2706 available from GLS Corporation, as well as other thermoplastic elastomers or silicone or urethane epoxies.

This region also need not be round. As is illustrated in FIG. 25, a large region of the surface of the channel 130 is covered with a suitable material, such as Kraton. Alternatively, the entire surface of the base surface 140 might be covered with a thin layer of adhesive to advantageously provide additional traction and transverse bias between the catheter and retainer.

Other means of producing an appropriate adhesive spot 240 for use with various embodiments include without limitation: treating a portion of the surface of the channel 130 chemically or electrically to adjust its surface friction or compressibility; spraying or spreading an adhesive coating onto a portion of the grooves 210, 220 of the retainer; attaching peel-off adhesive members to portions of the channel; injection molding regions of adhesive or compressible material, such as Kraton, to a portion of the surface of the channel; or such other means as are known in the art.

Another retention mechanism to inhibit axial movement of the catheter hub 10 involves one or more friction ridges located on the contact area of the channel 130. The ridges can be integrally formed with the retainer 120 and project into the channel 130. The ridges can lie generally normal to the central axis C through the channel 130. When so arranged, the friction ridges gently, but securely bite or press into an outer surface of the catheter hub 10.

Another possible retention mechanism to inhibit axial movement of the catheter hub 10 relative to the retainer 120 involves one or more securement barbs. The securement barbs can be used to retain the catheter hub in the longitudinal direction. In certain embodiments, each barb has a generally conical shape with a blunt tip. The barb may extend into the channel 130.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct securement systems in accordance with principles of the present invention.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present retainer has been described in the context of particularly preferred embodiments, the skilled artisan will appreciate, in view of the present disclosure, that certain advantages, features and aspects of the retainer may be realized in a variety of other applications, many of which have been noted above. For example, while particularly useful for small-scale applications, such as the illustrated medical application, the skilled artisan can readily adopt the principles and advantages described herein to a variety of other applications, including larger scale devices. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A securement system for securing a medical article to the skin of a patient, the system comprising:
    an anchor pad having a lower surface at least partially covered by an adhesive for contacting the patient's skin;
    a medical article having a generally elongated tubular body, a ridge circumscribing at least a portion of the tubular body, and at least one spline extending generally perpendicular to the ridge and on both sides of the ridge, the ridge defining a contact surface; and
    a retainer being supported by the anchor pad and having,
        a pair of upstanding walls separated by a base region to define a channel therebetween,
        a longitudinal access opening disposed on an upperside of the retainer,
        at least one groove disposed in the channel and extending from a distal end portion of the retainer to a proximal end portion of the retainer, the at least one groove being generally parallel to the channel and being sized and shaped so as to receive at least a portion of the spline when the medical article is secured within the retainer, and
        an abutment surface disposed in the channel and generally perpendicular to the at least one groove, the abutment surface cooperating with the contact surface on the medical article to inhibit longitudinal movement of the medical article relative to the retainer in at least one direction when the spline is disposed within the groove and the medical article is secured within the retainer.

2. The system of claim 1, wherein the abutment surface is formed on one of the pair of walls and the base region.

3. The system of claim 1, wherein the abutment surface is formed on the base region and each of the pair of wall.

4. The system of claim 1, wherein the abutment surface is discontinuous.

5. The system of claim 1, wherein the abutment surface circumscribes the channel for approximately 180 degrees.

6. The system of claim 1, wherein an incident angle defined between the base region and a channel axis is between 0° and 45°.

7. The system of claim 1, wherein the at least one groove is formed at an intersection of one of the pair of walls and the base region.

8. The system of claim 1, wherein the medical article comprises a second spline and the retainer comprises a second groove, the second groove being sized and shaped so as to receive at least a portion of the second spline.

9. The system of claim 1 further comprising a distal abutment surface, the distal abutment surface being defined at least in part by a distal edge of the pair of walls and disposed so as to contact a surface of the medical article at least when the medical article is disposed within the retainer.

10. The system of claim 1, wherein the channel has a generally conical shape.

11. The system of claim 1 further comprising an adhesive spot disposed so as to contact at least a portion of the medical article at least when the medical article is secured within the retainer.

12. The system of claim 11, wherein the adhesive spot is disposed on the abutment surface.

13. The system of claim 11, wherein the adhesive spot is disposed in the channel.

14. The system of claim 1, wherein the at least one groove extends for an entire length of the channel.

15. A retainer for securing a medical article, the medical article having a generally elongated tubular body, a ridge circumscribing at least a portion of the tubular body, and at least one spline extending generally perpendicular to the ridge and on both sides of the ridge, the ridge defining a contact surface, the retainer comprising:
    a pair of upstanding walls separated by a base region to define a channel therebetween;
    at least one groove disposed in the channel and extending from a distal end portion of the retainer to a proximal end portion of the retainer, the at least one groove being sized and shaped so as to receive at least a portion of the at least one spline of the medical article; and
    an abutment surface disposed in the channel and generally perpendicular to the at least one groove, the at least one abutment surface cooperating with the contact surface to inhibit longitudinal movement of the medical article relative to the retainer in at least one direction at least when the spline is disposed within the groove and the medical article is secured within the retainer.

16. The retainer of claim 15, wherein the abutment surface is formed on at least one of the pair of walls and the base region.

17. The retainer of claim 15, wherein the abutment surface is discontinuous.

18. The retainer of claim 15 further comprising a distal abutment surface, the distal abutment surface being defined at least in part by a distal edge of the pair of walls and disposed so as to contact a surface of the medical article at least when the medical article is disposed within the retainer.

19. The retainer of claim 15 further comprising an adhesive spot disposed so as to contact at least a portion of the medical article at least when the medical article is secured within the retainer.

20. The retainer of claim 15, wherein the at least one groove extends for an entire length of the channel.

21. A method of securing a medical article to a patient, the medical article having a generally elongated tubular body, a ridge circumscribing at least a portion of the tubular body, and a pair of splines extending generally perpendicular to the ridge and on both sides of the ridge, the ridge defining a contact surface, the method comprising:
    providing a retainer having a channel, a pair of longitudinal grooves disposed within the channel and separated by a base surface, the at least one groove extending from a distal end portion of the retainer to a proximal end portion of the retainer, and at least one abutment;
    locating the retainer with respect to the medical article so as to generally align the pair of splines with the pair of grooves; and
    pushing the medical article towards the channel so that at least a portion of the splines are received within the grooves; and sliding the splines of the medical article in the grooves until the contact surface of the medical article abuts the at least one abutment surface.

22. The method of claim 21 further comprising adhering the retainer to the patient's skin.

* * * * *